(12) United States Patent
Richter

(10) Patent No.: US 8,828,077 B2
(45) Date of Patent: Sep. 9, 2014

(54) FLAT PROCESS OF PREPARING DRUG ELUTING STENTS

(75) Inventor: Jacob Richter, Arsuf (IL)

(73) Assignee: Medinol Ltd., Tel Aviv (IL)

( * ) Notice: Subject to any disclaimer, the term of this patent is extended or adjusted under 35 U.S.C. 154(b) by 53 days.

(21) Appl. No.: 13/068,266

(22) Filed: May 6, 2011

(65) Prior Publication Data

US 2011/0238152 A1    Sep. 29, 2011

Related U.S. Application Data

(63) Continuation-in-part of application No. 11/376,879, filed on Mar. 15, 2006, now Pat. No. 7,959,664.

(60) Provisional application No. 61/395,160, filed on May 7, 2010.

(51) Int. Cl.
| | |
|---|---|
| *A61F 2/06* | (2013.01) |
| *C25F 3/00* | (2006.01) |
| *A61F 2/915* | (2013.01) |
| *A61F 2/88* | (2006.01) |

(52) U.S. Cl.
CPC ........... *C25F 3/00* (2013.01); *A61F 2250/0068* (2013.01); *A61F 2/88* (2013.01); *A61F 2/915* (2013.01); *A61F 2240/001* (2013.01); *A61F 2002/91541* (2013.01)
USPC ........................................................ 623/1.42

(58) Field of Classification Search
USPC ...................................... 623/1.15, 1.42–1.46
See application file for complete search history.

(56) References Cited

U.S. PATENT DOCUMENTS

| 728,178 A | 5/1903 | Schmeltzer |
|---|---|---|
| 1,237,195 A | 8/1917 | Gargiulo |

(Continued)

FOREIGN PATENT DOCUMENTS

| CA | 2168121 | 12/1995 |
|---|---|---|
| CA | 2161509 | 4/1996 |

(Continued)

OTHER PUBLICATIONS

European Search Report dated Sep. 24, 2010, from related application No. EP 07713111.8, published as EP 2040773, 7 pages.

(Continued)

*Primary Examiner* — Alvin Stewart
(74) *Attorney, Agent, or Firm* — Cadwalader, Wickersham & Taft LLP

(57) ABSTRACT

The present invention provides a method of fabricating a drug delivery stent. In one embodiment, the method involves forming a stent pattern in a flat sheet, where the stent pattern includes reservoirs, generating a flat map of the reservoirs, filling the reservoirs with a composition based on the flat map, and then forming the filled stent pattern into a tubular shape and joining the sides. In another embodiment, the method involves forming a stent pattern in a flat sheet, generating a flat map of discrete portions of the stent pattern that are desirable locations for coating, coating the discrete portions with a composition based on the flat map, and then forming the coated stent pattern into a tubular shape and joining the sides. The invention provides advantages over current methods and drug-delivery stents in that it is faster, more accurate and more cost-efficient manufacturing process for fabricating drug delivery stents, that improves quality and consistency of drug delivery within and across batches of stents, and that permits automated a process of quality control. This method also allows for differential coating on the two surfaces of the stent struts, whereby the two sides are coated with different drugs and/or polymer combinations, or only one side of the strut is coated.

34 Claims, 43 Drawing Sheets
(5 of 43 Drawing Sheet(s) Filed in Color)

(56) References Cited

U.S. PATENT DOCUMENTS

| | | | |
|---|---|---|---|
| 1,429,328 A | 9/1922 | Domizi | |
| 1,629,813 A | 5/1927 | Stevenson | |
| 2,701,559 A | 2/1955 | Cooper | |
| 2,703,062 A | 3/1955 | Miller et al. | |
| 3,118,406 A | 1/1964 | Stanton | |
| 3,802,239 A | 4/1974 | Karmann et al. | |
| 3,882,845 A | 5/1975 | Bucalo | |
| 3,889,685 A | 6/1975 | Miller et al. | |
| 4,018,230 A | 4/1977 | Ochiai et al. | |
| 4,152,573 A | 5/1979 | Saurin et al. | |
| 4,183,102 A | 1/1980 | Guiset | |
| 4,483,340 A | 11/1984 | Fogarty et al. | |
| 4,503,569 A | 3/1985 | Dotter | |
| 4,513,596 A | 4/1985 | Usher | |
| 4,582,559 A | 4/1986 | Tanielian et al. | |
| 4,638,984 A | 1/1987 | Puisais et al. | |
| 4,680,031 A | 7/1987 | Alonso | |
| 4,776,337 A | 10/1988 | Palmaz | |
| 4,893,623 A | 1/1990 | Rosenbluth | |
| 4,907,336 A * | 3/1990 | Gianturco | 29/515 |
| 4,969,458 A | 11/1990 | Wikto | |
| 4,994,066 A * | 2/1991 | Voss | 606/108 |
| 4,994,071 A | 2/1991 | MacGregor | |
| 5,007,926 A | 4/1991 | Derbyshire | |
| 5,026,967 A | 6/1991 | Bell et al. | |
| 5,028,303 A | 7/1991 | Kuwabara et al. | |
| 5,041,126 A | 8/1991 | Gianturco | |
| 5,102,417 A | 4/1992 | Palmaz | |
| 5,114,548 A | 5/1992 | Rhoades | |
| 5,147,391 A | 9/1992 | Lane | |
| 5,195,984 A | 3/1993 | Schatz | |
| RE34,327 E | 7/1993 | Kreamer | |
| 5,304,200 A | 4/1994 | Spaulding | |
| 5,314,444 A | 5/1994 | Gianturco | |
| 5,354,309 A | 10/1994 | Schnepp-Pesch et al. | |
| 5,356,433 A | 10/1994 | Rowland et al. | |
| 5,367,833 A | 11/1994 | Rhoades et al. | |
| 5,383,892 A | 1/1995 | Cardon et al. | |
| 5,405,518 A | 4/1995 | Hsieh et al. | |
| 5,421,955 A * | 6/1995 | Lau et al. | 216/48 |
| 5,423,885 A | 6/1995 | Williams | |
| 5,441,515 A | 8/1995 | Khosravi et al. | |
| 5,443,497 A * | 8/1995 | Venbrux | 623/1.13 |
| 5,443,500 A | 8/1995 | Sigwart | |
| 5,449,372 A | 9/1995 | Schmaltz et al. | |
| 5,449,373 A | 9/1995 | Pinchasik et al. | |
| 5,449,382 A | 9/1995 | Dayton | |
| 5,474,563 A * | 12/1995 | Myler et al. | 606/108 |
| 5,514,154 A | 5/1996 | Lau et al. | |
| 5,527,354 A | 6/1996 | Fontine et al. | |
| 5,527,435 A | 6/1996 | Arnau | |
| 5,534,287 A | 7/1996 | Lukic | |
| 5,536,388 A | 7/1996 | Dinan et al. | |
| 5,540,712 A | 7/1996 | Kleshinski | |
| 5,540,713 A | 7/1996 | Schnepp-Pesch et al. | |
| 5,578,075 A | 11/1996 | Dayton | |
| 5,589,051 A | 12/1996 | Henington | |
| 5,607,445 A * | 3/1997 | Summers | 623/1.22 |
| 5,618,299 A | 4/1997 | Khosravi et al. | |
| 5,620,738 A | 4/1997 | Fan et al. | |
| 5,632,771 A | 5/1997 | Boatman et al. | |
| 5,632,840 A | 5/1997 | Campbell | |
| 5,643,314 A | 7/1997 | Carpenter et al. | |
| 5,649,952 A * | 7/1997 | Lam | 623/1.15 |
| 5,649,977 A | 7/1997 | Campbell | |
| 5,650,116 A * | 7/1997 | Thompson | 264/561 |
| 5,674,242 A * | 10/1997 | Phan et al. | 606/198 |
| 5,693,085 A | 12/1997 | Buirge et al. | |
| 5,700,286 A | 12/1997 | Tartagalia et al. | |
| 5,707,385 A | 1/1998 | Williams | |
| 5,707,386 A | 1/1998 | Schnepp-Pesch et al. | |
| 5,713,949 A | 2/1998 | Jayaraman | |
| 5,716,396 A | 2/1998 | Williams, Jr. | |
| 5,733,302 A | 3/1998 | Myler et al. | |
| 5,733,330 A | 3/1998 | Cox | |
| 5,741,293 A | 4/1998 | Wijay | |
| 5,746,691 A | 5/1998 | Frantzen | |
| 5,755,781 A | 5/1998 | Jayaraman | |
| 5,766,238 A | 6/1998 | Lau et al. | |
| 5,766,710 A | 6/1998 | Turnlund et al. | |
| 5,775,734 A | 7/1998 | George, Jr. | |
| 5,776,161 A | 7/1998 | Globerman | |
| 5,776,183 A | 7/1998 | Kanesaka | |
| 5,779,732 A | 7/1998 | Amundson | |
| 5,788,558 A | 8/1998 | Klein | |
| 5,800,515 A | 9/1998 | Nadal et al. | |
| 5,800,526 A * | 9/1998 | Anderson et al. | 623/1.16 |
| 5,807,404 A | 9/1998 | Richter | |
| 5,810,872 A | 9/1998 | Kanesaka et al. | |
| 5,824,053 A | 10/1998 | Khosravi et al. | |
| 5,824,054 A | 10/1998 | Khosravi et al. | |
| 5,836,964 A * | 11/1998 | Richter et al. | 606/194 |
| 5,843,164 A | 12/1998 | Frantzen et al. | |
| 5,843,172 A | 12/1998 | Yan | |
| 5,860,999 A | 1/1999 | Schnepp-Pesch et al. | |
| 5,868,781 A | 2/1999 | Killion | |
| 5,879,697 A | 3/1999 | Ding et al. | |
| 5,897,587 A | 4/1999 | Martakos et al. | |
| 5,902,475 A * | 5/1999 | Trozera et al. | 205/655 |
| 5,906,640 A | 5/1999 | Penn et al. | |
| 5,906,759 A * | 5/1999 | Richter | 219/121.63 |
| 5,907,893 A * | 6/1999 | Zadno-Azizi et al. | 29/6.1 |
| 5,911,752 A * | 6/1999 | Dustrude et al. | 623/1.1 |
| 5,913,897 A | 6/1999 | Corso, Jr. et al. | |
| 5,922,005 A * | 7/1999 | Richter et al. | 606/192 |
| 5,922,393 A | 7/1999 | Jayaraman | |
| 5,925,061 A * | 7/1999 | Ogi et al. | 623/1.2 |
| 5,925,063 A | 7/1999 | Khosravi | |
| 5,941,895 A * | 8/1999 | Myler et al. | 606/195 |
| 5,972,016 A | 10/1999 | Morales | |
| 5,980,552 A | 11/1999 | Pinchasik et al. | |
| 5,980,972 A | 11/1999 | Ding et al. | |
| 5,984,963 A | 11/1999 | Ryan | |
| 5,997,703 A * | 12/1999 | Richter | 204/297.1 |
| 6,063,111 A | 5/2000 | Hieshima et al. | |
| 6,066,168 A * | 5/2000 | Lau et al. | 623/1.16 |
| 6,080,191 A * | 6/2000 | Summers | 623/1.22 |
| 6,090,136 A | 7/2000 | McDonald et al. | |
| 6,102,943 A * | 8/2000 | McGuinness | 623/1.12 |
| 6,110,199 A * | 8/2000 | Walak | 623/1.18 |
| 6,114,049 A * | 9/2000 | Richter | 428/571 |
| 6,120,535 A | 9/2000 | McDonald et al. | |
| 6,123,723 A | 9/2000 | Konya et al. | |
| 6,129,658 A * | 10/2000 | Delfino et al. | 600/3 |
| 6,156,052 A * | 12/2000 | Richter et al. | 606/191 |
| 6,156,062 A | 12/2000 | McGuinness | |
| 6,197,048 B1 | 3/2001 | Richter | |
| 6,253,443 B1 * | 7/2001 | Johnson | 29/557 |
| 6,261,320 B1 * | 7/2001 | Tam et al. | 623/1.15 |
| 6,284,305 B1 | 9/2001 | Ding et al. | |
| 6,299,755 B1 | 10/2001 | Richter | |
| 6,312,463 B1 | 11/2001 | Rourke et al. | |
| 6,327,772 B1 * | 12/2001 | Zadno-Azizi et al. | 29/557 |
| 6,355,055 B1 | 3/2002 | Waksman et al. | |
| 6,355,058 B1 | 3/2002 | Pacetti et al. | |
| 6,416,537 B1 | 7/2002 | Martakos et al. | |
| 6,432,133 B1 * | 8/2002 | Lau et al. | 623/1.15 |
| 6,451,044 B1 * | 9/2002 | Naghavi et al. | 607/96 |
| 6,506,437 B1 | 1/2003 | Harish et al. | |
| 6,527,919 B1 * | 3/2003 | Roth | 204/192.15 |
| 6,530,951 B1 | 3/2003 | Bates et al. | |
| 6,545,748 B1 * | 4/2003 | Trozera | 355/104 |
| 6,554,848 B2 * | 4/2003 | Boylan et al. | 606/191 |
| 6,554,942 B2 | 4/2003 | Solar et al. | |
| 6,569,194 B1 * | 5/2003 | Pelton | 623/1.15 |
| 6,574,851 B1 | 6/2003 | Mirizzi | 29/527.5 |
| 6,626,933 B1 * | 9/2003 | Lau et al. | 623/1.11 |
| 6,626,937 B1 | 9/2003 | Cox | 623/1.18 |
| 6,660,019 B1 * | 12/2003 | Richter et al. | 606/191 |
| 6,673,385 B1 | 1/2004 | Ding et al. | |
| 6,692,522 B1 * | 2/2004 | Richter | 623/1.15 |
| 6,709,440 B2 * | 3/2004 | Callol et al. | 606/108 |
| 6,726,829 B2 * | 4/2004 | Trozera | 205/655 |
| 6,726,923 B2 | 4/2004 | Iyer et al. | |

(56) References Cited

U.S. PATENT DOCUMENTS

| | | | |
|---|---|---|---|
| 6,730,349 B2 | 5/2004 | Schwarz et al. | |
| 6,736,844 B1 | 5/2004 | Glatt et al. | |
| 6,743,462 B1 | 6/2004 | Pacetti | |
| 6,752,826 B2 | 6/2004 | Holloway et al. | |
| 6,753,071 B1 | 6/2004 | Pacetti | |
| 6,758,859 B1 | 7/2004 | Dang et al. | |
| 6,774,985 B2* | 8/2004 | Trozera | 355/104 |
| 6,805,898 B1 | 10/2004 | Wu et al. | |
| 6,808,738 B2* | 10/2004 | DiTizio et al. | 427/2.24 |
| 6,821,293 B2* | 11/2004 | Pinchasik | 623/1.15 |
| 6,849,085 B2* | 2/2005 | Marton | 623/1.13 |
| 6,849,089 B2 | 2/2005 | Stoll | |
| 6,907,106 B1* | 6/2005 | McIntyre et al. | 378/68 |
| 7,008,645 B2 | 3/2006 | Golomb et al. | |
| 7,060,093 B2 | 6/2006 | Dang et al. | |
| 7,105,018 B1 | 9/2006 | Yip et al. | |
| 7,135,039 B2* | 11/2006 | De Scheerder et al. | 623/1.42 |
| 7,163,555 B2 | 1/2007 | Dinh | |
| 7,175,874 B1* | 2/2007 | Pacetti | 427/2.25 |
| 7,179,289 B2 | 2/2007 | Shanley | |
| 7,192,438 B2 | 3/2007 | Margolis | |
| 7,208,009 B2* | 4/2007 | Richter | 623/1.15 |
| 7,208,010 B2 | 4/2007 | Shanley et al. | |
| 7,314,482 B2* | 1/2008 | Richter et al. | 623/1.15 |
| 7,316,710 B1* | 1/2008 | Cheng et al. | 623/1.15 |
| 7,318,837 B2 | 1/2008 | Krivoruchko et al. | |
| 7,335,227 B2* | 2/2008 | Jalisi | 623/1.15 |
| 7,335,314 B2 | 2/2008 | Wu et al. | |
| 7,420,298 B2* | 9/2008 | Botos et al. | 310/12.14 |
| 7,435,255 B1 | 10/2008 | Rao | |
| 7,465,315 B2* | 12/2008 | Morris et al. | 623/1.15 |
| 7,513,907 B2* | 4/2009 | Lau et al. | 623/1.15 |
| 7,615,373 B2* | 11/2009 | Simpson et al. | 435/398 |
| 7,647,687 B2* | 1/2010 | Koch et al. | 29/557 |
| 7,650,179 B2* | 1/2010 | Redel et al. | 600/427 |
| 7,658,760 B2* | 2/2010 | Pelton et al. | 623/1.19 |
| 7,673,379 B1* | 3/2010 | Pacetti | 29/447 |
| 7,674,416 B2* | 3/2010 | Hong et al. | 264/261 |
| 7,691,400 B2* | 4/2010 | Francis | 424/423 |
| 7,699,890 B2* | 4/2010 | Yan | 623/1.44 |
| 7,704,275 B2* | 4/2010 | Schmid et al. | 623/1.16 |
| 7,722,662 B2* | 5/2010 | Steinke et al. | 623/1.16 |
| 7,789,907 B2* | 9/2010 | De Scheerder et al. | 623/1.42 |
| 7,828,840 B2* | 11/2010 | Biggs et al. | 623/1.44 |
| 7,833,261 B2* | 11/2010 | Chen et al. | 623/1.16 |
| 7,947,071 B2* | 5/2011 | Schmid et al. | 623/1.22 |
| 7,959,664 B2* | 6/2011 | Richter | 623/1.15 |
| 8,043,651 B2* | 10/2011 | O'Connor et al. | 427/2.1 |
| 8,192,785 B2* | 6/2012 | Pacetti | 427/2.1 |
| 8,431,149 B2* | 4/2013 | McMorrow et al. | 424/426 |
| 2002/0007209 A1* | 1/2002 | Scheerder et al. | 623/1.15 |
| 2002/0038767 A1* | 4/2002 | Trozera | 205/667 |
| 2002/0099438 A1 | 7/2002 | Furst | |
| 2002/0123798 A1* | 9/2002 | Burgermeister | 623/1.17 |
| 2002/0127327 A1 | 9/2002 | Schwarz et al. | |
| 2003/0040790 A1 | 2/2003 | Furst | |
| 2003/0083731 A1 | 5/2003 | Kramer et al. | |
| 2003/0106218 A1* | 6/2003 | Jalisi et al. | 29/896.6 |
| 2003/0125802 A1 | 7/2003 | Callol et al. | |
| 2003/0138950 A1 | 7/2003 | McAllister et al. | |
| 2003/0139801 A1* | 7/2003 | Sirhan et al. | 623/1.15 |
| 2003/0139803 A1 | 7/2003 | Sequin et al. | |
| 2003/0159920 A1* | 8/2003 | Roth | 204/192.12 |
| 2003/0191520 A1* | 10/2003 | Pelton | 623/1.15 |
| 2004/0073294 A1* | 4/2004 | Diaz et al. | 623/1.42 |
| 2004/0079737 A1* | 4/2004 | Pinchasik | 219/121.64 |
| 2004/0098089 A1* | 5/2004 | Weber | 623/1.13 |
| 2004/0098107 A1* | 5/2004 | Richter et al. | 623/1.15 |
| 2004/0149294 A1 | 8/2004 | Gianchandani et al. | |
| 2004/0162605 A1* | 8/2004 | Richter | 623/1.15 |
| 2004/0181277 A1 | 9/2004 | Furst | |
| 2004/0186553 A1 | 9/2004 | Yan | |
| 2004/0236412 A1 | 11/2004 | Brar et al. | |
| 2004/0243213 A9 | 12/2004 | Richter et al. | |
| 2005/0033407 A1* | 2/2005 | Weber et al. | 623/1.15 |
| 2005/0055080 A1* | 3/2005 | Istephanous et al. | 623/1.13 |
| 2005/0107870 A1 | 5/2005 | Wang et al. | |
| 2007/0056151 A1* | 3/2007 | Koch et al. | 29/282 |
| 2007/0077347 A1* | 4/2007 | Richter | 427/2.25 |
| 2007/0135707 A1* | 6/2007 | Redel et al. | 600/424 |
| 2007/0293936 A1* | 12/2007 | Dobak | 623/1.13 |
| 2008/0077222 A1 | 3/2008 | Johnson et al. | |
| 2008/0091263 A1 | 4/2008 | Iyer et al. | |
| 2008/0097579 A1 | 4/2008 | Shanley et al. | |
| 2008/0097582 A1 | 4/2008 | Shanley et al. | |
| 2008/0147164 A1* | 6/2008 | Gale et al. | 623/1.15 |
| 2008/0241218 A1* | 10/2008 | McMorrow et al. | 424/426 |
| 2008/0317827 A1 | 12/2008 | Wright et al. | |
| 2009/0062904 A1 | 3/2009 | Furst | |
| 2009/0176005 A1* | 7/2009 | Kramer | 427/2.1 |
| 2009/0192593 A1* | 7/2009 | Meyer et al. | 623/1.42 |
| 2009/0204204 A1 | 8/2009 | Falotico et al. | |
| 2009/0232964 A1* | 9/2009 | Chen | 427/2.25 |
| 2009/0319026 A1* | 12/2009 | Meyer | 623/1.16 |
| 2010/0096781 A1* | 4/2010 | Huang et al. | 264/435 |
| 2010/0100166 A1 | 4/2010 | Richter et al. | |
| 2011/0238152 A1* | 9/2011 | Richter | 623/1.15 |

FOREIGN PATENT DOCUMENTS

| | | |
|---|---|---|
| CA | 2468677 | 6/2003 |
| DE | 4104702 | 8/1992 |
| DE | 4303181 | 8/1994 |
| DE | 19581503 | 1/1997 |
| EP | 0183372 | 4/1986 |
| EP | 0274846 | 7/1988 |
| EP | 0382014 | 8/1990 |
| EP | 0541443 | 5/1993 |
| EP | 0554082 | 8/1993 |
| EP | 0604022 | 6/1994 |
| EP | 0621017 | 10/1994 |
| EP | 0709067 | 5/1996 |
| EP | 0732088 | 9/1996 |
| EP | 0732089 | 9/1996 |
| EP | 0819412 | 1/1998 |
| EP | 0839506 | 5/1998 |
| EP | 0895761 | 2/1999 |
| GB | 2135585 | 9/1984 |
| JP | 49-031568 A | 3/1974 |
| JP | 56-131014 A | 10/1981 |
| JP | 62-231657 | 10/1987 |
| JP | 63-230158 | 9/1988 |
| JP | 2-102669 | 4/1990 |
| JP | 05-200048 | 8/1993 |
| JP | 05-332231 | 12/1993 |
| JP | 06-181993 | 7/1994 |
| JP | 08-206226 | 8/1996 |
| JP | 08-507243 | 8/1996 |
| JP | 10-500582 | 1/1998 |
| JP | 2008-523914 T | 7/2007 |
| PL | 179854 | 4/1995 |
| PL | 180527 | 7/1995 |
| PL | 321656 | 8/1997 |
| RU | 2086209 | 7/1991 |
| RU | 1794547 | 2/1993 |
| RU | 2007969 | 2/1994 |
| RU | 2014194 | 6/1994 |
| RU | 2053734 | 2/1996 |
| SU | 450686 | 12/1974 |
| SU | 727385 | 4/1980 |
| SU | 895601 | 1/1982 |
| SU | 1318235 | 6/1982 |
| SU | 1199360 | 12/1985 |
| SU | 1389778 | 4/1988 |
| WO | WO 94/17754 | 8/1994 |
| WO | WO 95/03010 | 2/1995 |
| WO | WO 95/31945 | 11/1995 |
| WO | WO 96/03092 | 2/1996 |
| WO | WO 96/26689 | 9/1996 |
| WO | WO 96/33671 | 10/1996 |
| WO | WO 98/12989 | 4/1998 |
| WO | WO 98/27894 | 7/1998 |

(56) References Cited

FOREIGN PATENT DOCUMENTS

| WO | WO 98/38947 | 11/1998 |
|----|-------------|---------|
| WO | WO 2004/105635 | 12/2004 |
| WO | WO 2006/086069 | 8/2006 |

OTHER PUBLICATIONS

International Search Report and Written Opinion for PCT/IB07/00563, Mar. 19, 2008.
Office Actions and Responses from U.S. Appl. No. 08/774,970, issued as Patent No. 5,906,759 on May 25, 1999: • Restriction/Election Requirement mailed Mar. 31, 1998; • Response to Restriction/Election Requirement filed on May 8, 1998; • Non-Final Office Action mailed Jun. 30, 1998; • Response to Non-Final Office Action filed on Dec. 3, 1998 with Extension of Time and Amended Drawings; and • Notice of Allowance mailed Dec. 23, 1998.
Office Actions and Responses from U.S. Appl. No. 09/109,844, issued as Patent No. 6,692,522 on Feb. 17, 2004: • Non-Final Office Action mailed Jul. 8, 1999; • Response to Non-Final Office Action filed on Jan. 18, 2000 with three month extension of time; • Non-Final Office Action mailed on Apr. 12, 2000; • Response to Non-Final Office Action filed on Oct. 16, 2000 with three-month extension of time; • Non-Final Office Action mailed on Jan. 31, 2001; • Response to Non-Final Office Action filed on Aug. 6, 2001 with three-month extension of time; • Final Rejection mailed on Oct. 22, 2001; • Notice of Appeal field on Apr. 30, 2002; • Advisory Action mailed on May 14, 2002; • Supplemental Amendment as part of Submission under 37 CFR 1.114 filed on Aug. 30, 2002 with Request for Continued Examination; • Restriction Requirement/Election mailed on Nov. 8, 2002; • Response to Restriction Requirement/Election filed on Nov. 27, 2002 ; • Non-Final Office Action mailed on Jan. 13, 2003; • Response to Non-Final Office action filed on May 13, 2003 with Extension of Time; • Final Rejection mailed on Jul. 25, 2003; • Amendment and Response to Final Rejection filed on Sep. 22, 2003; • Notice of Allowance mailed on Sep. 22, 2003.
Office Actions and Response from Continuation U.S. Appl. No. 10/781,541, issued as Patent No. 7,208,009 on Apr. 24, 2007: • Non-Final Office Action mailed on Nov. 1, 2005; • Response to non-Final Office Action filed on Apr. 19, 2006 with Extension of Time; • Non-Final Office Action mailed on Jul. 5, 2006; • Response to Non-Final Office Action filed on Oct. 3, 2006; and • Notice of Allowance mailed on Dec. 22, 2006.
Office Actions and Response of related U.S. Appl. No. 11/376,879, issued as Patent No. 7,959,664 on Jun. 14, 2011: • Non-Final Rejection mailed Mar. 13, 2009; • Response to Non-Final Rejection filed Jun. 15, 2009; • Final Rejection mailed Oct. 19, 2009; • Letter Requesting Interview with Examiner dated Jan. 5, 2010; • Examiner Interview Summary Record dated Jan. 27, 2010; • Response to Final Rejection with Request for Continued Examination and extension of time filed Feb. 10, 2010; • Non-Final Rejection mailed Jul. 22, 2010; • Response to Non-Final Rejection filed Oct. 22, 2010; • Notice of Allowanced mailed Jan. 7, 2011; • Patent Term Adjustment Petition filed Jul. 11, 2011; and • Petition Decision on Patent Term Adjustment mailed Aug. 23, 2011.

\* cited by examiner

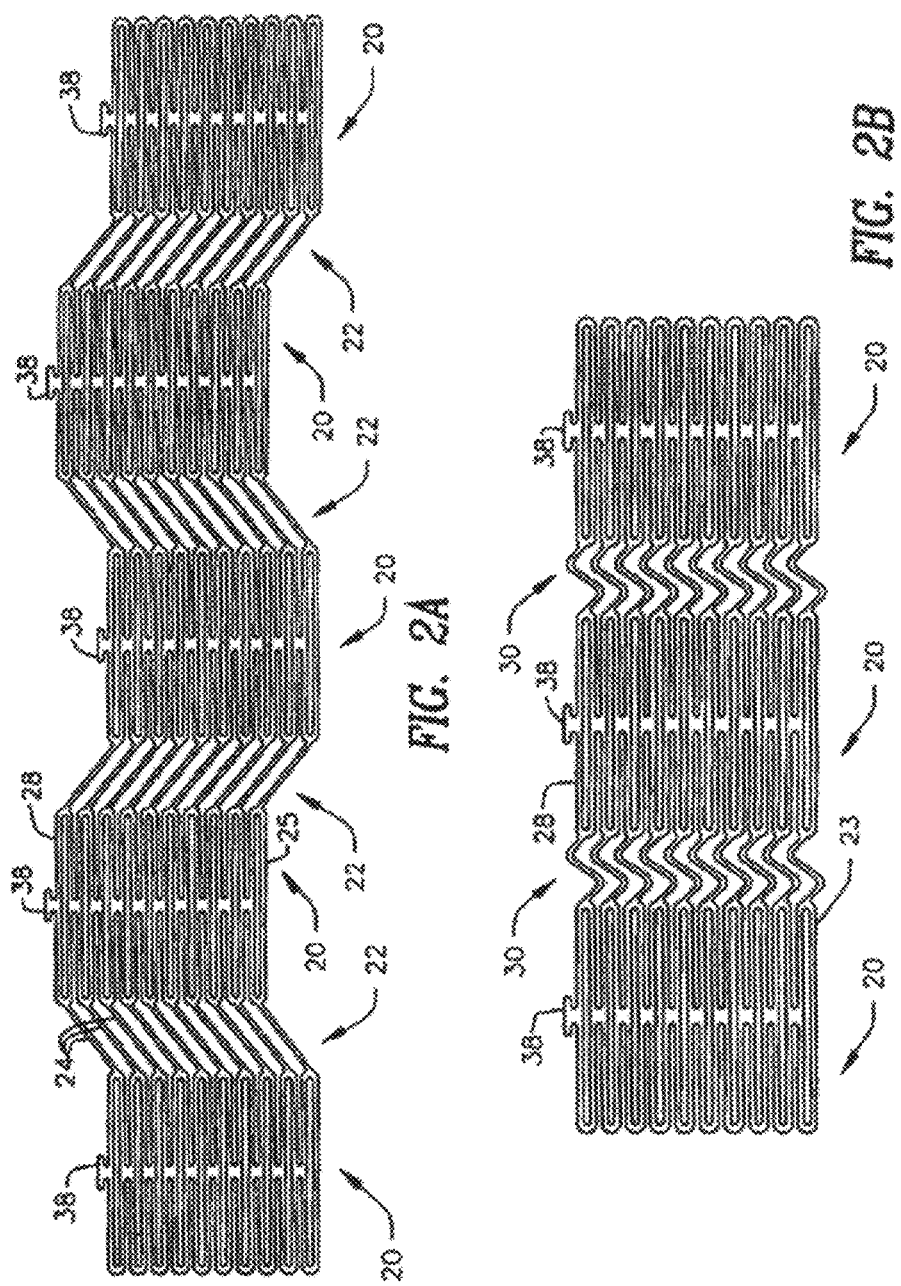

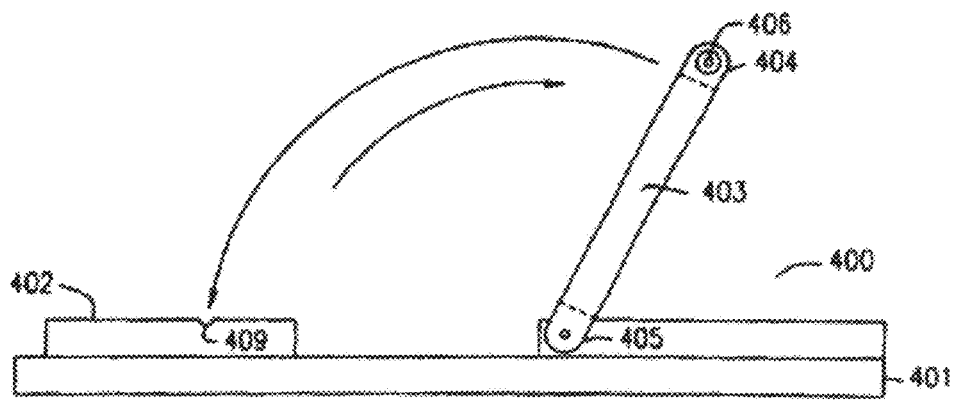
FIG. 34
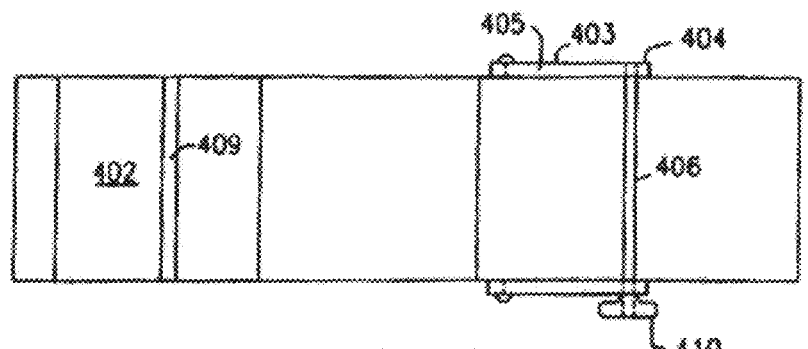
FIG. 35
FIG. 36
FIG. 37

FLAT PROCESS OF PREPARING DRUG ELUTING STENTS

CROSS REFERENCE TO RELATED APPLICATIONS

This application claims benefit of priority of provisional application No. 61/395,160, and is a continuation-in-part of co-pending U.S. application Ser. No. 11/376,879, filed Mar. 15, 2006. These priority applications are hereby incorporated by reference in their entireties.

FIELD OF THE INVENTION

The present invention relates to methods of fabricating stents that can deliver a therapeutic agent to the vessel in which the stent is implanted. More specifically, the invention is directed to a process of depositing a composition into reservoirs of the base material of the stent and a process of coating discrete portions of the base material of the stent, while in the form of a flat sheet or panel prior to forming the base material into a tubular device.

BACKGROUND OF THE INVENTION

Stents are known in the art. They are typically formed of a cylindrical metal mesh that can expand when pressure is internally applied or when self-expanding metals are employed. Stents can be formed by cutting a pattern from metal tubes or flat sheets of metal that are later folded and formed into tubular stents, or alternatively by forming wire or metal mesh strips wrapped into a tubular shape.

As described in U.S. Pat. No. 4,776,337 to Palmaz, the cylindrical metal mesh shape is produced by laser cutting a thin walled metal tube. The laser cuts away all but the lines and curves of the mesh.

The method of U.S. '337 is applicable for relatively large mesh shapes and for meshes whose lines are relatively wide. However, for more delicate and/or intricate shapes, the spot size of the laser is too large.

Stents have been coated with various compounds and therapeutic agents to enhance their effectiveness, for example, to facilitate the acceptance of the stent into a blood vessel lumen or to facilitate the delivery of therapeutic agents to a target site within a blood vessel. Such drug coated stents have been used in recent years to attempt to reduce the occurrence of restenosis. Restenosis is a common complication that may arise following implantation of vascular stents. Restenosis is a response to the trauma of stent implantation involving scar tissue formation that reduces vessel lumen diameter and may result in recurrence of vessel occlusion or critical narrowing. To avoid the need for further revascularization procedures, which can increase trauma and risk, stents have been designed that deliver beneficial agents to the vessel lumen to prevent or minimize the restenosis problem.

Various methods have been employed to apply coatings to stents. For example, the cylindrical surface of a finished stent may be sprayed with a coating substance or a spinning cylindrical stent may be dipped into a coating solution to achieve the desired coating. See, e.g., U.S. Pat. No. 5,980,972 to Ding et al.

U.S. Pat. No. 6,984,411 to Palasis et al. describes a method for applying a coating to stents while rolling the stents about their longitudinal axis, where the stents are loaded onto rotating holders affixed to a conveyor, and the conveyor carries the rotating stents and holders through a coating applicator one or more times.

During the manufacture of coated stents, care must be taken to ensure that the coating is uniformly applied to the stent surface. A disadvantage of these prior stent coating processes is that uniformity of stent coating is difficult to achieve when spraying the cylindrical surface of a finished stent. These prior stent coating processes also do not allow for the differential treatment of the luminal side of the stent and the vessel wall side of the stent.

A further disadvantage of currently available coating methods of stents is that the coating is made on both the luminal side and vessel wall side of the stent. Not having the ability to provide differential treatment of the luminal and vessel sides of the stent may limit potential applications of the coated stent.

A further disadvantage is that the desired ratio between coating on both surfaces, whether equal or not, is hard or impossible to control. A further disadvantage of existing processes is their inherent slow pace that limits capacity and cost efficiency. A still further disadvantage of coated stents is that coatings can sometimes crack and peel at portions of the stent that bend or deform during crimping or during expansion of the stent.

Thus, there remains a need in the art to have a process of uniformly coating stents, providing a coating having differential treatment of the luminal side of the stent and the vessel wall side of the stent, and coating discrete portions of the stent. It is also desirable for such process to be substantially faster and more cost efficient.

In alternative approaches to enhancing stent effectiveness, stents have been designed with openings or drug depots built into the metal mesh containing a beneficial agent, or made from a porous metal which is loaded with one or more drugs. For example, as described in U.S. Pat. No. 7,179,289 to Shanley, stents may be designed with a plurality of openings or recesses, for example by laser drilling, and filled with various therapeutic agents. The openings or recesses are preferably located in inflexible portions or non-expanding members of the stent. Filling of the openings may proceed by masking the inside of the tubular structure (and optionally the outer surface of the stent structure), spraying the therapeutic agent onto the stent (or dipping the stent), optionally spinning the stent to produce even distribution of the drug composition, and then, where the external surface is not masked, removing the residual drug composition from the stent structure. See U.S. Pat. No. 7,163,555 to Dinh; see also, U.S. Pat. No. 7,060,093 to Dang. Porous metal stents having a desired pore size in the metal structure are fabricated from one or more powdered metals which are pressure-cast into a stent-like form or into sheets or tubes from which the stents are produced, as described in U.S. Pat. No. 6,253,443 to Johnson. The porous metal is impregnated with the drugs to be released therefrom by dipping or soaking in the medium containing the drug.

The porous metal stents and drug depot stents deliver beneficial agents, such as pharmaceutical compounds, without increasing the effective wall thickness or impacting expansion properties of the stent. While these stents thereby overcome some of the problems associated with coated stents or membrane-covered stents, they are beset with disadvantages of their own. For example, existing processes for filling the openings or depots are inefficient, because of the inherent slow pace of the multi-step process of capping, masking, spraying/dipping and removing unwanted drug coating from stent elements, which limits capacity and cost efficiency, and wastes therapeutic agent associated with the coating/removal process of filling the openings. The filling process also can lead to unacceptable variations in quality between stents and within a stent, for example, residual drug composition on the stent frame due to incomplete removal, and dripping and/or uneven volume within an opening because of gravitational effects, as the tubular stent is rotated during the filing process. Another limitation is the lack of continuous control on drug load and the kinetics of its release with the difficulty or even lack of possibility to achieve adequate doses and adequate release kinetics simultaneously for different drugs.

Accordingly, there is a need in the art for a drug delivery stent and fabrication method that overcomes one or more of the above-cited disadvantages in the art.

SUMMARY OF THE INVENTION

It is, therefore, an object of the present invention to provide a stent fabrication method which can produce drug-filled stents with relatively intricate and/or delicate designs. It is also an object of the present invention to provide a stent fabrication method which can produce stents coated only on discrete and preferred portions of the stent.

The general fabrication method involves first creating a flat version of the desired stent pattern from a piece of thin sheet metal. The flat pattern can be produced through any suitable technique, such as etching the design into the sheet metal, or by cutting with a very fine laser or by any other technique. The stent pattern then may be polished, mechanically and/or electrochemically.

Once the sheet metal has been cut, it is deformed so as to cause its edges to meet. To create a cylindrical stent from a flat, roughly rectangular metal pattern, the flat metal is rolled until the edges meet. The locations where edges meet are joined together, such as by welding.

It is an object of this invention to provide a method of fabricating a coated stent comprising the steps of:
- cutting a plurality of stent patterns into a flat sheet of metal, each of said stent patterns comprising a plurality of discrete portions, a luminal surface, a vessel wall surface, a first long side, and a second long side;
- coating said discrete portions on a surface of each stent pattern with a composition to form a coated stent pattern;
- folding said coated stent pattern into a tubular shape so that said first and second long sides meet; and
- attaching said first and second long sides to form a coated stent.

It is another object of this invention to provide a method of fabricating a filled stent comprising the steps of:
- cutting a plurality of stent patterns into a flat sheet of metal, each of said stent patterns comprising stent members containing reservoirs, and first and second long sides;
- filling said reservoirs with a composition;
- folding said filled stent pattern into a tubular shape so that said first and second long sides meet; and
- attaching said first and second long sides to form a filled stent.

It is another object of this invention to provide a method of fabricating a drug-eluting stent comprising the steps of:
a) providing a plurality of stent patterns including one or more reservoirs into a flat piece of metal, each of the patterns having a first long side and a second long side, the first long side provided with a plurality of pairs of engagement points, the second long side provided with a plurality of pairs of engagement points, the plurality of pairs of engagement points disposed substantially opposite each other, the engagement points sized and disposed to communicate when the stent pattern is deformed and rolled into a tubular shape, each pair of the first long side engagement points provided with a bridge disposed between each first long side engagement point comprising the pair, the bridge having a width that is less than the width of the other portions of the stent pattern;
b) filling the one or more reservoirs with a composition comprising a therapeutic agent;
c) disposing a mandrel having a substantially cylindrical external surface and a longitudinal axis between the first long side and the second long side of the sheet, the longitudinal axis substantially parallel to the first long side and the second long side;
d) deforming the filled stent pattern into a tubular shape so that the first long side pairs of engagement points contact the second long side pairs of engagement points;
e) cutting the bridge; and
f) attaching each of the engagement points to the engagement point with which it is in contact to form the expandable filled stent.

It is another object of this invention to provide a method of fabricating a drug-eluting stent comprising the steps of:
a) providing a plurality of stent patterns including a plurality of reservoirs in a flat sheet of metal; each of the patterns having a first long side and a second long side, the first long side provided with a plurality of pairs of engagement points, the second long side provided with a plurality of pairs of engagement points, the plurality of pairs of engagement points disposed substantially opposite each other, the engagement points sized and disposed to communicate when the pattern is deformed and rolled into a tubular shape, each pair of the first long side engagement points provided with a bridge disposed between each first long side engagement point comprising the pair, the bridge having a width that is less than the width of the other portions of the stent;
b) electropolishing the flat stent pattern;
c) filling the reservoirs with a composition comprising a therapeutic agent;
d) disposing a mandrel having a substantially cylindrical external surface and a longitudinal axis between the first long side and the second long side of the sheet, the longitudinal axis substantially parallel to the first and the second long sides;
e) deforming the filled stent pattern into a tubular shape so that the first long side pairs of engagement points contact the second long side pairs of engagement points and allowing a portion of the stent pattern to remain attached to the sheet of metal;
f) cutting the bridge;
g) attaching each of the engagement points to the engagement point with which it is in contact to form the filled stent; and
h) disconnecting the filled stent from the sheet.

It is another object of this invention to provide a method of fabricating a drug-eluting stent comprising the steps of:
a) providing a plurality of stent patterns in a flat sheet of metal; each of the patterns having a first long side and a second long side, the first long side provided with a plurality of pairs of engagement points, the second long side provided with a plurality of pairs of engagement points, the plurality of pairs of engagement points disposed substantially opposite each other, the engagement points sized and disposed to communicate when the pattern is deformed and rolled into a tubular shape, each pair of the first long side engagement points provided with a bridge disposed between each first long side engagement point comprising the pair, the bridge having a width that is less than the width of the other portions of the stent;
b) electropolishing the flat stent pattern;
c) coating discrete portions of the flat stent pattern with a composition comprising a therapeutic agent to form a discrete-coated stent pattern;
d) deforming the discrete-coated stent pattern into a tubular shape so that the first long side pairs of engagement points contact the second long side pairs of engagement points and allowing a portion of the stent pattern to remain attached to the sheet of metal;
e) cutting the bridge;
f) attaching each of the engagement points to the engagement point with which it is in contact to form the discrete-coated stent; and
g) disconnecting the discrete-coated stent from the sheet.

It is yet another object of this invention to provide a drug-eluting stent according to one of the methods of the invention.

It is yet another object of this invention to provide a sheet for fabricating a drug-filled stent having a longitudinal lumen comprising:
a flat piece of sheet metal provided with a plurality of stent patterns including a plurality of reservoirs, each of the patterns having a first long side and a second long side, the first long side provided with a plurality of pairs of engagement points, the second long side provided with a plurality of pairs of engagement points, the plurality of pairs of engagement points disposed substantially opposite each other, the engagement points sized and disposed to communicate when the pattern is deformed and rolled into a tubular shape, each pair of the first long side engagement points provided with a bridge disposed between each first long side engagement point comprising the pair, the bridge having a width that is less than the width of the other portions of the stent.

It is yet another object of this invention to provide a method of coating the base material of a stent in the form of a flat sheet with multiple stent patterns or a single stent pattern. The coating may be a polymer and/or one or more drugs and may be applied prior to assembly of the stent pattern into a cylindrical shape, and may coat all or a portion of the stent pattern. Particular examples of appropriate drugs include, but are not limited to, rapamycin or analogs thereof, paclitaxel, and a number of other drugs addressed hereinafter.

It is another object of the invention to provide a method of coating a flat sheet with multiple stent patterns or a single stent pattern on discrete portions of the stent pattern, for example on non-bending or non-deforming portions of the stent, prior to forming the stent pattern into a cylindrical shape. The coating is typically applied to the flat sheet after one or multiple stent patterns are formed in the flat sheet. However, the discrete-coating may also be applied before cutting the stent pattern. It also is an object of the invention to provide a batch of discrete-coated stents fabricated from a plurality stent patterns cut into a flat metal sheet, where the discrete coating is applied prior to forming the flat stent patterns into tubular shapes. The coating may be applied to discrete portions in a highly accurate, consistent and efficient manner, using a predetermined map of the distribution of discrete portions based on the stent pattern tool used for forming the stent pattern. The method permits coating discrete portions on multiple flat stent patterns simultaneously. The method also permits coating discrete portions on both sides of the stent pattern, and differential coating—that is to say different coating on the luminal and the ab-luminal sides of the stent pattern.

The coating is typically applied to the flat sheet after a stent pattern or multiple stent patterns are formed on the flat sheet. Electropolishing may be carried out before the coating process. Alternatively, electropolishing may be eliminated from the process. For example, if the coating provides enough protection to the metal stent to make electropolishing unnecessary for achieving the desired biocompatibility, the electropolishing step can be eliminated.

It is yet another object of the invention to provide a stent fabrication method that can produce one or more expandable drug delivery stents, each having a stent pattern that includes reservoirs, where the reservoirs are filled with one or more compositions before the stent pattern is transformed from a flat sheet into a tubular shape. The reservoirs may be located on struts, and the struts having reservoirs may contain one or more reservoirs.

It is another object of the invention to provide an expandable drug delivery stent, where the stent is fabricated from a stent pattern cut into a flat sheet, where the stent pattern includes a plurality of reservoirs, and the reservoirs are filled with a composition prior to transforming into a tubular shape. The flat stent pattern can be produced through any suitable technique, such as etching the design into the sheet metal, or by cutting with a fine laser, or by any other technique known in the art. It also is an object of the invention to provide a batch of filled stents fabricated from a plurality stent patterns cut into a flat metal sheet, where each stent pattern includes a plurality of reservoirs, and the reservoirs are filled with one or more compositions prior to transforming the flat stent patterns into stents (tubular shapes).

It is yet another object of the invention to provide a method of flat-filling the reservoirs of multiple stent patterns or a single stent pattern with a composition. The reservoirs are filled with the composition prior to assembly of the stent into its tubular shape. The reservoirs may be filled in a highly accurate, consistent and efficient manner, with negligible waste of the composition, using a predetermined pattern (or map) of deposits based on the reservoir distribution in the stent pattern. The method of flat-filling permits the reservoirs of multiple flat stent patterns to be filled simultaneously.

It is a further object of the invention to provide a drug delivery stent having a stent pattern that includes a plurality of reservoirs, where more than one composition is deposited into the reservoirs before the stent pattern is transformed from a flat configuration into a tubular shape. For example, a first subset of reservoirs may be filled with a first composition and a second subset of reservoirs may be filled with a second composition. To create a tubular stent from a flat, roughly rectangular metal pattern, the flat metal is folded or rolled until the longitudinal edges are in contact. The contact points are then joined together, for example by welding.

The method for fabricating a filled stent further permits differential drug delivery, either by filling from one side two different compositions, or—if the order of filling layers of compositions is important—from both sides of the flat sheet. For example, the vessel wall side and luminal side of the stent pattern may be designed to release different therapeutic agents or combinations of therapeutic agents, or different therapeutic agents may be released at different times by layering release-modifying compositions or layering compositions containing therapeutic agent(s) separated by one or more layers of composition without therapeutic agent.

Thus, it is still further an object of the invention to provide a method of fabricating a drug delivery stent, where the stent is fabricated from a stent pattern cut into a flat metal sheet having a first and second major surface, where the stent pattern includes a plurality of reservoirs, each reservoir containing more than one composition, where the compositions are differentially deposited into the reservoirs from the first and second major surfaces of the flat sheet before the stent pattern is transformed into a tubular shape.

BRIEF DESCRIPTION OF THE DRAWINGS

The file of this patent contains at least one drawing executed in color. Copies of this patent or patent application publication with color drawing(s) will be provided by the Office upon request and payment of the necessary fee.

The present invention may be understood and appreciated more fully from the following detailed description taken in conjunction with the drawings in which:

FIGS. 2A, 2B and 2C are illustrations of three alternative stent patterns to be etched, in accordance with the method of FIGS. 1A, 1C and 1D, into a flat sheet of metal;

FIG. 34 shows an alternative embodiment of an apparatus constructed in accordance with the invention;

FIG. 35 is a top view of FIG. 34;

FIG. 36 shows a means for deforming a stent made in accordance with the embodiment shown in FIGS. 34 and 35;

FIG. 37 is a side view of the deforming means shown in FIG. 36;

FIG. 58A shows discrete-coated portions on the finished stent with sides attached as in FIG. 5; FIG. 58B shows discrete-coated portions on the flat stent pattern shown in FIG. 14; FIG. 58C shows discrete-coated portions on the flat stent pattern shown in FIG. 48A.

FIG. 59A illustrates discrete coating spots of two different shapes; FIG. 59B illustrates discrete coating spots at higher magnification.

DETAILED DESCRIPTION OF THE INVENTION

The present invention provides a method of fabricating an expandable drug-eluting stent from a flat sheet having reservoirs, by filling the reservoirs with a composition prior to transforming the flat-filled stent pattern into a tubular shape. The term "expandable" is meant to include "balloon-expandable" and "self-expanding". Also provided is a method of fabricating an expandable drug-eluting stent that is coated with a composition on discrete portions or spots prior to transforming the flat-coated stent pattern into a tubular shape.

The invention is discussed and explained below with reference to the accompanying drawings. Note that the drawings are provided as an exemplary understanding of the invention and to schematically illustrate particular embodiments and details of the invention. The skilled artisan will readily recognize other similar examples equally within the scope of the invention. The drawings are not intended to limit the scope of the invention as defined in the appended claims.

Figure 1A:
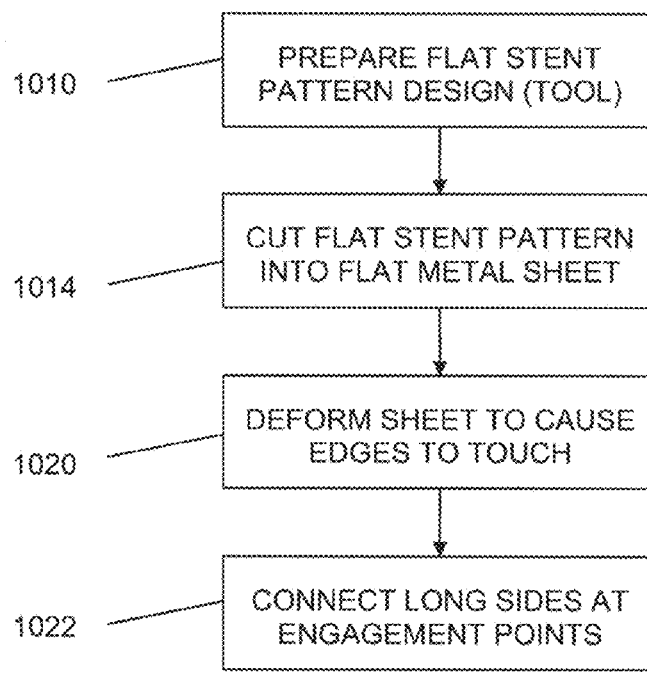
FIG. 1A is a flow chart illustration of the stent fabrication method of the invention.

Reference is now made to FIG. 1A, which illustrates a method of fabricating a stent from a flat sheet and to FIGS. 2A, 2B, 2C, 3 and 4 which are useful in understanding the method of FIG. 1A.

In the stent fabrication method of the present invention, a stent designer first prepares a drawing of the desired stent pattern in a flat format (step 1010 of FIG. 1A).

Figure 2C:
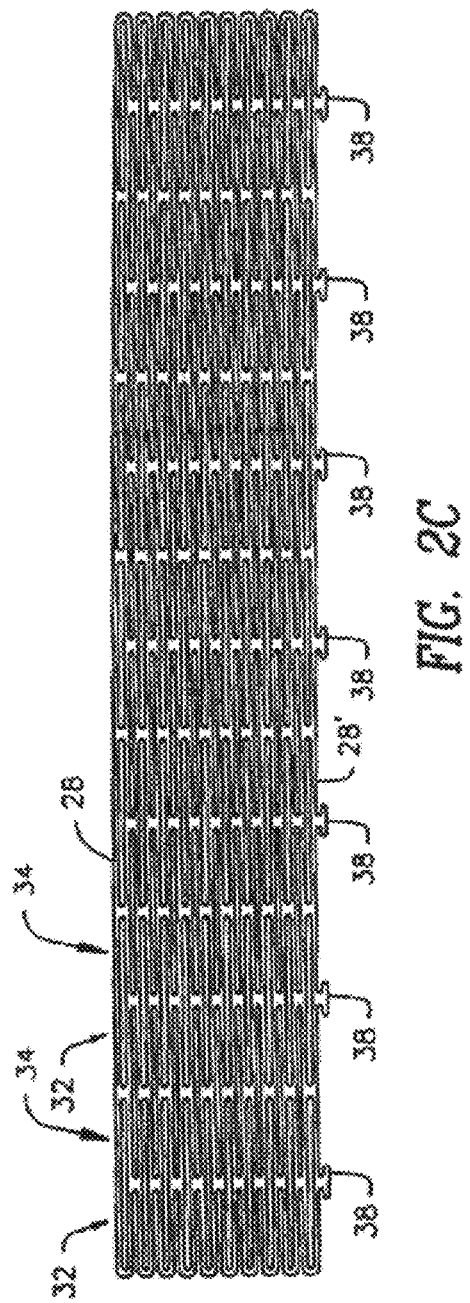

FIGS. 2A, 2B and 2C illustrate three exemplary stent pattern designs, which may include drug reservoirs (not shown). The pattern of FIG. 2A has two types of sections 20 and 22. Each section 20 has two opposing periodic patterns and each section 22 has a plurality of connecting lines 24. The pattern of FIG. 2A can be formed of any size; a preferable size is to have each section 20 be between 1 and 6 mm wide and each section 22 have connecting lines 24 of 1-6 mm long. At such sizes, the pattern of FIG. 2A cannot be cut using a laser cutting system.

The pattern of FIG. 2B is similar to that of FIG. 2A in that it also has sections 20 of opposing periodic patterns. The pattern of FIG. 2B also has connecting sections, labeled 30, which have a Z shape.

The pattern of FIG. 2C has no connecting sections. Instead, it has a series of alternating patterns, labeled 32 and 34.

The patterns of FIGS. 2A, 2B and 2C optionally also have a plurality of small protrusions 38 which are useful in forming the stent, as described hereinbelow.

Returning to FIG. 1A, in step 1014, the stent pattern is cut into a flat piece of metal ("sheet metal"). The metal can be any type of biocompatible material, such as stainless steel, or a material which is plated with a biocompatible material. The cutting operation can be implemented in any of a number of ways, such as by etching, or by cutting with a fine cutting tool, or by cutting with a very fine laser, should one become commercially available.

If step 1014 is implemented with etching, then, the process is designed to cut through the sheet metal. This process is known; however, for the purposes of completeness, it will be briefly described hereinbelow.

The drawing of the pattern, or tool, is reduced and printed onto a transparent film. As it is desired to cut completely through the sheet metal, the drawing is printed onto two films which may be joined together in a few places along their edges. The sheet metal is covered, on both sides, with a layer of photoresist and placed between the two transparent, printed films. The structure is illuminated on both sides which causes the portions of the photoresist which receive the light to change properties.

The sheet metal is placed into development bath, which removes those portions of the photoresist with changed properties. The sheet metal is then placed into an etching solution which etches away all material on which there is no photoresist-removing solution which removes the photoresist (which are all the empty spaces in the pattern, as illustrated, for example, spaces 26 of the stent pattern of FIGS. 2A and 2B, and 790 in the stent pattern of FIG. 52), leaving the metal having the desired stent pattern.

Figure 5B:
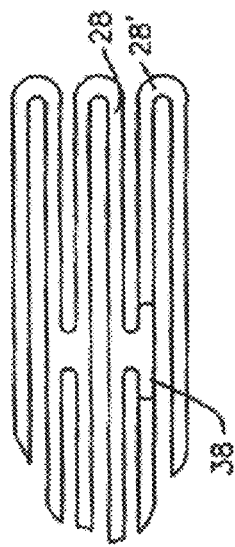
FIGS. 5A and 5B are side and top view illustrations, respectively, of one connection location of the stent of FIG. 4.
Figure 5A:
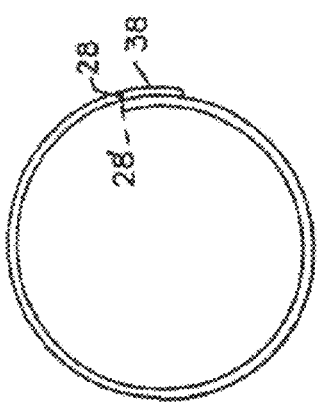
Figure 3:
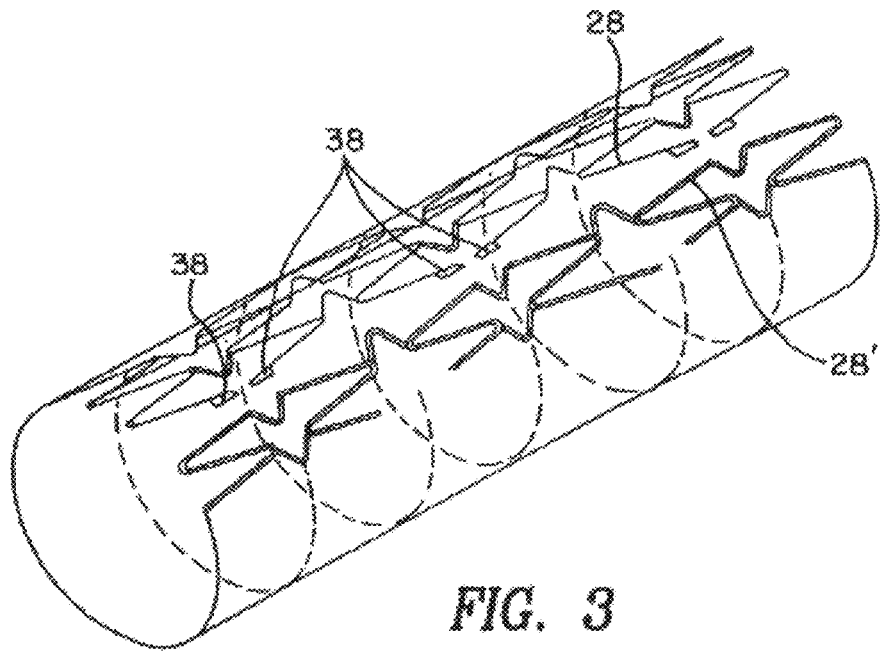
FIG. 3 is an isometric illustration of a stent pattern being transformed into a tubular shape, useful in understanding the method of FIG. 1A.

In step 1020, the metal pattern is deformed so as to cause its long sides, or longitudinal edges (labeled 28, 28' in FIGS. 2A, 2B and 2C) to meet each other. FIG. 3 illustrates the deformation process. For cylindrical stents, the deformation process is a rolling process, as shown. For ease of illustration, the stent patterns in FIGS. 3, 4, 5A and 5B are shown without reservoirs. If the protrusions 38 have been produced, they protrude beyond the edge 28 to which they are attached, as illustrated in FIGS. 2A and 2B. After deformation of the stent pattern, the protrusions 38 protrude over the edge 28' to which they are not attached, as illustrated in FIG. 5A.

Figure 4:
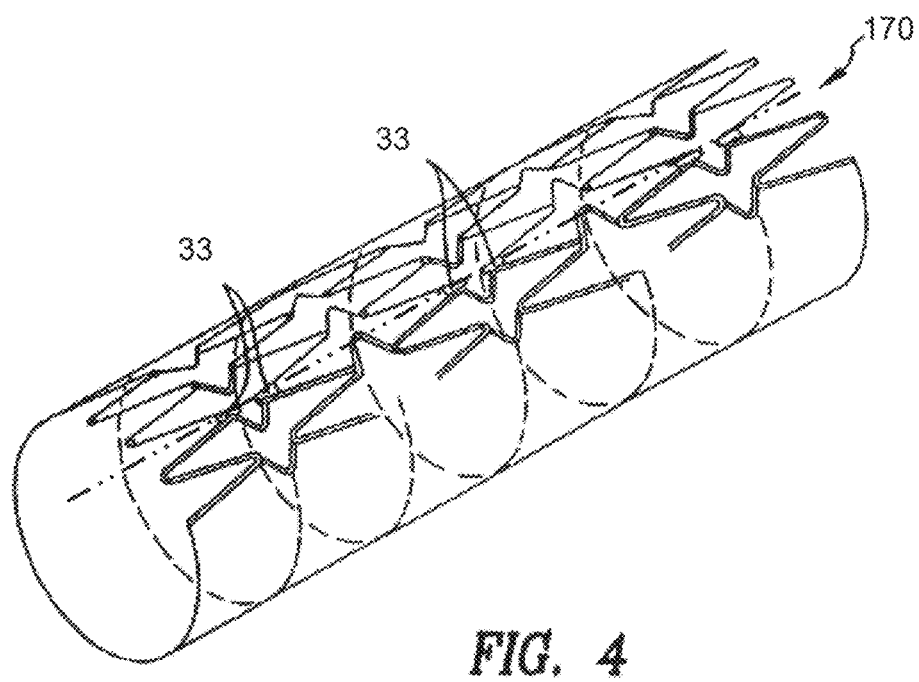
FIG. 4 is an isometric illustration of a stent formed from the method of FIG. 1A.

In step 1022, the longitudinal edges 28, 28' are joined together by any suitable process, such as spot welding. The edges 28, 28' can be brought together and joined in the appropriate places, e.g., at corresponding engagement points to form weld points 33 along a weld line 170, as illustrated in FIG. 4. If the protrusions 38 were made, the protrusions 38 are joined to the opposite edge 28', either by welding, adhesive or other means known in the art. FIG. 5B illustrates the connection of a protrusion 38 to the opposite edge 28'.

FIG. 4 illustrates a stent 31 formed by the process of steps 1010-1022. It is noted that such a stent has connection points 32 formed by the joining of the points 30.

Finally, the stent 31 may be polished to remove any excess material not properly removed by the cutting process (step 1014). In some embodiments, the polishing is performed before the flat sheet is deformed into a tubular stent. The polishing can be performed mechanically, by rubbing a polishing stick having diamond dust on its outside/inside of the stent 31. Alternatively, an electropolishing unit can be utilized.

Figure 7:
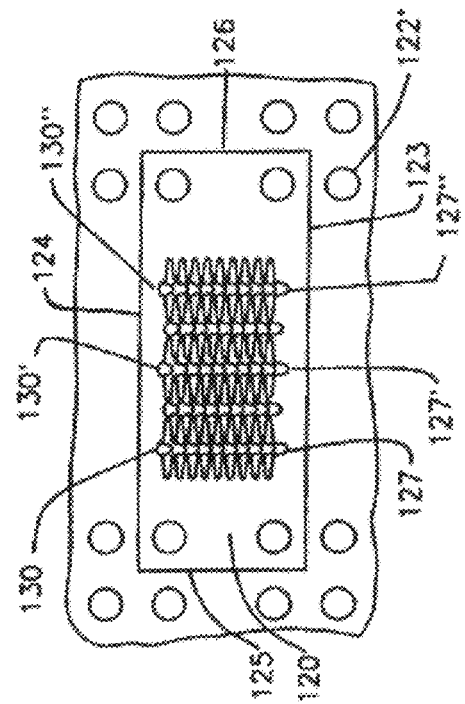
FIG. 7 shows a detailed view of one of the patterns shown in FIG. 6.
Figure 6:
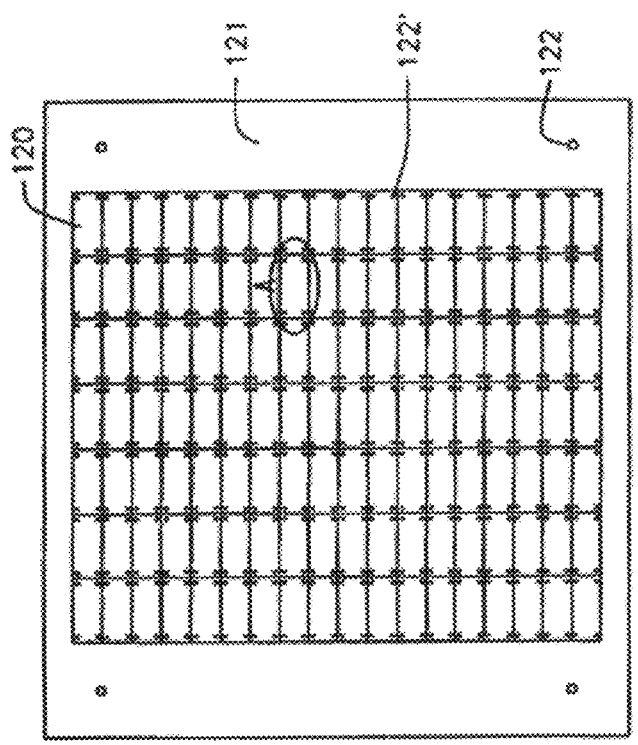
FIG. 6 shows a piece of sheet metal with a plurality of stent patterns made in accordance with the invention.

FIG. 6 shows an alternative embodiment of the invention in which a plurality of patterns 120 are etched and cut into the sheet metal 121 as previously discussed. FIG. 7 is an enlarged view of one of the plurality of patterns 120 shown in FIG. 6.

Figure 8:
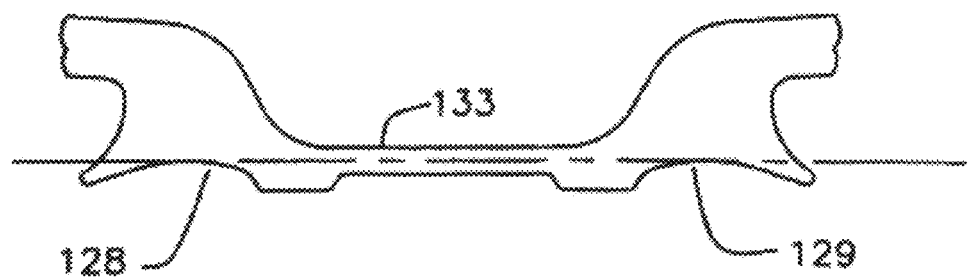
FIG. 8 shows a detailed view of a pair of engagement troughs shown in FIG. 8.
Figure 9:
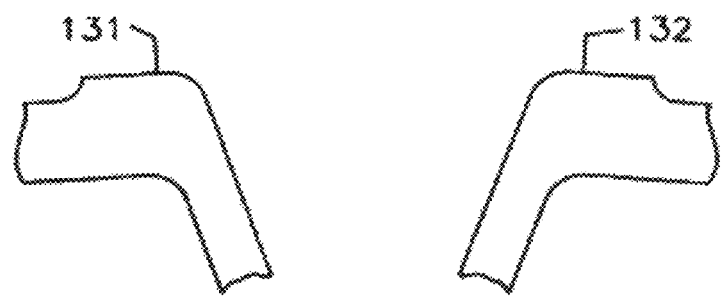
FIG. 9 shows a detailed view of a pair of engagement protrusions shown in FIG. 7.

The sheet metal 121 and each of the patterns 120 is provided with a plurality of alignment apertures 122 and 122' adapted to receive sprockets (not shown) for precisely moving and maintaining the precise alignment of the sheet metal 121 and the patterns 120 during the various stages of manufacturing. Each pattern 120 has a first long side 123 and a second long side 124, a first short side 125, and a second short side 126. The first long side 123 is provided with a plurality of pairs 127, 127' and 127" of engagement troughs 128 and 129 (shown in greater detail in FIG. 8). FIG. 8 is an enlarged view of one pair 127 of the plurality of engagement troughs 128 and 129 shown in FIG. 7. Each pair 127, 127' and 127" of engagement troughs has a first engagement trough 128 and a second engagement trough 129. The second long side 124 is provided with a plurality of pairs 130, 130' and 130" of engagement protrusions (shown in greater detail in FIG. 9). FIG. 9 is an enlarged view of one pair 130 of the plurality of engagement protrusions 131 and 132 shown in FIG. 7. Each pair 130, 130' and 130" of engagement protrusions is provided with a first engagement protrusion 131 and a second engagement protrusion 132. The pairs of engagement protrusions 130, 130' and 130" are disposed substantially opposite the pairs of engagement troughs 127, 127' and 127".

Figure 10:
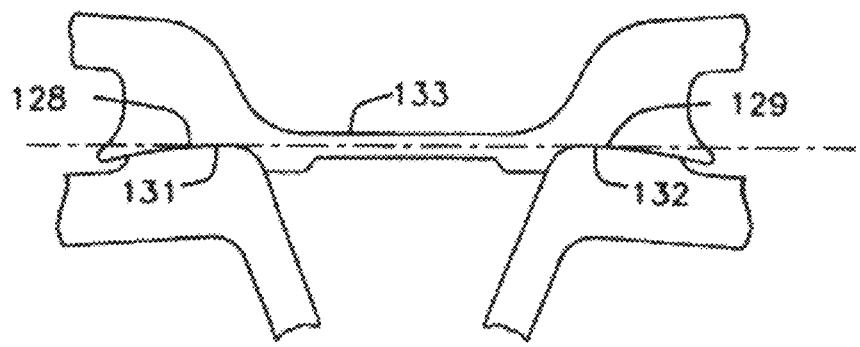
FIG. 10 shows the engagement troughs and engagement protrusions of FIGS. 9 and 10 in the engaged position.
Figure 17:
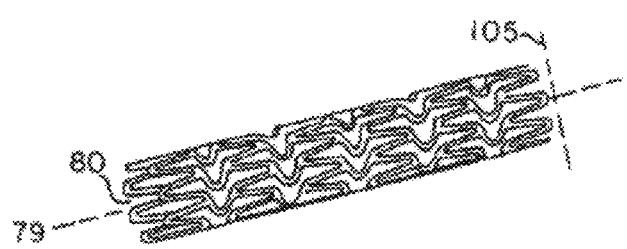
FIG. 17 is a perspective view of a stent constructed in accordance with this invention.

The engagement troughs 128 and 129 are disposed and adapted to receive and engage the engagement protrusions 131 and 132 so that the alignment of the stent is maintained when the pattern 120 is deformed and the flat sheet metal is rolled so that the first long, side 123 and the second long side 124 meet each other, as shown in FIG. 10, to form a tube as shown, for example, in FIG. 17.

A bridge 133 of material is disposed between each pair 127, 127' and 127" of engagement troughs 128 and 129. This bridge 133 imparts additional stability and facilitates alignment during manufacturing and imparts additional strength to the welds of the finished stent as discussed below.

Figure 11:
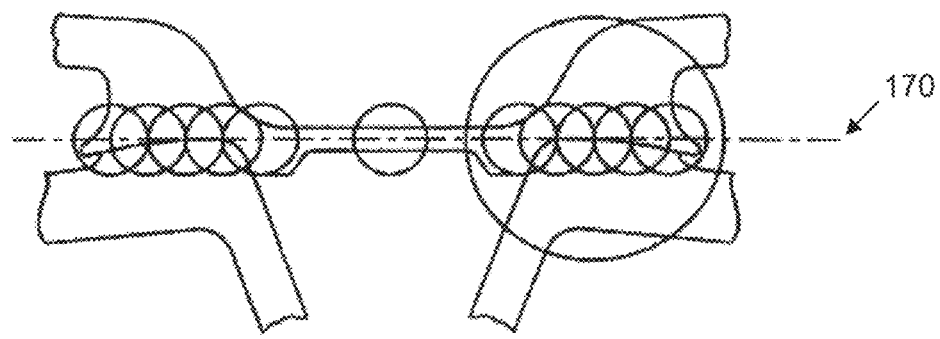
FIG. 11 shows a welding run practiced in accordance with the invention.
Figure 12:
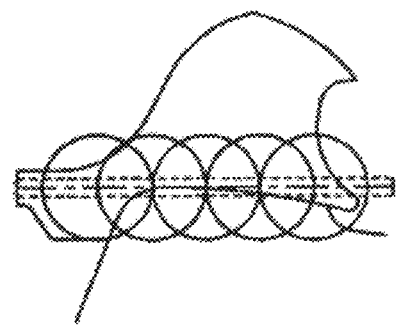
FIG. 12 is a detailed view of the welding run shown in FIG. 11.

After the sheet has been rolled into a tubular stent and the engagement troughs 128 and 129 have received the engagement protrusions 131 and 132, means (not shown) are utilized to maintain the alignment and the bridge 133 is cut to leave two substantially equal parts. The bridge 133 may be cut in a variety of ways well known to those skilled in the art. In one embodiment, a laser is utilized. The first engagement trough 128 is welded to the first engagement protrusion 131 and the second engagement trough 129 is welded to the second engagement protrusion 132 along a weld line 170, as shown in FIGS. 11 and 12. This may be accomplished in a variety of ways well known to those skilled in the art. In one embodiment, about five spot welds are used in each weld run, as shown in FIGS. 11 and 12. The heat produced by the welding melts the cut bridge 133 material and the material is drawn towards the engagement trough 128 or 129 to which the material is attached and is drawn into the welded area between the engagement trough and the engagement protrusion where the additional bridge material becomes part of and imparts additional strength to the weld. The stent may then be finished as previously discussed.

FIG. 12 is an enlarged view of the welded area shown in FIG. 11. In one embodiment, the weld run is offset from the point where the engagement trough and the engagement protrusion contact each other. For example, the weld run may be offset about 0.01 mm.

Figure 13:
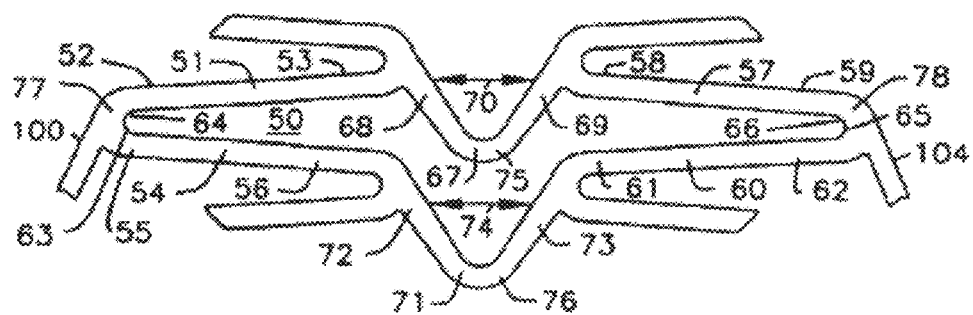
FIG. 13 is a detailed view of a cell of a stent made in accordance with this invention.

FIG. 13 is a detailed view of the pattern shown in FIG. 7. As shown in FIGS. 13 and 17, Applicants' invention can also be described as an expandable stent defining a longitudinal lumen 80 having a longitudinal axis or extension 79 and a circumferential axis or extension 105, including a plurality of flexible connected cells 50 with each of the flexible cells 50 having a first longitudinal end 77 and a second longitudinal end 78. Each cell 50 also is provided with a first longitudinal apex 100 disposed at the first longitudinal end 77 and a second longitudinal apex 104 disposed at the second longitudinal end 78. Each cell 50 also includes a first member 51 having a longitudinal component having a first end 52 and a second end 53; a second member 54 having a longitudinal component having a first end 55 and a second end 56; a third member 57 having a longitudinal component having a first end 58 and a second end 59; and a fourth member 60 having a longitudinal component having a first end 61 and a second end 62. The stent also includes a first loop 63 defining a first angle 64 disposed between the first end 52 of the first member 51 and the first end 55 of the second member 54. A second loop 65 defining a second angle 66 is disposed between the second end 59 of the third member 57 and the second end 62 of the fourth member 60 and is disposed generally opposite to the first loop 63. A first flexible compensating member or flexible link 67 having a first end 68 and a second end 69 is disposed between the first member 51 and the third member 57 with the first end 68 of the first flexible compensating member or flexible link 67 communicating with the second end 53 of the first member 51 and the second end 69 of the first flexible compensating member or flexible link 67 communicating with the first end 58 of the third member 57. The first end 68 and the second end 69 are disposed a variable longitudinal distance 70 from each other. A second flexible compensating member 71 having a first end 72 and a second end 73 is disposed between the second member 54 and the fourth member 60. The first end 72 of the second flexible compensating member or flexible link 71 communicates with the second end 56 of the second member 54 and the second end 73 of the second flexible compensating member or flexible link 71 communicates with the first end 61 of the fourth member 60. The first end 72 and the second end 73 are disposed a variable longitudinal distance 74 from each other.

In one embodiment, the first and second flexible compensating member or flexible links 67 and 71 are arcuate. The first and second flexible compensating member or flexible links 67 and 71 are differentially extendable or compressible when the stent is bent in a curved direction away from the longitudinal axis 79 of the lumen 80 (shown in FIG. 17). The first member 51, second member 54, third member 57, and fourth member 60 and the first loop 63 and the second loop 65 and the first flexible compensating member or flexible link 67 and the second flexible compensating member or flexible link 71 are disposed so that as the stent is expanded the distance between the first flexible compensating member or flexible link 67 and the second flexible compensating member or flexible link 71 increases and the longitudinal component of the first member 51, second member 54, third member 57 and fourth member 60 decreases while the first loop 63 and the second loop 65 remain generally opposite to one another, the ends 68 and 69 of the first flexible compensating member or flexible link 67 and the ends 72 and 73 of the second flexible compensating member or flexible link 71 open so as to increase the variable longitudinal distance 70 between the first end 68 and the second end 69 of the first flexible compensating member or flexible link 67 and so as to increase the variable longitudinal distance 74 between the first end 72 and the second end 73 of the second flexible compensating member or flexible link 71. This compensates for the decreasing of the longitudinal component of the first member 51, second member 54, third member 57, and fourth member 60 and substantially lessens the foreshortening of the stent upon its expansion. Upon expansion, the first flexible compensating member 67 and the second flexible compensating member 71 impart support to the lumen being treated. Reservoirs may be located on first members 51, second members 54, third members 57, fourth members 60, non-flexing portions of first flexible compensating members 67, and/or non-flexing portions of second flexible compensating members 71.

Figure 14:
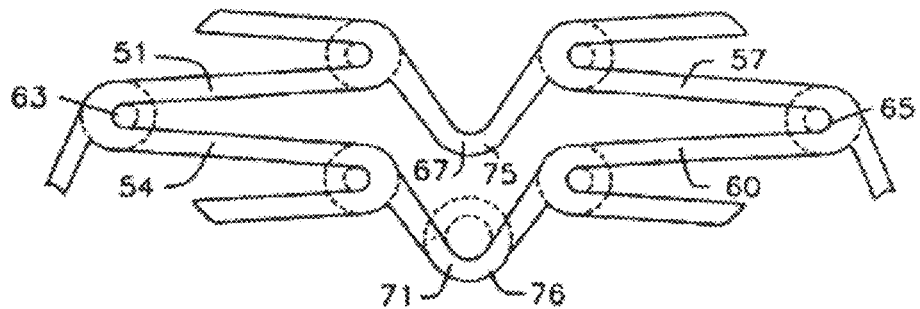
FIG. 14 is a detailed view of a cell made in accordance with this invention.

FIG. 14 shows the dimensions of an embodiment of a flat stent pattern in accordance with the invention. The deflection points, i.e., the first and second loops 63 and 65 and the first and second compensating members 67 and 71, are made wider than the first, second, third, and fourth members 51, 54, 57 and 60 so that the force of the deflection is distributed over a wider area upon the expansion of the stent. The deflection points can be made wider than the first, second, third and fourth members in differing amounts so that the deflection will occur in the narrower areas first due to the decreased resistance. In one embodiment, the first and second compensating members are wider than the first, second, third and fourth members and the first and second loops are wider than the first and second compensating members. One of the advantages of sizing the first and second loops so that they are wider than the first and second compensating members is that the stent will substantially compensate for foreshortening as the stent is expanded. In the embodiment shown in FIG. 14, the first, second, third and fourth members 51, 54, 57 and 60 have a width of about 0.1 mm. The first and second loops 63 and 65 have a width of about 0.14 mm. The first and second compensating members 67 and 71 are provided with a thickened portion 75 and 76 having a width of about 0.12 mm. Thus, in this embodiment, the first and second loops have a width that is about 40% greater and the first and second compensating members have a width that is about 20% greater than the width of the first, second, third and fourth members.

Figure 15:
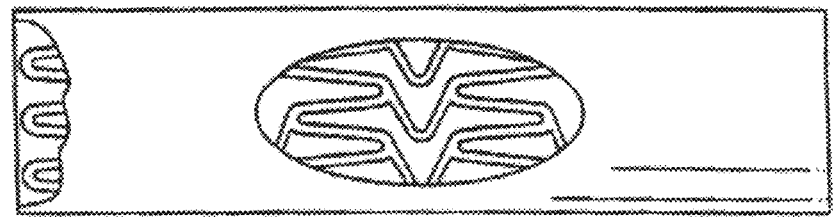
FIG. 15 shows a cell of a stent made in accordance with this invention.
Figure 16:
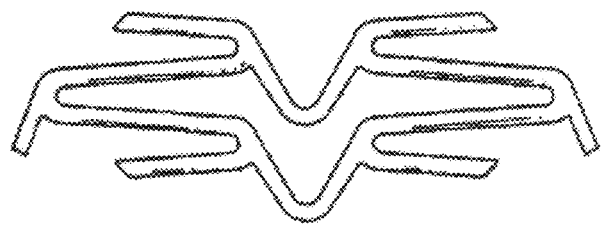
FIG. 16 is an enlarged view of the cell shown in FIG. 15.

FIGS. 15 through 17 show details of a stent constructed in accordance with the invention.

Yet another advantage of the invention is shown in FIGS. 18 to 21. In this embodiment, the stent patterns are adapted so that upon the expansion of the stent against the internal wall of a vessel substantially no portion of the stent projects into the longitudinal lumen of the stent. For the sake of clarity, the dimensions and the degree of displacement of the components of the stents shown in FIGS. 18 to 21 has been intentionally exaggerated.

Figure 18:
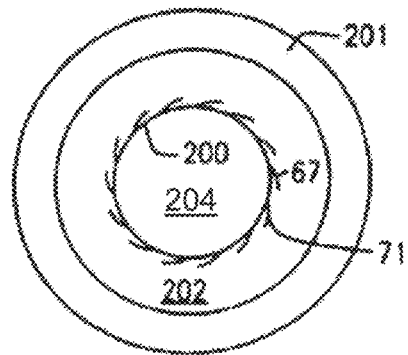
FIG. 18 is a cross-sectional front view of an unexpanded stent made in accordance with the invention.
Figure 19:
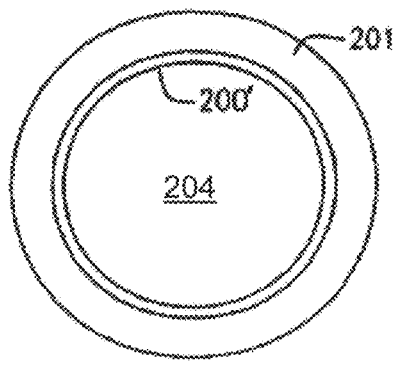
FIG. 19 is a cross-sectional front view of the stent shown in FIG. 18 after it has been expanded.

FIG. 18 is a cross-sectional front view taken along line A-A of the unexpanded stent made in accordance with the invention shown in FIG. 17. The unexpanded stent 200 of FIG. 18 is shown disposed in the lumen 202 of a blood vessel 201 prior to expansion. As previously discussed, this stent is made by first cutting the stent pattern into a flat piece of sheet metal and then rolling the sheet metal into a tube to form the tubular stent. As shown in FIG. 18 after rolling, the first and second flexible compensating members 67 and 71 of the unexpanded stent 200 tend to "flare out" in a direction away from the stent lumen 204. Thus, the flexible compensating members 67 and 71 define outer diameters which are larger than the outer diameters defined by the remaining portions of the stent. FIG. 19 shows the stent of FIG. 18 after it has been expanded in the lumen 202 and against the internal wall of the blood vessel 201. As shown in FIG. 19, upon expansion of the unexpanded stent toward the wall of the blood vessels, the walls of the blood vessel imparts a mechanical force to the first and second flexible compensating members 67 and 71 and the compensating members move toward the longitudinal axis or lumen of the expanded stent 200' until they are substantially in registry with the remaining portion of the stent. Thus, the lumen of the expanded stent 200' is substantially circular when viewed in cross section with substantially no portion of the expanded stent 200' projecting into the lumen 204 of the stent or towards the longitudinal axis of the expanded stent.

Figure 20:
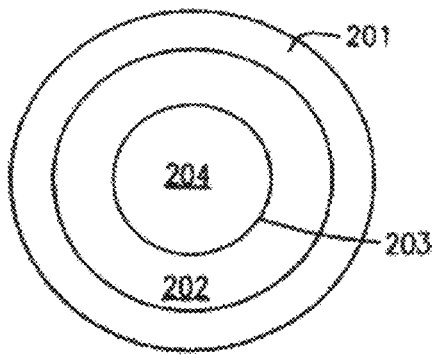
FIG. 20 is a cross-sectional front view of an unexpanded stent made by cutting a pattern in a tube.

FIG. 20 is similar to FIG. 18 except that the pattern has been cut into a tubular member using conventional methods of making stents. As shown in FIG. 20, the flexible compensating members do not flare out away from the longitudinal axis of the unexpanded stent 203 into the lumen 202 of the blood vessel 201. Upon the expansion of the stent shown in FIG. 20 toward the walls of the blood vessel 201, the flexible compensating members 67' and 71' tend to "flare in" and project into the lumen 204 of the expanded stent 203', as shown in FIG. 21.

Figure 21:
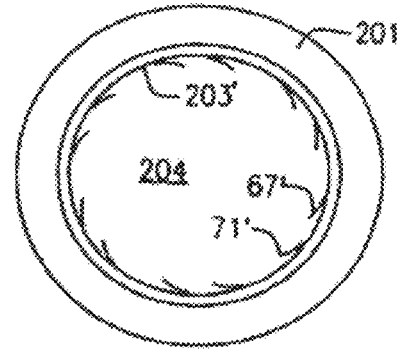
FIG. 21 is a cross-sectional front view of the stent shown in FIG. 20 after expansion.

FIG. 21 shows the stent 203 of FIG. 20 after it has been expanded in a lumen of a blood vessel 201. The flexible compensating members 67' and 71' are not in registry with the remaining portions of the stent and define a diameter smaller than the diameter of remaining portions of the stent. These projections into the lumen of the stent create turbulence in a fluid flowing through the longitudinal axis of the expanded stent and could result in clot formation.

An apparatus for fabricating a stent may include a platform, a mandrel, and means for deforming a sheet of metal around the mandrel, as described by way of example below.

The platform is adapted to receive a flat sheet of metal to be transformed into a stent. In one embodiment, the flat sheet of metal is provided with a first end, a second end defining a longitudinal axis, a first major surface, a second major surface, a first long side, a second long side, with the first and said second long sides substantially parallel to the longitudinal axis of the sheet. The mandrel has a substantially cylindrical external surface and a first end and a second end defining a longitudinal axis. The mandrel is sized to have a cross-sectional diameter substantially equal to or less than the internal diameter of a stent to be fabricated. A means for securing the mandrel against a major surface of the flat sheet of metal is provided. A means for deforming the flat sheet of metal around the external surface of the mandrel is also provided to deform the flat sheet of metal into a substantially tubular shape that substantially conforms to the external surface of the mandrel. In one embodiment, the means for deforming the sheet is adapted so that the first long side and the second long side remain substantially parallel to each other when the flat sheet of metal is deformed into a tubular shape. A means, e.g., a welding apparatus, laser, adhesive, or screw secures the first long side of the sheet to the second long side of the sheet.

In operation of one embodiment a plurality of stent patterns are cut or etched into a flat piece of metal. Each of the patterns has a first long side and a second long side, with the first long side provided with a plurality of pairs of engagement points and second long side provided with a plurality of pairs of engagement points. The plurality of pairs of engagement points are disposed substantially opposite each other and are sized and disposed to communicate when the pattern is deformed and rolled into a tubular shape. Each pair of the first long side engagement points is provided with a bridge disposed between each first long side engagement point comprising the pair, the bridge having a width that is less than the width of the other portions of the stent.

A mandrel is disposed between the first and second long sides of the sheet. The mandrel has a substantially cylindrical external surface and a longitudinal axis substantially parallel to the first long side and the second long sides. The pattern is deformed into a tubular shape so that the first long side pairs of engagement points contact the second long side pairs of engagement points.

The bridge is cut and each of the engagement points is attached to the engagement point with which it is in contact to form the expandable stent.

Figure 22:
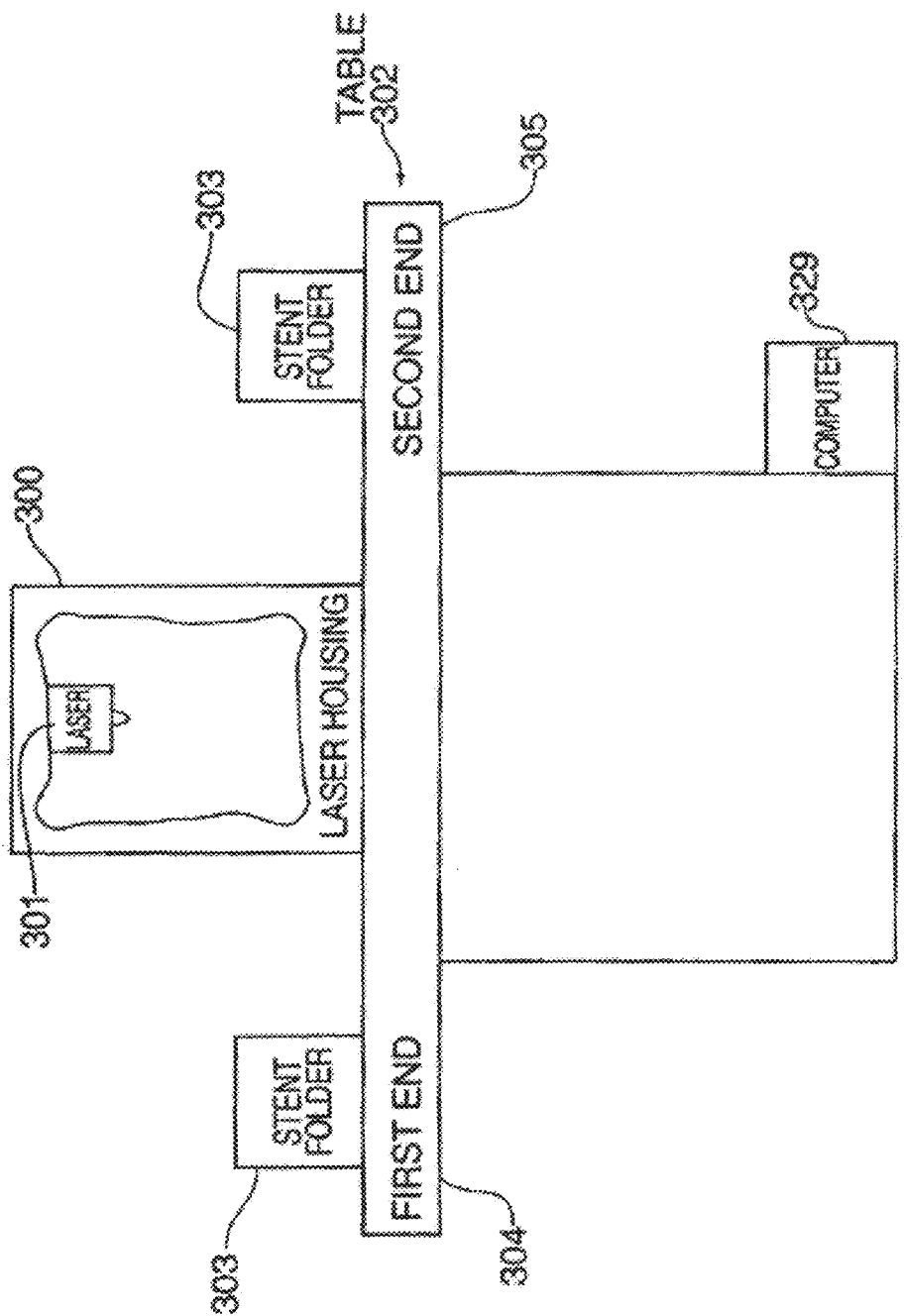
FIG. 22 shows an apparatus for folding a stent in accordance with the invention.
Figure 23:
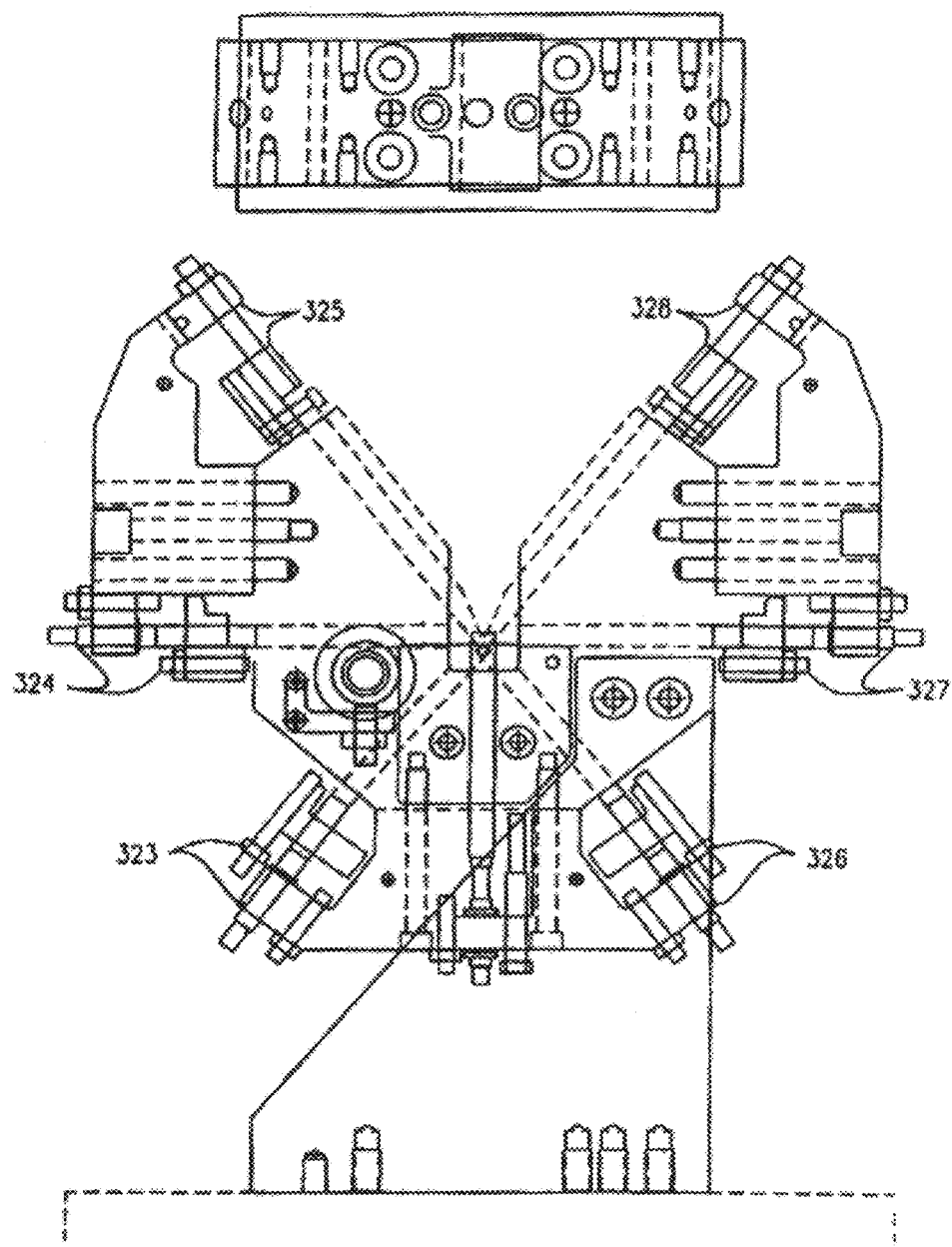
FIG. 23 shows an apparatus for folding a stent in accordance with the invention.
Figure 24:
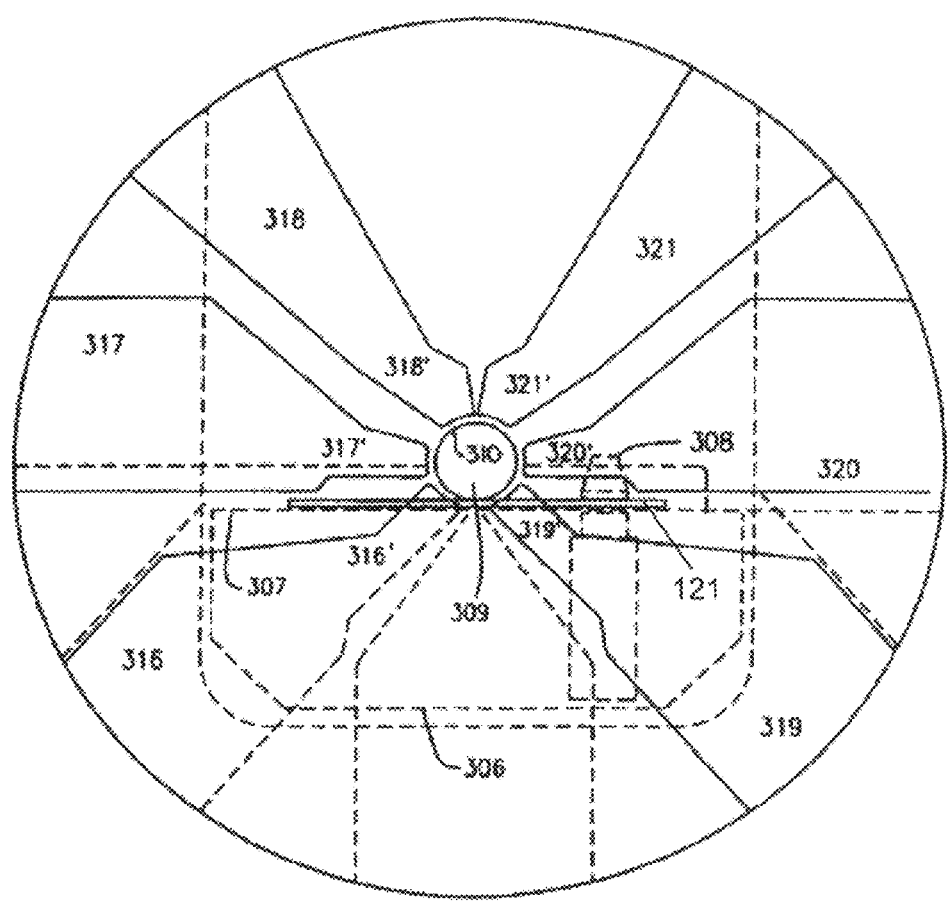
FIG. 24 is an enlarged view of a portion of the apparatus shown in FIG. 23.

FIGS. 22 to 24 show one embodiment of an apparatus for fabricating and a stent constructed in accordance with Applicants' invention. The apparatus comprises a laser housing 300, a laser 301, a movable table 302, and a plurality of stent folders 303 disposed on the table. The laser 301 is disposed within and selectively movable within the housing 300. The movable table 302 has a first end 304 and a second end 305 and is adapted for selective movement into and out of the laser housing 300. The table 302 is adapted so that when the first end 304 of the table 302 is disposed within the laser housing 300 the second end 305 of the table 302 is disposed outside of said housing 300 and when said second end 305 of the table 302 is disposed within the laser housing 300 the first end 304 of the table 302 is disposed outside of the laser housing 300.

A plurality of stent folders 303 is disposed at the first end 304 of the table and a plurality of stent folders 303 is disposed at the second end 305 of the table 302. As shown in FIGS. 23 and 24, each of said stent folders 303 comprises: a base 306 having a platform 307 adapted to receive a flat sheet of metal 121 containing a stent pattern to be formed into a stent; a plurality of alignment pins 308 that project from each of the platform 307; a mandrel 309; a hingedly connected arm; a plurality of deforming blades; and a plurality of motors attached to the deforming blades.

The flat sheet of metal containing a stent pattern has a longitudinal axis, a first major surface, a second major surface, a first long side, and a second long side, with the first and the second long sides substantially parallel to the longitudinal axis. The sheet 121 is also provided with a plurality of alignment apertures 122, 122', as illustrated in FIGS. 6 and 7. The alignment pins 308 are sized and disposed to engage the alignment apertures and align the sheet 121 on the platform 307.

Figure 32:
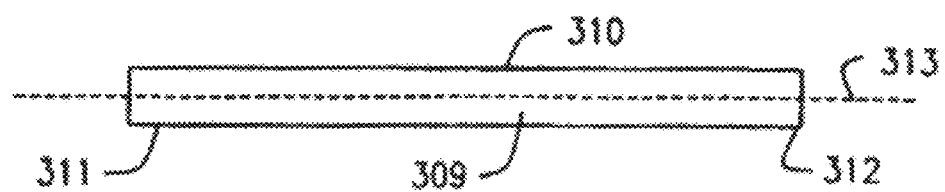
FIG. 32 shows a mandrel utilized in accordance with the invention.
Figure 33:
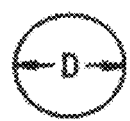
FIG. 33 shows a mandrel receiving surface made in accordance with the invention.
Figure 33:
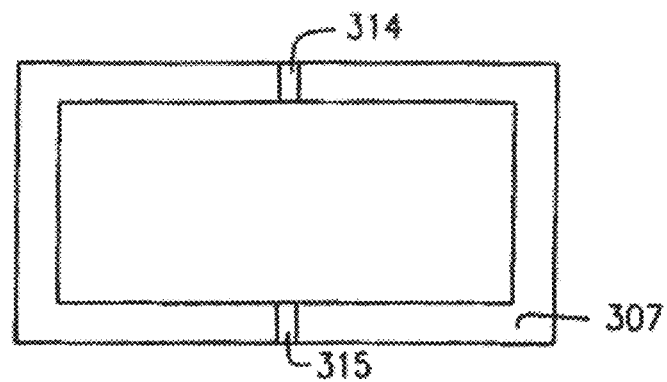

As shown in FIG. 32, the mandrel 309 may have a substantially cylindrical external surface 310, a first end 311, a second end 312, and a longitudinal axis 313. The mandrel 309 is sized to have a cross-sectional diameter (D) substantially equal to or less than the internal diameter of the stent to be fabricated. As shown in FIG. 33, the platform 307 is provided with a first concave recess 314 adapted to receive the first end 311 of the mandrel and a second concave recess adapted to receive the second end 312 of the mandrel 309. Referring again to FIG. 23, the hingedly connected arm is adapted for movement in a first direction toward the platform 307 and in a second direction away from the platform 307 for securing the mandrel 309 against a major surface of said flat sheet of metal when it is disposed on the platform 307.

Figure 29:
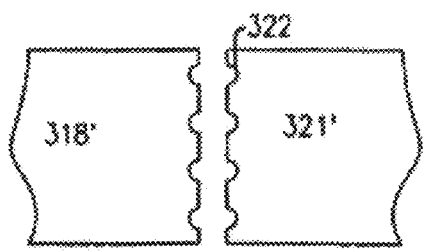
FIG. 29 shows details of two blade deforming tips.

As shown in FIG. 24, each stent folder 303 is provided with a first deforming blade 316 provided with a first deforming blade tip 316'; a second deforming blade 317 provided with a second deforming blade tip 317'; a third deforming blade 318 provided with a third deforming blade tip 318'; a fourth deforming blade 319 provided with a fourth deforming blade tip 319'; a fifth deforming blade 320 provided with a fifth deforming blade tip 320'; and a sixth deforming blade 321 provided with a sixth deforming blade tip 321'. The blades are disposed around the external surface 310 of the mandrel 309 and are adapted to deform the flat sheet of metal against the external surface 310 of the mandrel 309 so that the flat sheet of metal is deformed into a substantially tubular shape substantially conforming to the external surface 310 of the mandrel 309. The deforming blades are disposed between the first end 311 and the second end 312 of the mandrel 309. Each of the deforming blades is adapted for independent and selective movement in a first direction toward the mandrel 309 and a second direction away from the mandrel so as to selectively impinge the deforming blade tips 316', 317', 318', 319', 320' and 321' against the mandrel or against a portion of the sheet disposed between the mandrel and each of the deforming blade tips. Each of the deforming blades is also adapted so that the first long side and the second long side of the sheet remain substantially parallel to each other when the sheet is deformed into the tubular shape. The third and the sixth deforming blade tips 318' and 321' may be provided with a plurality of scalloped laser apertures 322, as shown in FIG. 29, which are sized and disposed to permit the third and the sixth deforming blade tips to secure the first long side and the second long side against the external surface of the mandrel while providing the laser access to predetermined portions of the first long side and the second long side in order to weld the first long side to the second long side.

As illustrated in FIG. 23, a first motor 323 is connected to the first deforming blade; a second motor 324 is connected to the second deforming blade; a third motor 325 is connected to the third deforming blade; a fourth motor 326 is connected to the fourth deforming blade; a fifth motor 327 is connected to the fifth deforming blade; and a sixth motor 328 is connected to the sixth deforming blade. Each of the motors is adapted for selectively moving each of the deforming blades to which it is connected in a first direction toward the mandrel and in a second direction away from the mandrel.

A computer 329 controls the sequence in which the first end 304 of the table 302 and the second end 305 of the table 302 are disposed within the laser housing 300; the sequence and degree to which each of the deforming blade tips impinges upon the mandrel or a portion of the sheet disposed between the mandrel and each of the deforming blade tips; and the sequence, pattern, location, and amount of energy the laser applies to each of the first and second long sides of each of the sheets disposed on each of the plurality of stent folders.

Each of the deforming blade tips has a length substantially equal to the first and the second long sides of the flat sheet of metal, and in one embodiment, deforming blade tips are concave as shown in FIG. 24. In the embodiment shown in FIG. 24, the third deforming blade tip is substantially identical to the sixth deforming blade tip; the second deforming blade tip is substantially identical to the fifth deforming blade tip; and the first deforming blade tip is substantially identical to the fourth deforming blade tip.

Figure 25:
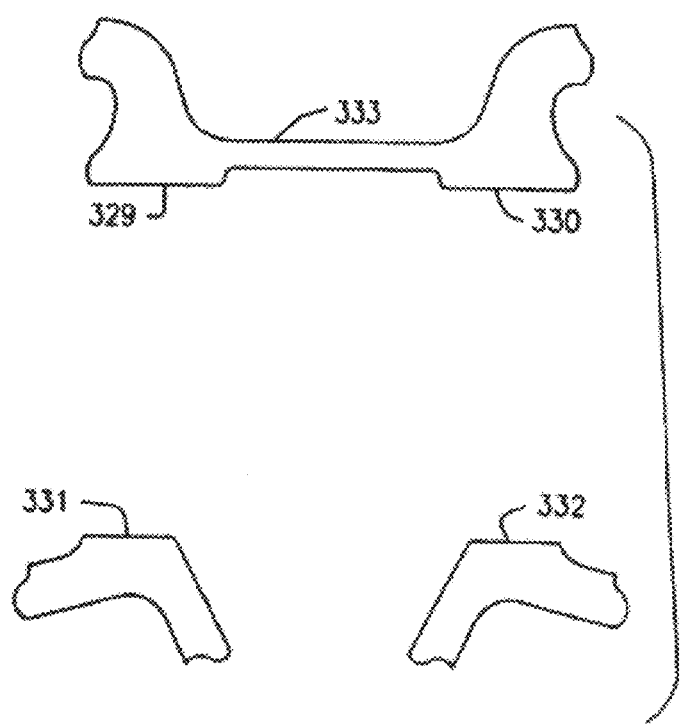
FIG. 25 shows an embodiment of engagement points in accordance with the invention.
Figure 26:
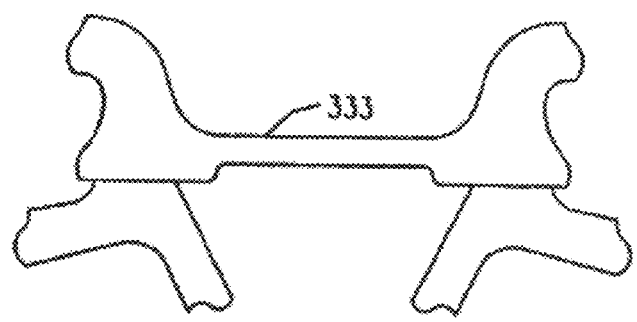
FIG. 26 show an embodiment of engagement points in accordance with the invention.

To fabricate a stent using the apparatus shown in FIGS. 22 to 24 and discussed in detail above, and with reference to FIGS. 27A-27I, first a plurality of stent patterns is cut into a flat piece of metal (metal sheet), each of the patterns having a first major surface and a second major surface, a first long side and a second long side. The first long side and the second long sides are provided with a plurality of pairs of engagement points 329, 330, 331, and 332, for example as shown in FIGS. 25 and 26, disposed substantially opposite each other and sized and disposed to communicate when the pattern is deformed and rolled into a tubular shape. Each pair of the first long side engagement points 329, 330 is provided with a bridge 333 disposed between them. In some embodiments, the bridge 333 has a width that is less than the width of the other portions of the stent.

A sheet 121 containing a stent pattern is disposed on the base 306 so that the first major surface of the sheet is in contact with the base.

Figure 27A:
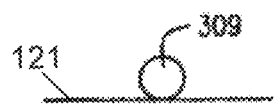
FIG. 27A to 27I shows the sequence of making a stent using the apparatus of FIGS. 22 and 23.

A mandrel 309 is disposed against the second major surface of the sheet 121 between the first long side and the second long side of the sheet with the longitudinal axis substantially parallel to the first long side and the second long side, as shown in FIG. 27A.

Figure 27B:
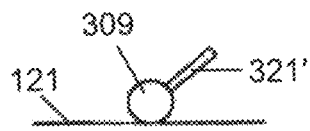

The stent pattern is deformed into a tubular shape so that the first long side pairs of engagement points 329, 330 contact the second long side pairs of engagement points 331, 332, as shown in FIG. 26. The deforming step comprises the steps of: actuating the sixth deforming blade motor so that the sixth deforming blade motor moves the sixth deforming blade in the first direction in an amount sufficient for the sixth deforming blade tip 321' to contact the external surface of the mandrel 309 so as to secure said mandrel against said sheet 121, as shown in FIG. 27B.

Figure 27C:

The first deforming blade motor is activated so that the first blade deforming motor moves the first deforming blade in the first direction in an amount sufficient for the first blade deforming tip 316' to contact the first major surface of the sheet and deform the sheet 121' against the external surface of the mandrel 309, as shown in FIG. 27C.

Figure 27D:
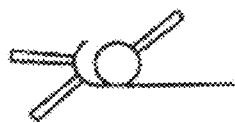

The second deforming blade motor is then activated so that the second deforming blade motor moves the second deforming blade in the first direction in an amount sufficient for the second deforming blade tip to contact the first major surface of the sheet and deform the sheet against the external surface of the mandrel, as shown in FIG. 27D.

Figure 27E:
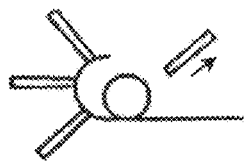

The third deforming blade motor is then activated so that the third deforming blade motor moves the third deforming blade in the first direction in an amount sufficient for the third deforming blade tip to contact the first major surface of the sheet and deform the sheet against the external surface of the mandrel while actuating the sixth deforming blade motor so that the sixth deforming blade moves in the second direction away from said mandrel, as shown in FIG. 27E.

Figure 27F:
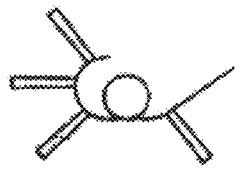

The fourth deforming blade motor is then activated so that the fourth deforming blade motor moves the fourth deforming blade in the first direction in an amount sufficient for the fourth deforming blade tip to contact the first major surface of the sheet and deform the sheet against the external surface of the mandrel, as shown in FIG. 27F.

Figure 27G:
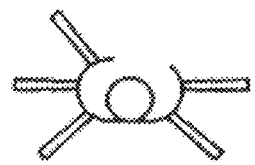

The fifth deforming blade motor is then activated so that the fifth deforming blade motor moves the fifth deforming blade in the first direction in an amount sufficient for the fifth deforming blade tip to contact the first major surface of the sheet and deform the sheet against the external surface of the mandrel, as shown in FIG. 27G.

Figure 27H:
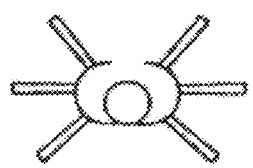

The sixth deforming blade motor is then activated so that the sixth deforming blade motor moves the sixth deforming blade in said first direction in an amount sufficient for said sixth deforming blade tip to contact the first major surface of the sheet and deform the sheet against the external surface of the mandrel, as shown in FIG. 27H.

Figure 27I:
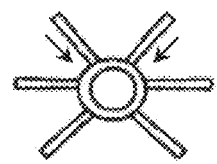

As shown in FIG. 27I, the third and sixth deforming blade motors are then simultaneously activated so that the third and sixth deforming blade motors move the third and sixth deforming blades in the first direction in an amount sufficient for the third and sixth deforming blade tips to contact the first major surface of the sheet and deform the sheet against the external surface of the mandrel, so that the engagement points on the first long side contact the engagement points on the second long side.

After the stent has been deformed and the engagement points have contacted each other, the bridge is cut using the laser. The bridge may have a width that is about 25% to about 50% of the width of the other portions of said stent. In one embodiment the bridge has a width of about 40 microns.

As shown in FIGS. 25 and 26, the engagement points, are sized and adapted to move in an amount sufficient so as to reduce the likelihood of material stress occurring during welding heating and cooling cycles.

Figure 28:
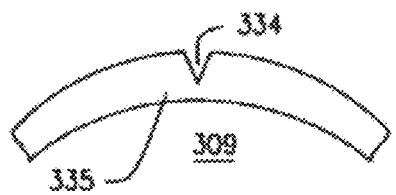
FIG. 28 shows details of a v-shaped notch and gap formed between edges of a sheet and the mandrel.

A V-shaped notch 334 may be formed between the first long side and the second long side when the stent is formed to provide for a stronger weld, as shown in FIG. 28. In addition, as shown in FIG. 28 a gap 335 may be provided between the engagement points and the external surface of the mandrel 309 during the deforming step. This gap 335 provides a greater area for weld material, thus, strengthening the weld and reducing heat dissipation through the mandrel during welding, thus, reducing the amount of energy that must be put into the weld.

The first and second long sides are then connected using the laser to weld each of the engagement points to the engagement point with which it is in contact to form the expandable stent. In some embodiments, the weld is wider than the other portions of the stent. In one embodiment, the weld is about 20% wider than the other portions of the stent and has a width of about 140 microns. The weld is preferably run from outside-to-in. In some embodiments, a plurality of welding runs is used and in one embodiment two weld-runs are utilized. The weld-run may be offset from the point where the engagement points contact each other and in one embodiment is offset about 0.01 mm from the point where said engagement points contact each other. In some embodiments, the weld may be a spot weld, a plurality of spot welds, and in one such embodiment, the weld comprises 5 spot welds.

Figure 30:
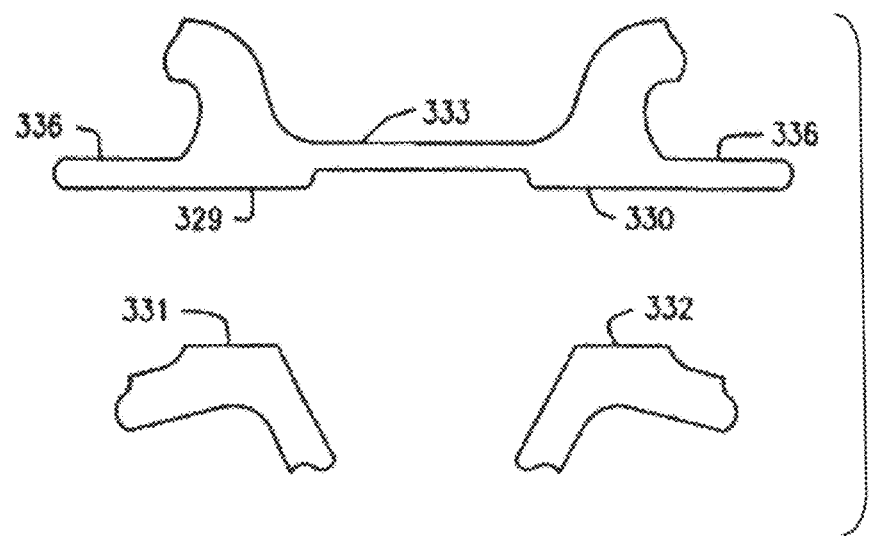
FIG. 30 shows an alternative embodiment of engagement of engagement points constructed in accordance with the invention.
Figure 31:
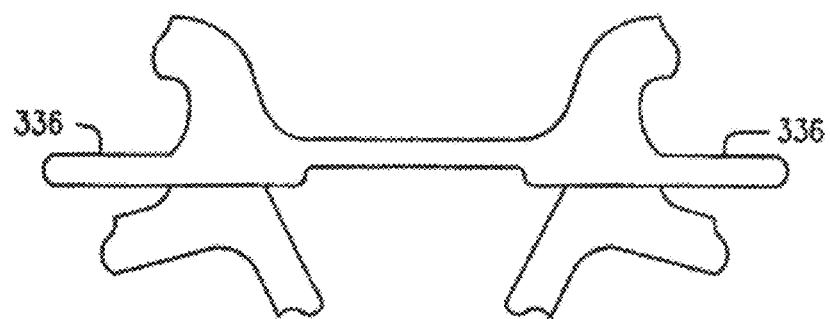
FIG. 31 shows an alternative embodiment of engagement points constructed in accordance with the invention.

FIGS. 30 and 31 illustrate an embodiment similar to that shown in FIGS. 25 and 26, in which pairs of engagement points 329, 330, 331, 332 are disposed substantially opposite each other, and are sized and disposed to communicate when the stent pattern is deformed and rolled into a tubular shape, and each pair of first long side engagement points 329, 330 is provided with a bridge 333 disposed between. This embodiment differs from that in FIGS. 25 and 26 in that additional weld fill material 336 may be provided on the sides substantially opposite the bridge 333 connecting each of the first long side engagement points 329, 330, as shown in FIGS. 30 and 31. The weld fill material 336 is sized and disposed so as to permit the additional weld fill material to be drawn into the weld point during welding.

When the flat sheets comprising stent patterns shown in FIGS. 25, 26, and 30, 31 are made into a stent by cutting the bridges and welding the engagement points, the resulting stent comprises a stent having a longitudinal lumen and preserved stent pattern across the weld line, as discussed in more detail below.

FIGS. 34 to 37 show another embodiment of an apparatus 400 for fabricating a stent constructed in accordance with the invention.

As illustrated in FIG. 34, the apparatus 400 includes a base 401 provided with a sheet receiving area 402 and adapted to receive a flat sheet of metal to be transformed into a stent. The sheet receiving area 402 is also provided with a mandrel receiving groove 409. In one embodiment, the flat piece of metal has a longitudinal axis, a first major surface, a second major surface, a first long side, and a second long side, with the first and the second long sides substantially parallel to the longitudinal axis. An arm 403 having a first end 404 and a second end 405 is provided.

The first end 404 of the arm is adapted to selectively retain a mandrel 406 having a substantially cylindrical external surface. The second end of the arm 405 is hingedly connected to the base 401 and is adapted for movement in a first direction toward the base 401 and in a second direction away from the base 401 to secure the mandrel against a major surface of the flat sheet of metal. The mandrel 406 is sized to have a cross-sectional diameter substantially equal to or less than the internal cross-sectional diameter of the stent to be fabricated.

A means 407 is provided for deforming the flat piece of metal against and around the external surface of the mandrel so that the flat sheet of metal is deformed into a substantially tubular shape conforming to the external surface of the mandrel with the first long side and the second long side substantially parallel to each other. FIG. 36 shows one embodiment wherein the means 407 for deforming is a member provided with a deforming tip 408 having a length substantially equal to the length of the first and second long sides of the sheet metal. In one embodiment, the deforming tip is concave, as shown in FIG. 37.

In operation, a sheet is placed on the sheet receiving area 402. A mandrel 406 is disposed in the first end 404 of the arm 403 and the arm 403 is moved in the first direction so that the mandrel 406 is in contact with the sheet. The deforming means 407 is then used to deform the sheet around the mandrel as previously discussed. The arm 403 is then moved in the second direction and the mandrel with the sheet wrapped around it is removed from the first end 404 of the arm 403. The first and second long sides are then connected as previously discussed to form the stent. In one embodiment, the mandrel with the sheet wrapped around it is transferred to the stent aligning and welding jig shown in FIGS. 38 to 42.

Figure 38:
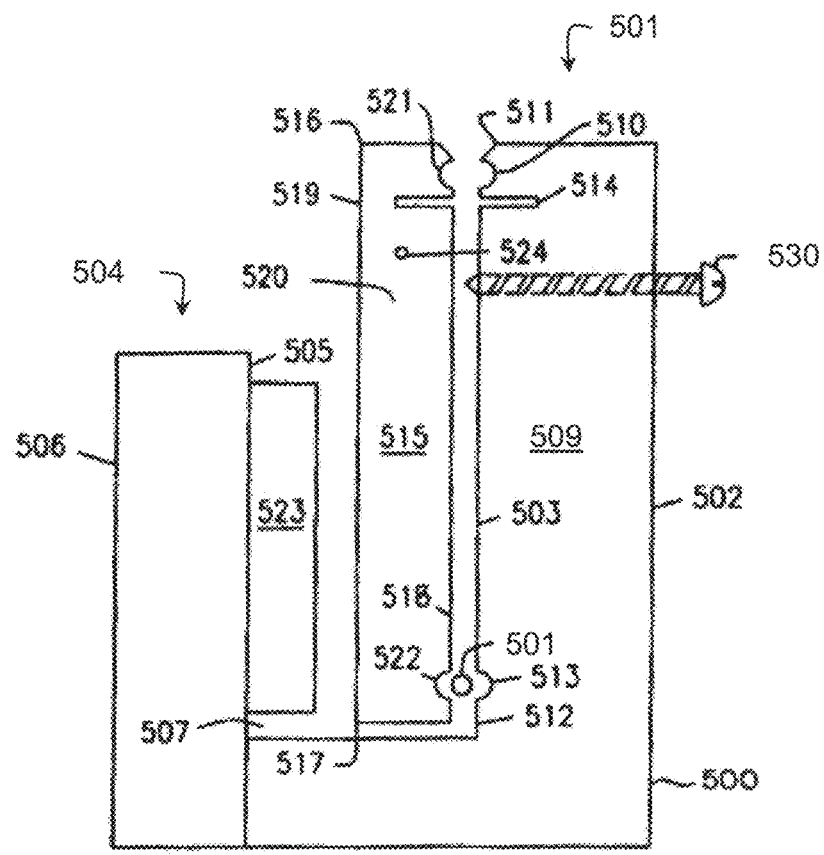
FIG. 38 shows a stent aligning and welding jig constructed in accordance with the invention.
Figure 39:
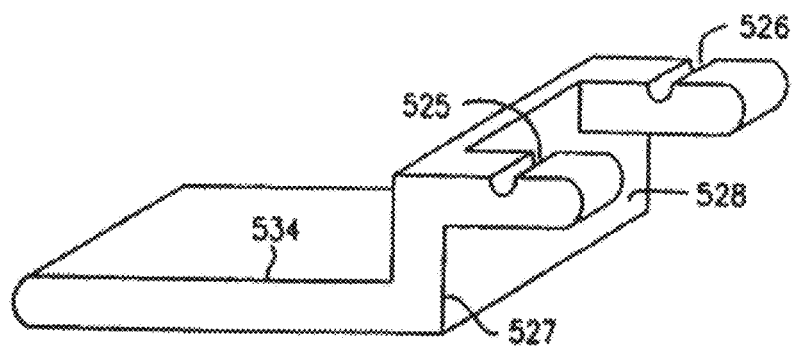
FIG. 39 shows a mandrel support lever.
Figure 40:
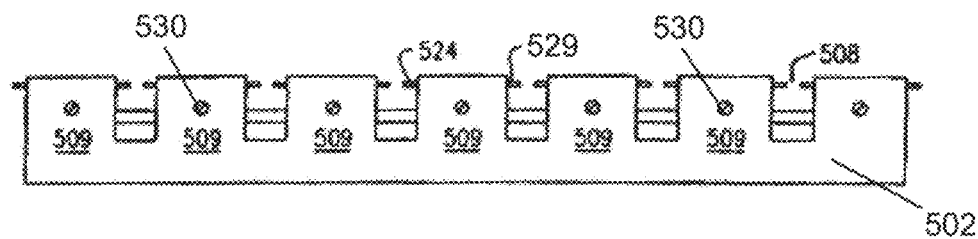
FIG. 40 is a front view of the jig shown in FIG. 38.

The stent aligning and welding jig shown in FIGS. 38 to 42 comprises a base 500 having a first end and a second end provided with a first wall 501 having a first end and a second end and a first major surface 502 and a second major surface 503 and a second wall 504 having a first end and a second end and a first major surface 505 and a second major surface 506. The second major surface 503 of the first wall 501 and the first major surface 505 of the second wall 504 define a longitudinal U-shaped channel 507 having a longitudinal axis in the base 500. As shown in FIG. 40, the first wall 501 is provided with a plurality of slots 508 defining a plurality of first clamping portions 504. Each first clamping portion 504 has a top end 511 and a bottom end 512 and a first major surface coextensive with the first major surface 502 of the first wall 501 and a second major surface coextensive with the second major surface 503 of the first wall 501. Each of the first clamping portions 509 is provided with a first concave channel 510 disposed at the top end 511 of the second major surface 503 of the first clamping portion 509 and a second concave channel 513 disposed at the bottom end 512 of the second major surface 503 of the first clamping portion 509. The first and the second concave channels 510 and 513 are substantially parallel to the longitudinal axis of the U-shaped channel 507. The first major surface 502 of each of the plurality of first clamping portions is also provided with a compensation slit 514 disposed between the first concave channel 510 and the second concave channel 513 extending substantially parallel to the longitudinal axis of the U-shaped channel 507.

A plurality of second clamping portions 515 is disposed in the U-shaped channel 507 between the second major surface 503 of the first wall 501 and the first major surface 505 of the second wall 504. Each of the second clamping portions 515 is disposed in registry with one of the first clamping portions 509. Each of the second clamping portions 515 has a top end 516, a bottom end 517, a first major surface 518, a second major surface 519, a first minor surface disposed at the top end, a second minor surface disposed at the bottom end, a third minor surface 520 disposed between the top end and the bottom end, and a fourth minor surface (not shown) disposed opposite the third minor surface 520 between the top end 516 and the bottom end 517. Each of the second clamping portions 515 is provided with a first concave channel 521 disposed at the top end 516 of the first major surface 518 of the second clamping portion 515 and a second concave channel 522 disposed at the bottom end 517 of the first major surface 518 of the second clamping portion 515. The first and the second concave channels 521 and 522 extend substantially parallel to the longitudinal axis of the U-shaped channel.

A biasing means 523 is disposed between the first major surface 505 of the second wall 504 and the second major surface 503 of each of the second clamping portions 509 for biasing the first major surface of each of the second clamping portions against the second major surface of each of the first clamping portions which are in registry with each other.

A first mandrel support lever positioning pin 524 projects from the third minor surface 520 and a second mandrel support lever positioning pin 529 (see FIG. 40) projects from the fourth minor surface of each of the second clamping portions 515. The mandrel support lever positioning pins 524 and 529 are substantially parallel to the longitudinal axis of the U-shaped channel.

Figure 41:
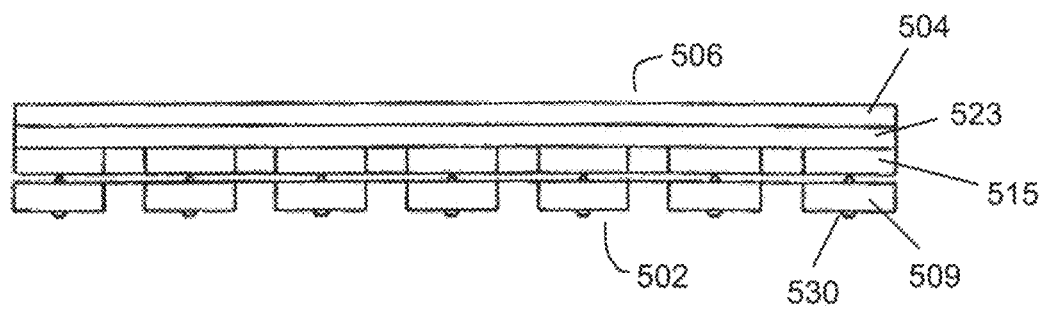
FIG. 41 is a top view of the jig shown in FIG. 40.
Figure 43:
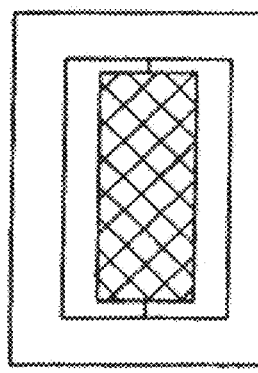
FIG. 43 shows a stent still attached to a metal sheet.
Figure 44:
FIG. 44 is a side view of FIG. 43 showing the stent and the remaining portion of the sheet.
Figure 42:
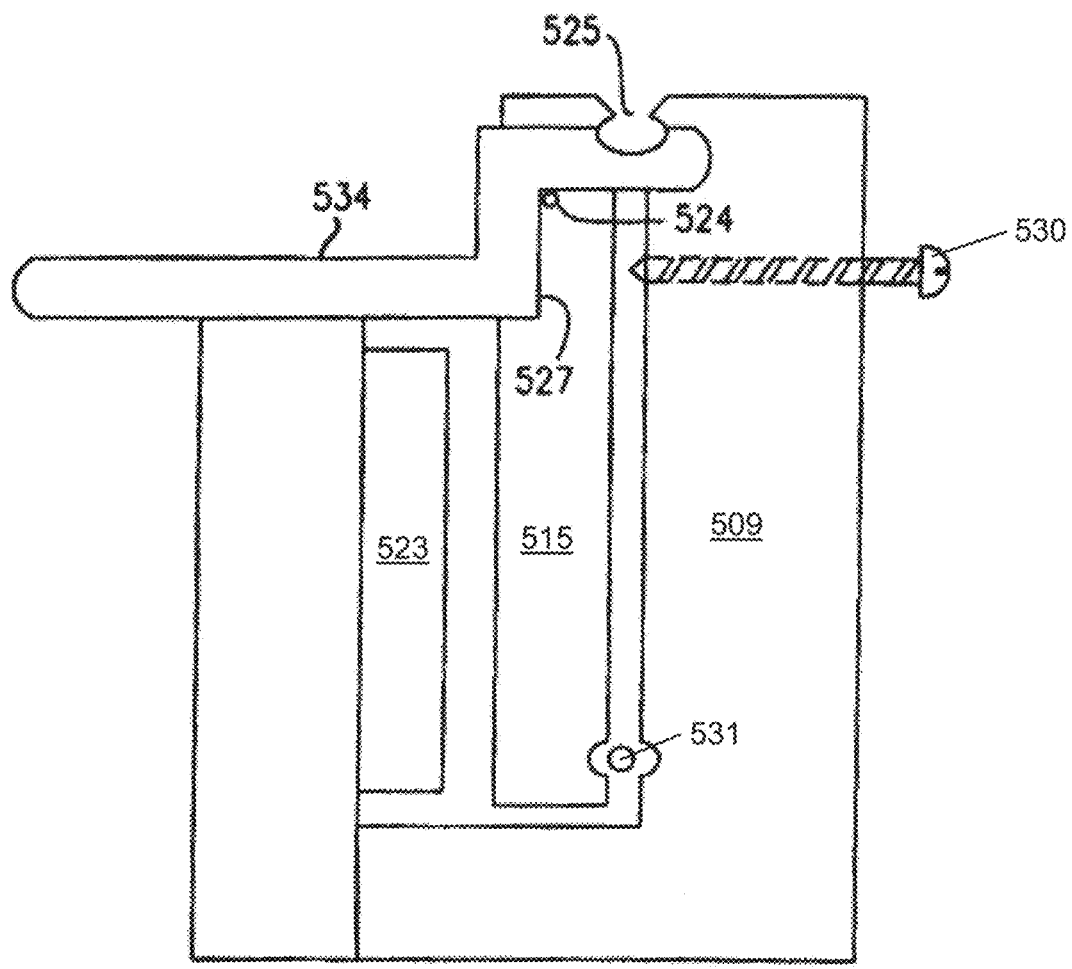
FIG. 42 shows the mandrel support lever of FIG. 39 disposed on the jig of FIG. 38.

A biasing control means 530 selectively controls the distance between the second major surface of each of the first clamping portions 509 and the first major surface 518 of each of the second clamping portions 515, as shown in FIGS. 38, 41 and 42.

A retaining mandrel 531 is disposed in the second concave channel 513 of the first wall and the second concave channel 522 in each of the second clamping portions 515, as shown in FIGS. 38 and 42.

A mandrel support lever 534, as shown in FIG. 39, supports the stent during the alignment of the first long side of the sheet with the second long side of the sheet. The mandrel support lever 534 is provided with a first mandrel support notch 525 (see also FIG. 42) for supporting the first end of the mandrel and a second mandrel support notch 526 for supporting the second end of the mandrel. A first mandrel support lever positioning pin engagement surface 527 engages the first mandrel support lever positioning pin 524 (see also FIG. 42) and a second mandrel support lever positioning pin engagement surface 528 engages the second mandrel support lever positioning pin when the mandrel support lever 534 is disposed on the second wall 504.

It will be appreciated that various elastic materials well known to those skilled in the art as suitable for this purpose may be utilized, e.g., a spring, however, in one embodiment, the elastic material is rubber.

In one embodiment the biasing control means 530 is a threaded screw disposed in each of the first clamping portions 509 with each of the screws 530 communicating with the first major surface 502 and the second major surface 503 of each of the first clamping portions 509, as illustrated in FIGS. 38, 41 and 42. The biasing control means 530 are selectively movable in a direction toward and away from the first major surface 518 of the second clamping portion 515 to selectively move the second clamping portion 515 in a direction toward and away from the first clamping portions 501 to selectively vary the distance between the second major surface 503 of each of the first clamping portions 509 and the first major surface 518 of each of the second clamping portions 515.

In operation, the mandrel with the sheet wrapped around it is secured in the first concave channels 510 and 521. The biasing control means 530, e.g., a screw, is adjusted to secure the mandrel in the first concave channels while permitting the first and second long sides of the sheet to be adjusted so that the engagement points are aligned as desired. In one embodiment, the mandrel support lever 534 shown in FIG. 39, is utilized to support the mandrel during the alignment operation. A shown in FIG. 42, the first mandrel support notch 525 supports the first end of the mandrel and the second mandrel support notch supports the second end of the mandrel. The first mandrel support lever positioning pin surface 527 engages the first mandrel support lever positioning pin 524 and the second mandrel support lever positioning pin surface engages the second mandrel support positioning pin so as to align the mandrel support lever 534 when it is supporting the mandrel.

There are several methods of applying a coating on the stent pattern. In a preferred embodiment of the invention, the flat metal sheet is coated after the stent pattern is formed. The present invention provides the advantage of differentially coating the vessel wall side (outside the cylinder) and the luminal side (inside the cylinder) of the stent. In addition, frontal coating methods provide a more uniform coverage of the coating than currently available methods. The coating can be done after electropolishing the stents in the panel, or without electropolishing. For example, if the polymer coating provides enough protection to the metal stent to make the electropolishing unnecessary for achieving the desired bio-compatibility, electropolishing can be done afterwards or not at all. The complete control of coating on each side of the panel separately allow a high degree of accuracy whether similar or different treatments are desired on both sides. It is thus contemplated that any differential treatment resulting in different polymer properties or dimension and different drug entities, concentrations or elution kinetics may be used. In one embodiment of the invention, only one side of the stent panel will be coated.

The following coating techniques are given as examples and do not limit what types of coating techniques can be utilized in the present invention. There are several coating methods available, for example, as found at http://www.efunda.com/processes/surface/thinfilm_coatings.cfm that will now be discussed.

Physical Vapor Deposition (PVD) and Chemical Vapor Deposition (CVD) are two common types of film coating methods. PVD coatings involve atom-by-atom, molecule-by-molecule, or ion deposition of various materials on solid substrates in vacuum systems.

Thermal evaporation uses the atomic cloud formed by the evaporation of the coating metal in a vacuum environment to coat the surfaces in the line of sight between the substrate and the target (source). It is often used in producing thin, for example 5 μm (20 μin), coatings. The invention is not limited to this thin coating, and can be of any thickness so desired. The thermal evaporation process can also provide a very thick coating, e.g., 1 mm (0.040 in) in thickness.

Sputtering applies high-technology coatings such as ceramics, metal alloys, organic and inorganic compounds by connecting the workpiece and the substance to a high-voltage DC power supply in an argon vacuum system ($10^{-2}$-$10^{-3}$ mmHg). The plasma is established between the substrate (workpiece) and the target (donor) and transposes the sputtered off target atoms to the surface of the substrate. When the substrate is non-conductive, e.g., polymer, a radio-frequency (RF) sputtering is used instead. Sputtering can produce thin, hard thin-film coatings, e.g. less than 3 μm (120 μin).

Chemical Vapor Decomposition (CVD) Coatings: CVD is capable of producing thick, dense, ductile, and good adhesive coatings on metals and non-metals such as glass and plastic. Contrasting to the PVD coating in the "line of sight", the CVD may be used to coat all surfaces of the substrate.

Conventional CVD Coating process requires a metal compound that will volatilize at a fairly low temperature and decompose to a metal when it is in contact with the substrate at higher temperature. The most well known example of CVD is the nickel carbonyl ($NiCO_4$) coating as thick as 2.5 mm (0.1 in) on glass windows and containers to make them explosion or shatter resistant.

Another method of coating is spray coating. Depending on the embodiment, the spraying method may utilize a microspray atomizing nozzle with low-pressure gas to produce a highly focused beam of atomized spray drops.

Figure 50:
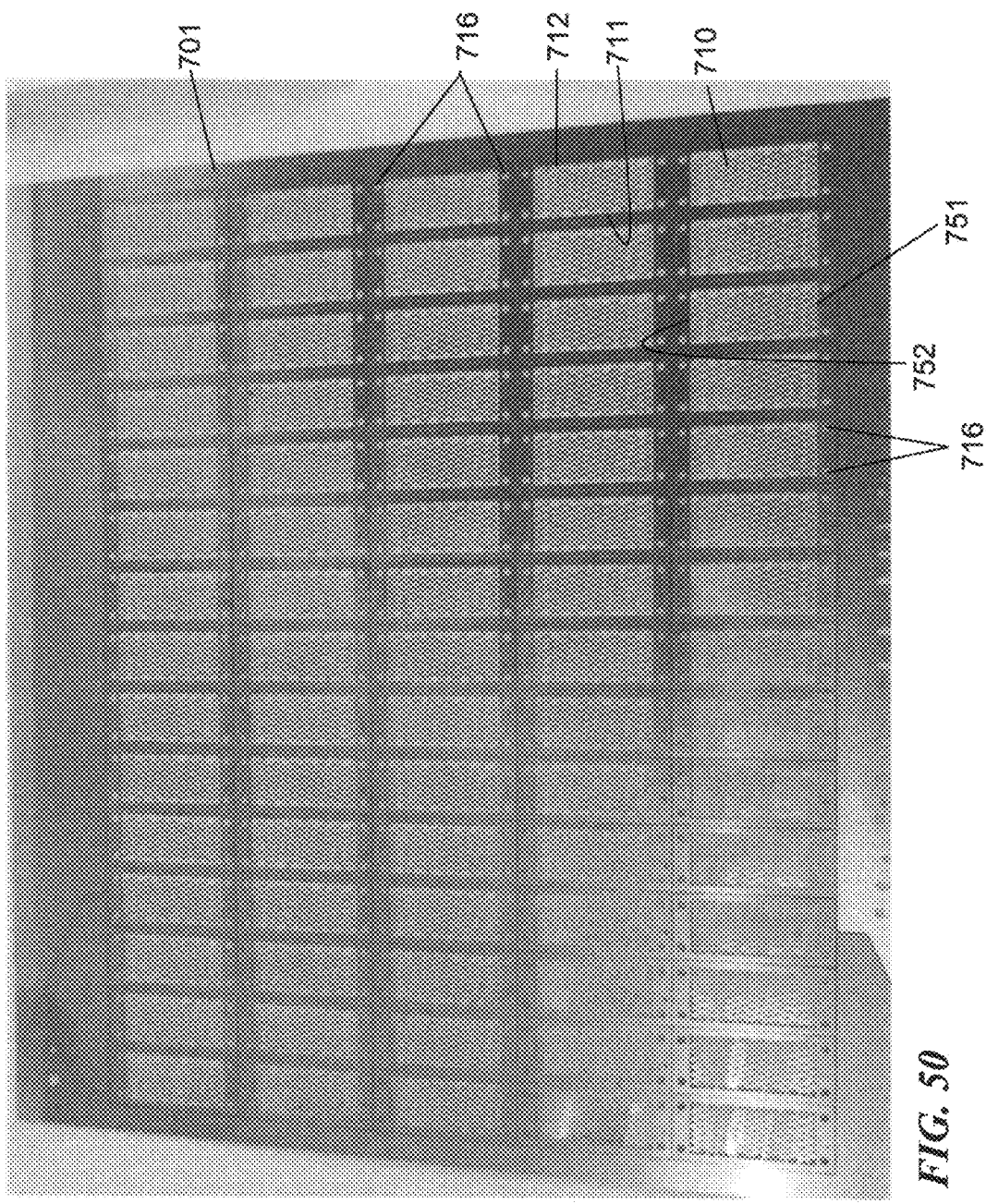
FIG. 50 is a photograph of a flat metal sheet into which a plurality of stent patterns including reservoirs have been cut.

In one method of drug coating a stent, the base material of a stent is coated with a polymer and a drug prior to assembly. A plurality of stent patterns are cut into a piece of sheet metal ("panel"), as shown in FIGS. 6 and 50, and prior to rolling the sheet metal into a tubular stent, the flat piece of sheet metal is coated with a polymer and drug. The sheet metal can be coated either before or after the pattern of the stent is formed depending on the embodiment. The coating may be applied either before or after electropolishing the stents in the panel. Alternatively, if the polymer coating provides enough protection to the stent to allow for the desired bio-compatibility, the coating may be applied without electropolishing the stent. After coating the flat sheet metal, the steps of rolling and welding the stents are performed.

As described above the coating can be done with a polymer and drug when the stents are still in the panel and performing the step of rolling them and welding them after they are already coated.

There are many advantages of the coating in the flat configuration. For example, uniformity of a drug along and across the stent surface may be achieved. The uniformity of frontal coating such as spraying or evaporation is much higher and easier to achieve with flat surfaces than it is with cylindrical surfaces of finished stents.

Figure 45A:
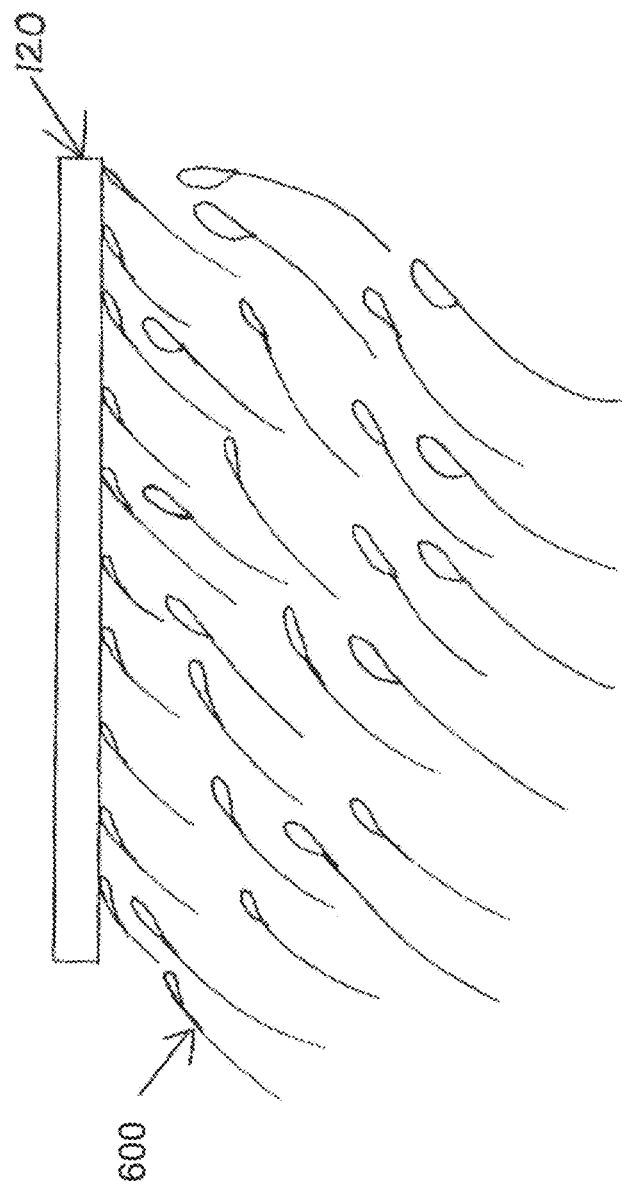
FIG. 45A is a side view of the sheet metal containing a stent pattern being coated in accordance with one embodiment of the invention.
Figure 45B:
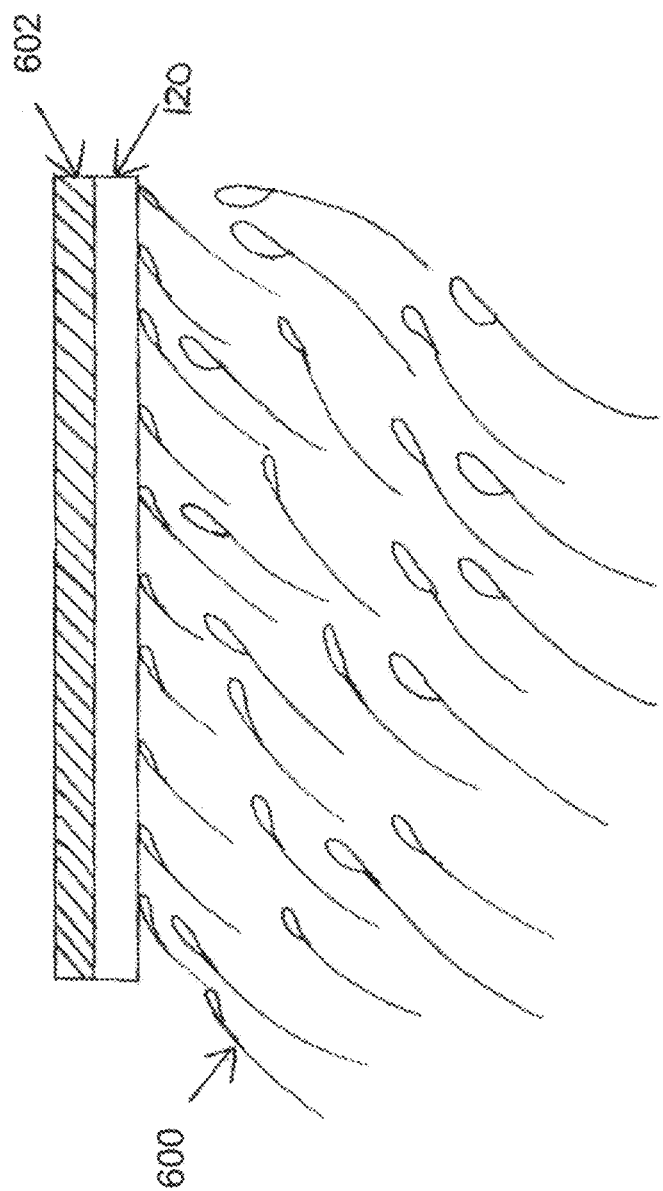
FIG. 45B is a side view of the sheet metal shown in FIG. 45A covered with a mask and coated in accordance with one embodiment of the invention.

In addition there is a possibility of differential treatment of the luminal side of the stent (inside) and the vessel wall side (outside) is straight forward when coating a flat article. This may be achieved with or without the use of a mask as shown in FIGS. 45B and 45A, respectively.

The advantage of coating the stents when they are in a panel includes better cost efficiency when coating, for example, 100 stents at a time from multiple spray nozzles or ink-jet type nozzles. There is an economical advantage to coat a single flat stent, but coating multiple stents is a larger economic impact. In addition, the quality gain of coating together many stents or stent panels in one process and the uniformity of coating across a lot is of great importance.

Figure 1B:
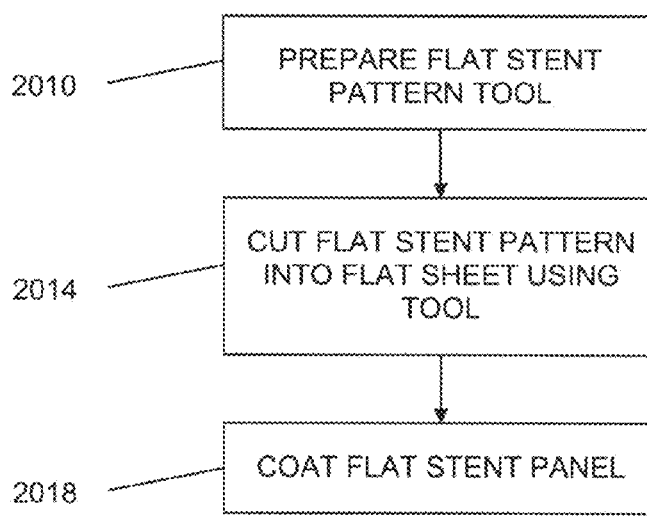
FIG. 1B is a flow chart illustrating one embodiment of the flat process of drug coating a stent pattern according to the invention.

As illustrated in FIG. 1B, in one embodiment of the invention a flat pattern design of a stent is prepared. This preparation and cutting of the stent pattern are illustrated in reference blocks 2010 and 2014. Preparation and cutting of such flat pattern designs are shown, for example, U.S. Pat. No. 6,692, 522, and U.S. Pat. No. 5,906,759, that are both in toto incorporated by reference.

In the embodiment shown in FIG. 1B, the coating step 2018 takes place after the pattern is cut. However, as previously described, the coating may be applied before or after the patterns are cut into the sheet metal.

FIGS. 45A and 45B are similar to FIGS. 6 and 7 in that like reference numerals refer to similar elements previously described. In FIGS. 45A and 45B, however, the stent patterns are being subjected to a coating process. A side view of the flat sheet 121 containing a plurality of stent patterns 120 shown in FIGS. 6 and 7 is shown in FIG. 45A. A coating substance 600 contacts the stent patterns 120. As previously described, there are many coating techniques that may be used with the invention, such as but not limited to, spraying and evaporation techniques. The coating can be differential on one side or made on both sides of the flat metal panels or sheet. In addition, coating combinations can be made on the flat metal. For example, two different coatings may be applied onto either one or both sides of the stent or various coating combinations.

FIG. 45B shows use of a mask 602 on the stent panel 120. The mask may be made of any material and is removable to protect one side of the panel from being coated (for example where differential coating is desired) or protect specific areas such as the weld point, a bending portion or other portion of the stent pattern from being coated. This mask may or may not be used depending on the embodiment. With or without the use of the mask 602, the process of coating stents with the polymer and/or drug when the stents are still in the panel provides many advantages as previously described. In addition, differential treatment of the luminal side of the stent and the vessel wall side may be obtained with or without the use of the mask 602, depending on the coating technique used.

In one embodiment, it may be desirable to apply a coating containing a therapeutic agent only to specific portions of the stent pattern, e.g., on non-bending portions such as, for example, struts, without using a mask. Thus, to achieve accurate, limited coating of portions of a stent pattern, in accordance with the present invention, a method similar to that for depositing substance in drug reservoirs of a flat stent pattern (described below) can be used for flat discrete-coating stents. A flat map of those discrete portions to be coated may be generated based on the tool used for forming the stent pattern in the flat sheet or based on a scan of the cut or etched flat stent pattern. The location information about discrete portions where coating is desired, for example structures that bend and those that do not bend during crimping and expansion of the stent, is then contained in the flat map, and this information may be used to coat the discrete portions or spots on the stent pattern, while avoiding portions of the stent pattern surface where coating is not desired. For example, the flat map may include information about the location of the non-bending portions or other regions to be coated, this information may be used in a software program to instruct an apparatus where to coat the surface of the flat sheet or flat stent pattern, and these discrete portions may then be accurately and efficiently coated on one or both sides of the flat sheet.

Figure 1C:
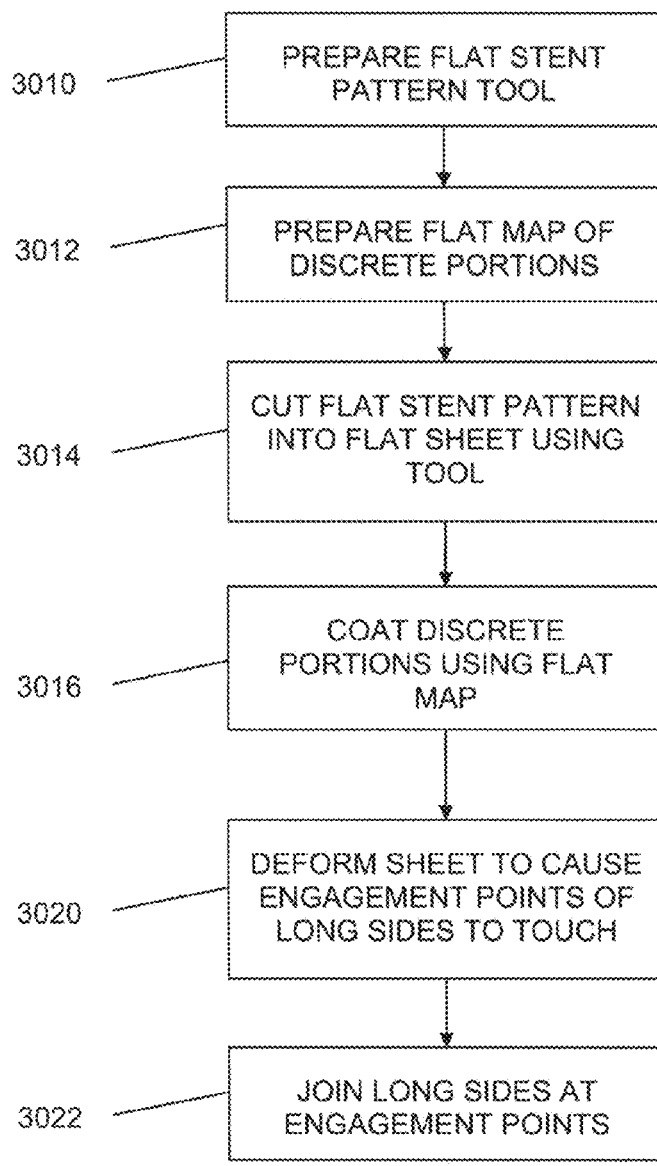
FIG. 1C is a flow chart illustration of one embodiment of the flat process of discrete drug coating pattern according to the invention.

The method of discrete-coating may include the steps illustrated in FIG. 1C. In step 3010, a flat stent pattern tool may be prepared, as described in more detail below for step 4010 of FIG. 1D. After preparing the tool, in step 3012 a flat map of discrete portions, or spots, where coating is desired to be placed, may be generated in a manner similar to generating a pattern of reservoirs for depositing a therapeutic composition. In step 3016, the coating may then be applied only at those locations, before or after forming the stent pattern in the flat sheet using the tool, as in step 3014. The stent pattern may be formed in the flat sheet by implementing any of the methods described in detail above. After forming the stent pattern and discrete-coating the flat sheet, as described in more detail above, the coated stent pattern may be deformed into a tubular structure, so that the longitudinal sides of the stent pattern touch in step 3020. The edges of the longitudinal sides may then be attached to form the discrete-coated stent in step 3022, for example at engagement points, as described above.

In another embodiment, the method of discrete-coating according to the invention may be advantageous to overcome the problem of cracking of the coating at flex points, which can lead to further flaking of the coating. Thus, a flat map of those portions of the stent where a therapeutic composition is desired (the discrete portions or spots) may be generated based on a tool that is used for cutting or etching the stent pattern into the flat sheet. Such portions of the stent pattern may be those portions that do not bend or deform when the stent is crimped for delivery or radially expanded for implantation, e.g., non-flexing portions.

Figure 58A:
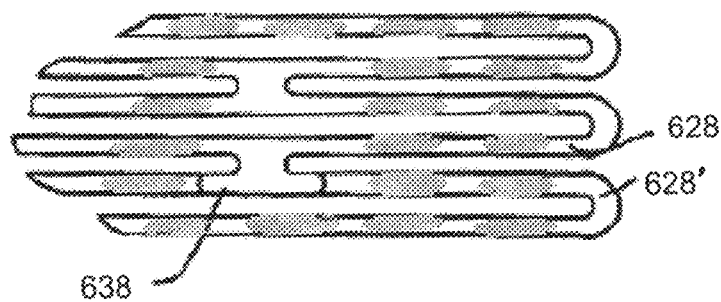
FIGS. 58A-C are schematic illustrations of discrete-coated portions on portions of three different stent patterns.
Figure 58B:
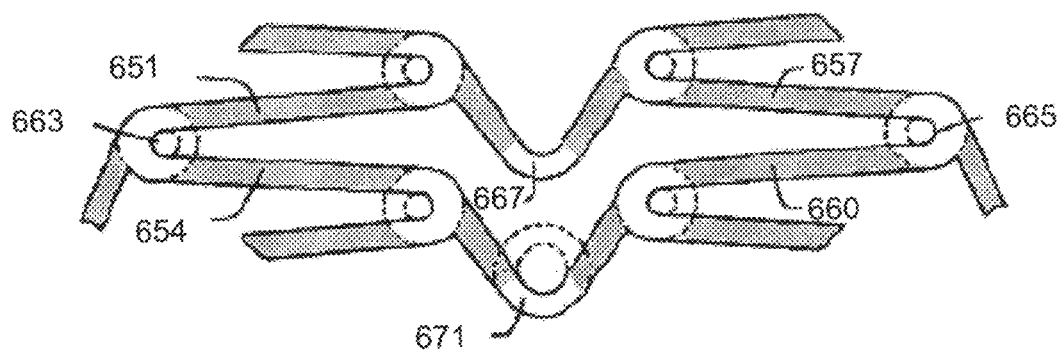
Figure 58C:
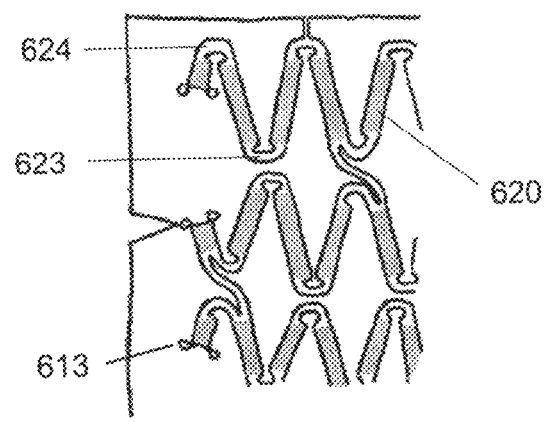

Non-limiting examples of the discrete-coating of the stent pattern are illustrated schematically by the shaded portions of FIGS. 58A-58C. For example, as illustrated in FIGS. 58A and 58C, strut members 651, 654, 657, 660 and struts 620 are spot coated portions, whereas flexible portions 628, 628', flexor loops 623, 624, and protrusions 638, 613 may be non-coated portions. As illustrated by shaded portions in FIG. 58B strut members 651, 654, 657, 660 and non-flexing portions of first and second compensating members 667, 671 are coated whereas the flexible portion of first and second compensating members 667, 671, and the first and second flexible loops 663, 665 that connect strut members may be non-coated portions. In such embodiments, portions to be coated may be determined by selecting the strut members from the tool and further assigning appropriately spaced spots within those strut members and generating a flat map of the spots.

Figure 59A:
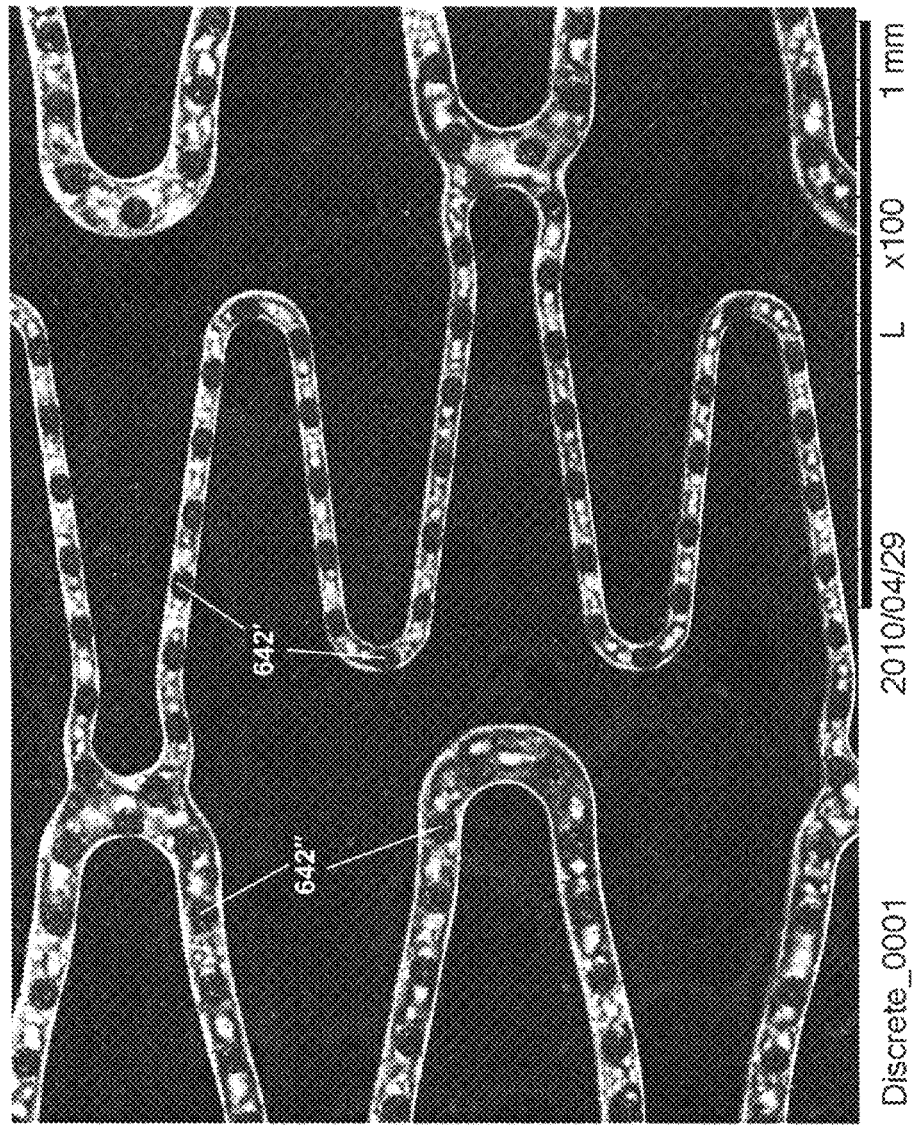
FIGS. 59A-B are photographs of a discrete-coated flat stent pattern.
Figure 59B:
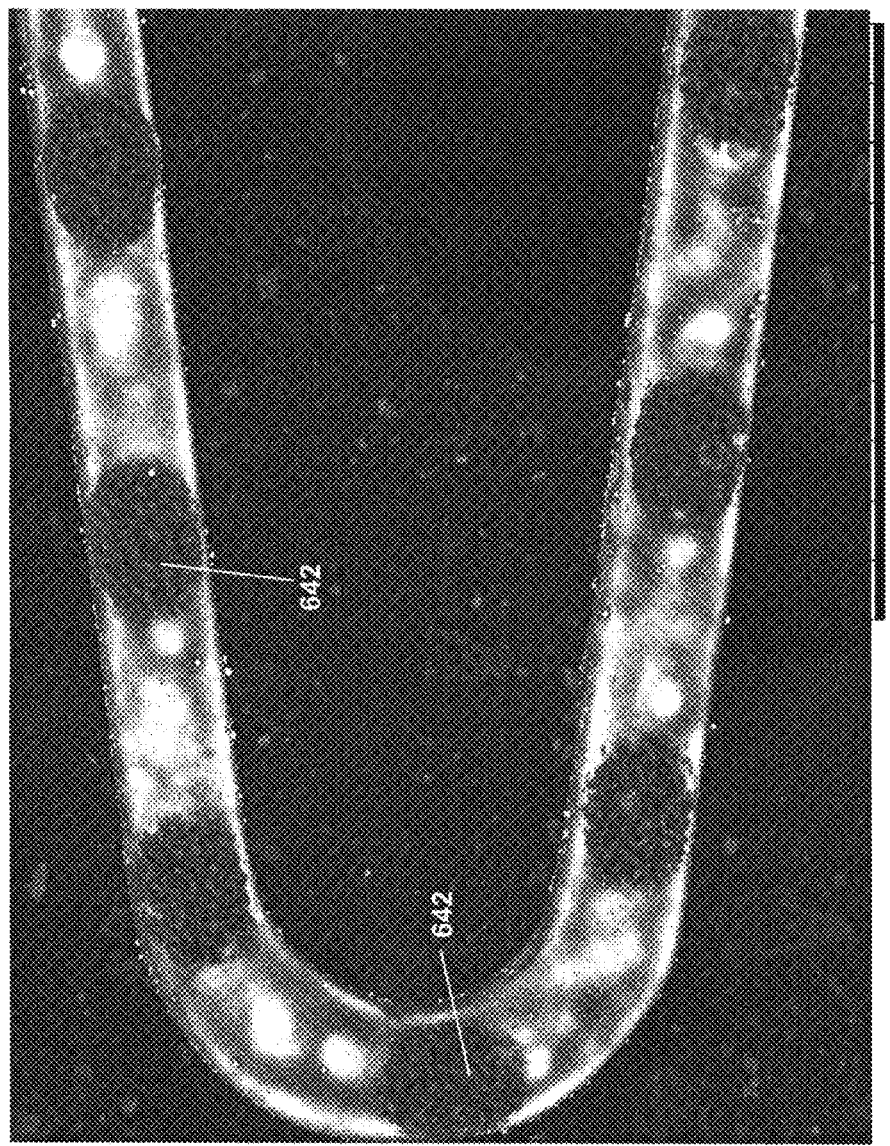

FIG. 59A is a photograph, taken by scanning electron microscope (SEM), of a flat stent pattern that has been discrete-coated with two different shaped spots 642', 642" using the ink-jet method. Differently shaped or sized discrete portions may be used to accommodate the different widths or shapes of the members of the stent pattern, as illustrated in FIG. 59A. FIG. 59B is a higher power SEM photograph illustrating discrete-coat spots 642 on a flat stent pattern. FIGS. 59A and 59B further illustrate the use of appropriately sized and placed discrete-coat spots on both flexing members and non-flexing members of the stent pattern.

Figure 51A:
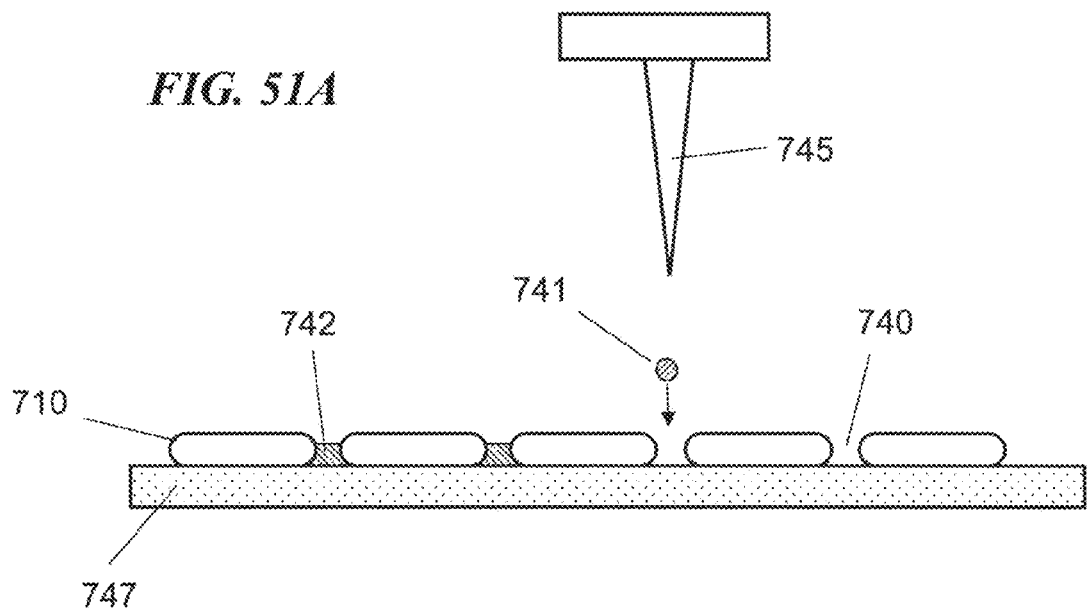
FIG. 51A is a schematic view of a system for filling reservoirs of a flat stent pattern.
Figure 51B:
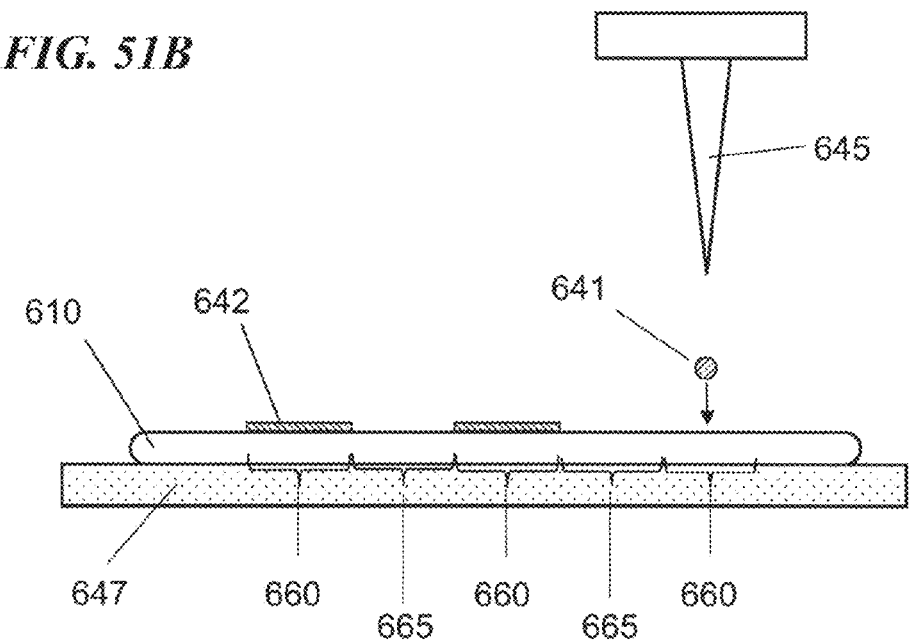
FIG. 51B is a schematic view of a system for discrete-coating a flat stent pattern.

FIG. 51B schematically illustrates one example of a system for discrete-coating a flat sheet or flat stent pattern. A cross-section through a region of a stent pattern 610, including portions to be coated 660 and portions to remain uncoated 665, that is placed for convenience on a base 647. A base is not required for the flat discrete-coating method. A composition 641 may be expelled or released from a nozzle 645, by methods known in the art, e.g., by ink-jet or ion beam spraying or PVD, onto the surface of the flat stent pattern at the discrete portions to form a discrete-coating area 642. As used herein, by ink-jet is meant the discrete deposition of an accurate dose of liquid material by accelerating it towards the surface by pressure, electrostatic charge or other technique. The nozzle 645 may be moved in the X-Y direction over the stent pattern to the discrete portions according to the discrete-coat flat map generated from a scan of the stent pattern formed in a flat sheet or the tool used to form the stent pattern (see step 3012 of FIG. 1C). The method of mapping and controlling the position of the nozzle for flat discrete mapping is similar to that described above for flat filling. Multiple nozzles 645 may be used where a plurality of stent patterns is being coated simultaneously.

By limiting a therapeutic drug coating to the pre-selected regions of the stent, the method of the invention can assure the accuracy of therapeutic dose on the coated stent. Alternatively, on the same stent pattern some struts may have drug reservoirs containing a first therapeutic agent or coating combination, and other struts may be coated or spot coated with a second therapeutic agent or coating combination.

Because the location of the portions to be coated may be mapped based on the tool for generating the stent pattern, the discrete coating process may be automated and computerized. This is advantageous for the same reasons that flat coating of an entire stent and flat filling of reservoirs—more than one stent pattern or sheet to be cut with a stent pattern may be discrete-coated at the same time. Further, because a plurality of stent patterns may be formed from a single flat sheet, consistency of therapeutic dose and quality of coating is improved within and across batches of discrete-coated stents, as it is for fully flat-coated stents and stents with flat-filled drug reservoirs.

The discrete coating method also permits differential coating. Thus portions or spots on one side of the stent pattern may be coated with one therapeutic agent, and portions on the other side of the stent pattern may be coated with another therapeutic agent, or not coated at all. Alternatively, different portions of one side of the stent pattern may be coated with different therapeutic agents.

Figure 45C:
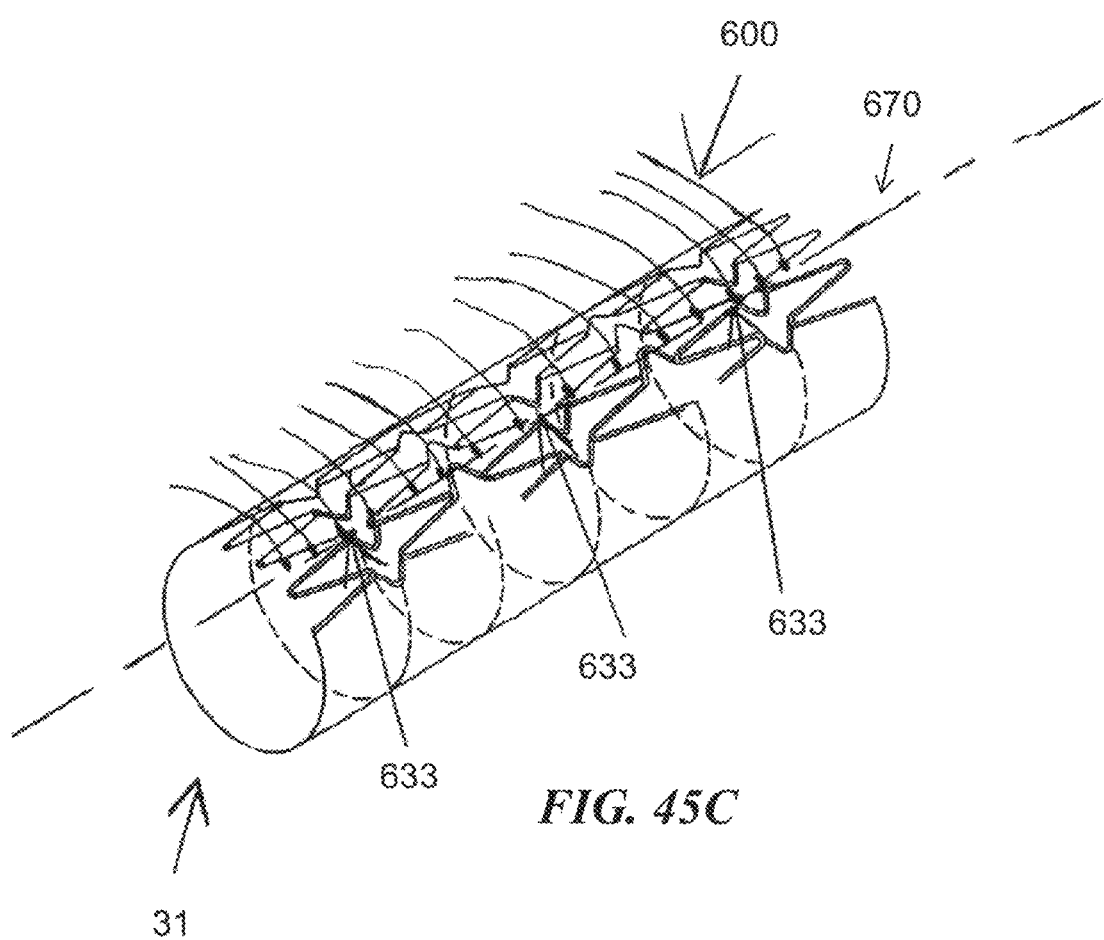
FIG. 45C is a perspective view of a stent receiving a line of coating after welding the stent to cover areas of the weld if the heat during weld generates gaps in the effective drug and/or polymer coating due to heat damage of the weld.

FIG. 45C is a perspective view of the stent 31 of FIG. 4 receiving a line of coating after welding the stent to cover areas of the weld if the heat during weld generates gaps in the drug and/or polymer coating due to heat damage of the weld. Again, the present invention can be utilized with any stent design and is not limited to the stent examples given herein. The coating may comprise the same substance or a different substance as compared to the coating substance initially applied to the stent, depending on the embodiment. The coating 600 substance may be applied along the weld line axis "670" of stent 31 or may be specifically targeted to weld points 633. This secondary coating run is useful to coat, with the drug and/or polymer, the weld points 633 in the even that the heat generated by the welding process generates a gap in the effective drug and/or polymer continuity.

Various drug and polymer coatings can be utilized with the present invention. For example, the drug coatings or drug and polymer coating combinations that are used to deliver the drug, i.e. therapeutic and/or pharmaceutical agents may include: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); antiinflammatory: such as adrenocortical steroids (cortisol, cortisone, fludrocortisone, prednisone, prednisolone, 6.alpha.-methylprednisolone, triamcinolone, betamethasone, and dexamethasone), bisphosphonates, non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF) platelet derived growth factor (PDGF), erythropoetin, angiotensin receptor blocker; nitric oxide donors; anti-sense oligionucleotides and combinations thereof; cell cycle inhibitors, mTOR inhibitors, and growth factor signal transduction kinase inhibitors. The flat metal panels are coated with one or more of the drug coatings or drug and polymer coating combinations. Other substances, such as bisphosphonates, can be used with the present invention, as described in U.S. Pat. No. 7,008,645 to Golomb et al., which is incorporated, in toto, by reference.

Polymer coatings can include, but are not limited to, poly (glycol methacrylate), poly(methyl methacrylate), poly(ethyl methacrylate), poly(butyl methacrylate), poly(sulfanato ethyl methacrylate), poly(ethylene-co-vinyl acetate), poly(ethyl acrylate), poly(urethane-acrylate), poly(acrylamide-co-ethyl methacrylate), poly(divinyl benzene), poly(triethylene glycol-co-divinyl ether), poly(tri-methylol propane triacrylate), poly(pentaerythritol tetraacrylate), poly(Bisphenol A ethoxylate diacrylate), poly(allyl ether), poly(diallyl maleate), poly(vinylidene fluoride), poly(triallyl isocyanurate), and blends thereof. Other polymers used in the coating, for example, may be found in U.S. Pat. No. 6,673,385 to Ding, incorporated, in toto, by reference.

Figure 1D:
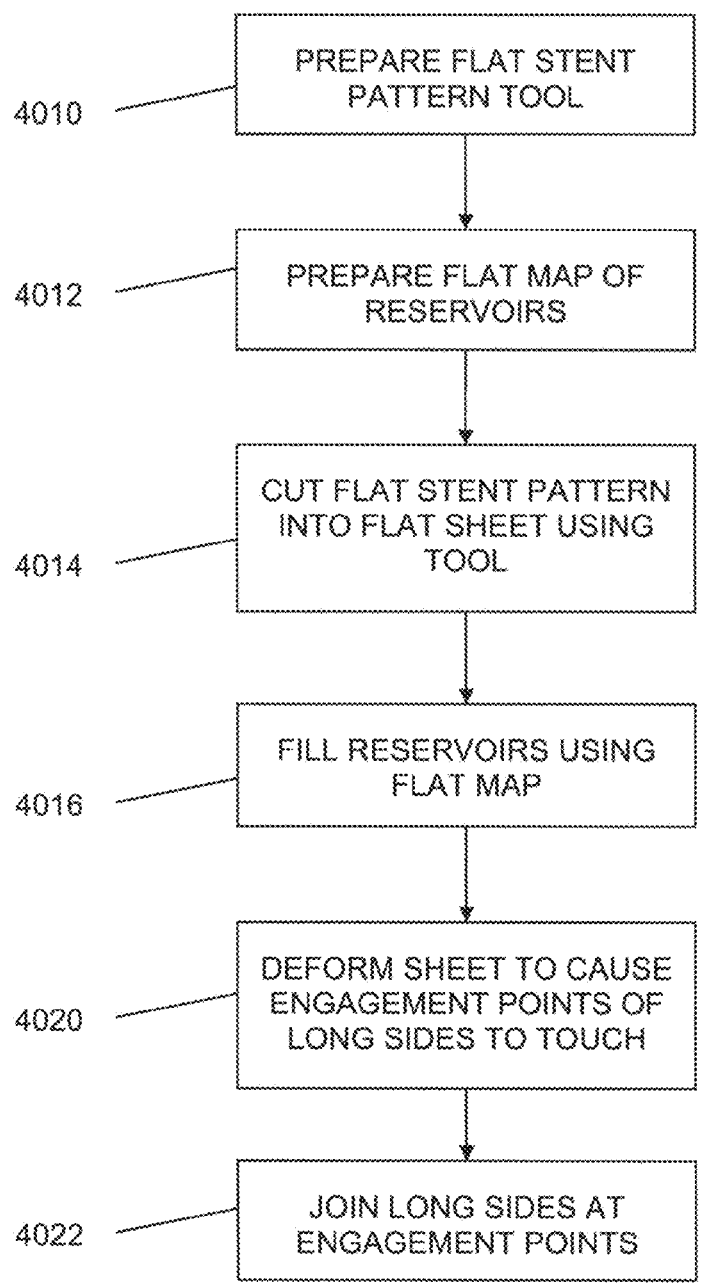
FIG. 1D is a flow chart illustration of one embodiment of the flat fill stent fabrication method according to the invention.
Figure 46:
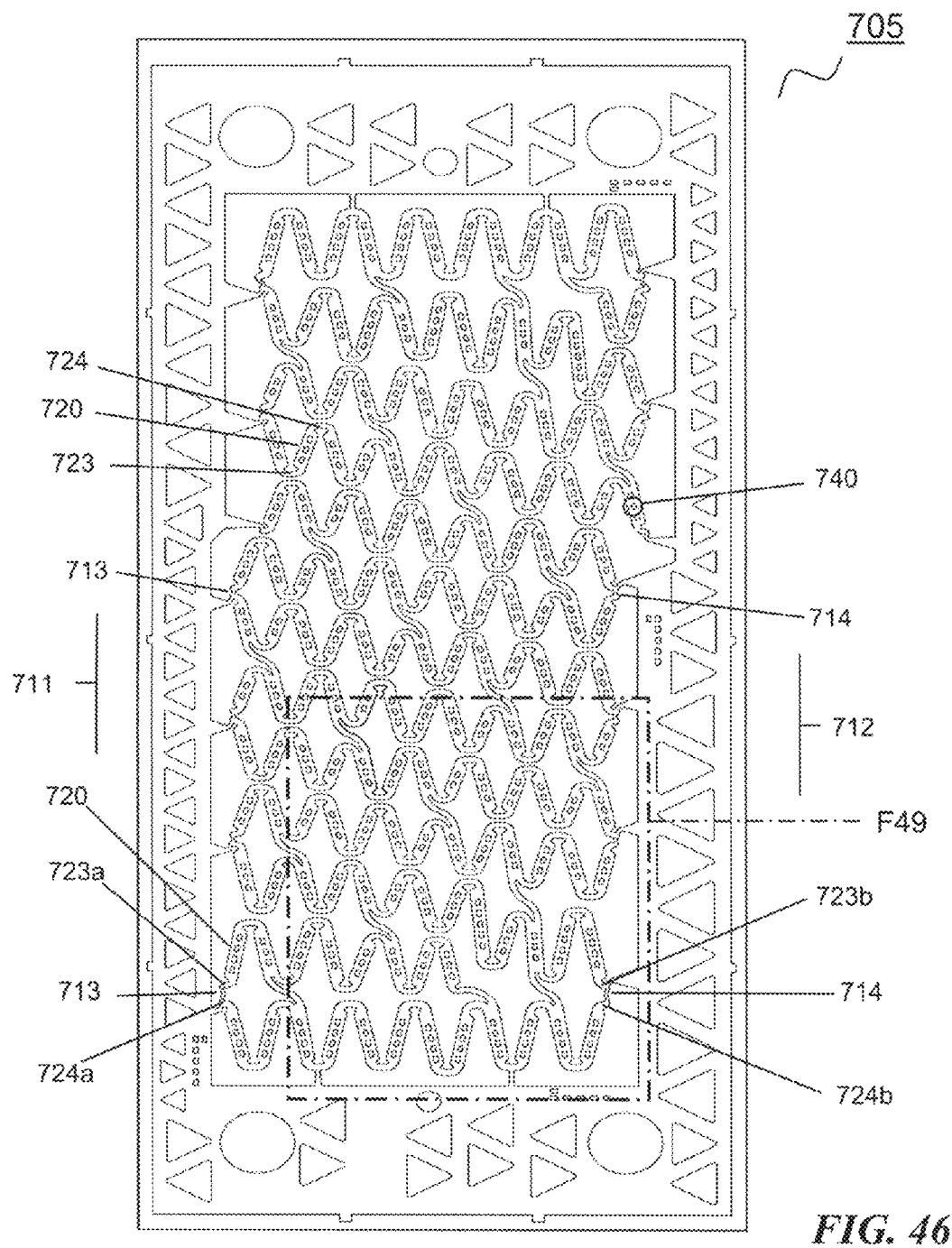
FIG. 46 illustrates a tool that may be used in accordance with the invention to cut one or more stent patterns including reservoirs into a flat metal sheet.

In the method for fabricating a drug-filled stent outlined in FIG. 1D, first a drawing of the desired stent pattern is prepared in a flat format (step 4010) to create a tool for cutting the stent pattern having reservoirs into a flat sheet. An exemplary drawing, or tool 705, of a flat stent pattern that may be used in accordance with the invention is illustrated in FIG. 46. The stent pattern may be any stent design that includes reservoirs preferably located in non-flexing portions of the stent, for example, a stent pattern having a plurality of struts, where one or more struts may have one or more reservoirs. By "reservoir" is meant an opening for containing a composition, such as for example a fenestration (through-hole) or a recess (blind hole).

After the tool 705 has been generated for the stent pattern, in step 4012 a flat map of the reservoirs is prepared. In certain embodiments a first flat reservoir map may be generated for the first major surface of the stent pattern, and second flat reservoir map may be generated for the second major surface of the stent pattern. The major surfaces of the stent pattern become the vessel wall side and lumen side of the tubular stent. In an alternative embodiment, a flat reservoir map may be prepared from a scan of the flat stent pattern that has been cut into the flat sheet. In this embodiment, step 4012 may be performed after step 4014.

Figure 47:
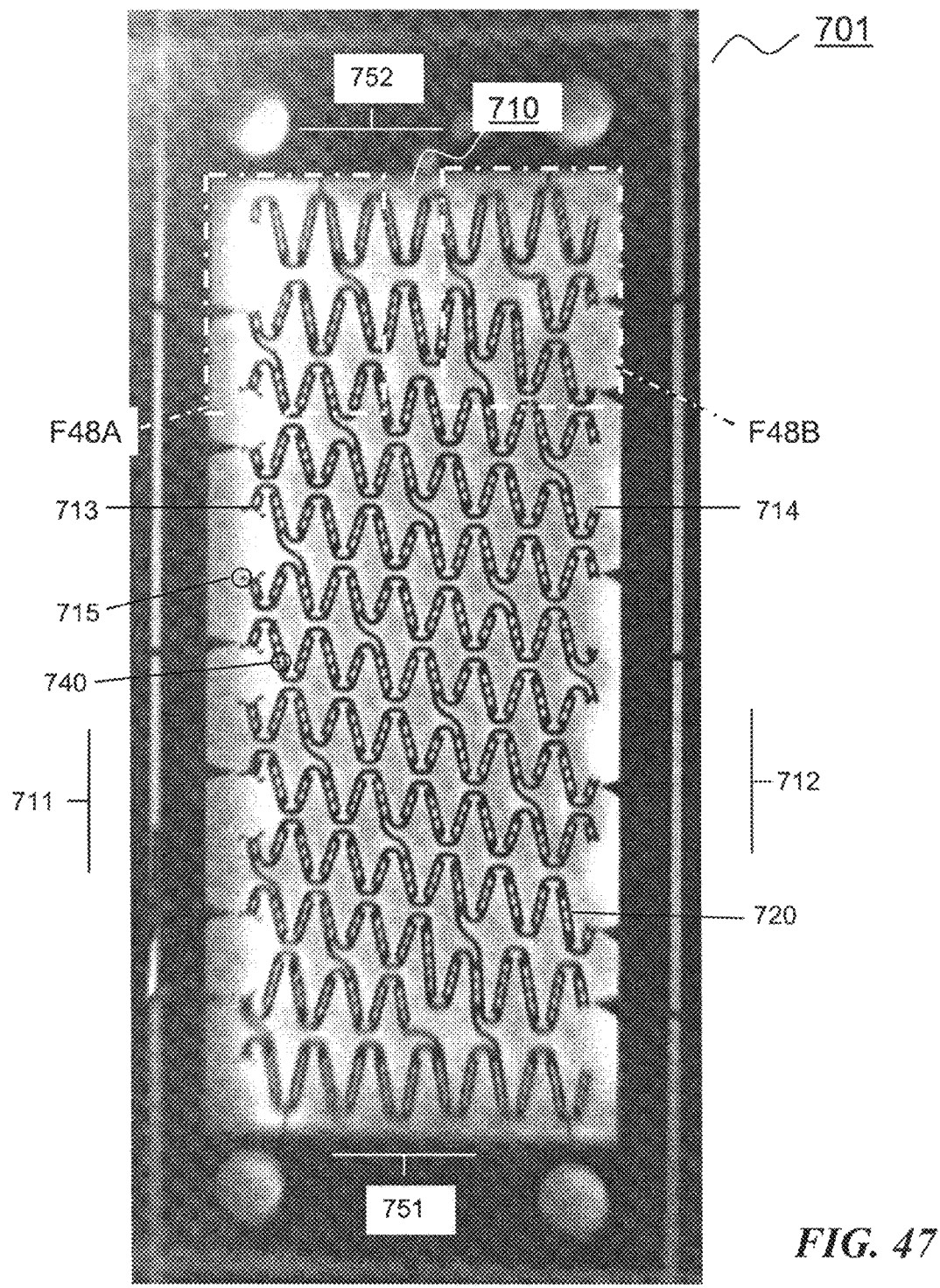
FIG. 47 is a photograph of a flat metal sheet into which a stent pattern including reservoirs has been cut.

In step 4014, the stent pattern is cut or etched into a flat sheet of strong biocompatible material based on the tool 705. The sheet can be any type of biocompatible material, for example a metal such as stainless steel, Nitinol, cobalt-chromium or similar materials, or a material which is plated with a second biocompatible material. This flat sheet is referred to herein as "sheet metal" or a "metal sheet," however the skilled artisan recognizes that other suitable biocompatible materials may similarly be used. As manufactured, the stent pattern should be designed so that the stent may be crimped for delivery and expanded on deployment in the blood vessel. The material used should be strong and durable to support the vessel wall for the desired duration. An example of a stent pattern 710 cut into a flat metal sheet 701 is illustrated in FIG. 47.

Step 4014 permits a predetermined stent pattern design to be cut into one or more stent base materials in a single flat sheet, providing high reproducibility and efficiency. The stent patterns may be cut into the flat metal sheet using multiple-up-etching and both sides of the stent pattern are inspected after etching (and preferably after filling the reservoirs) and before the stent pattern is rolled into a tubular form. In one embodiment, the inspection step is carried out using an automated optical inspection apparatus.

Figure 49:
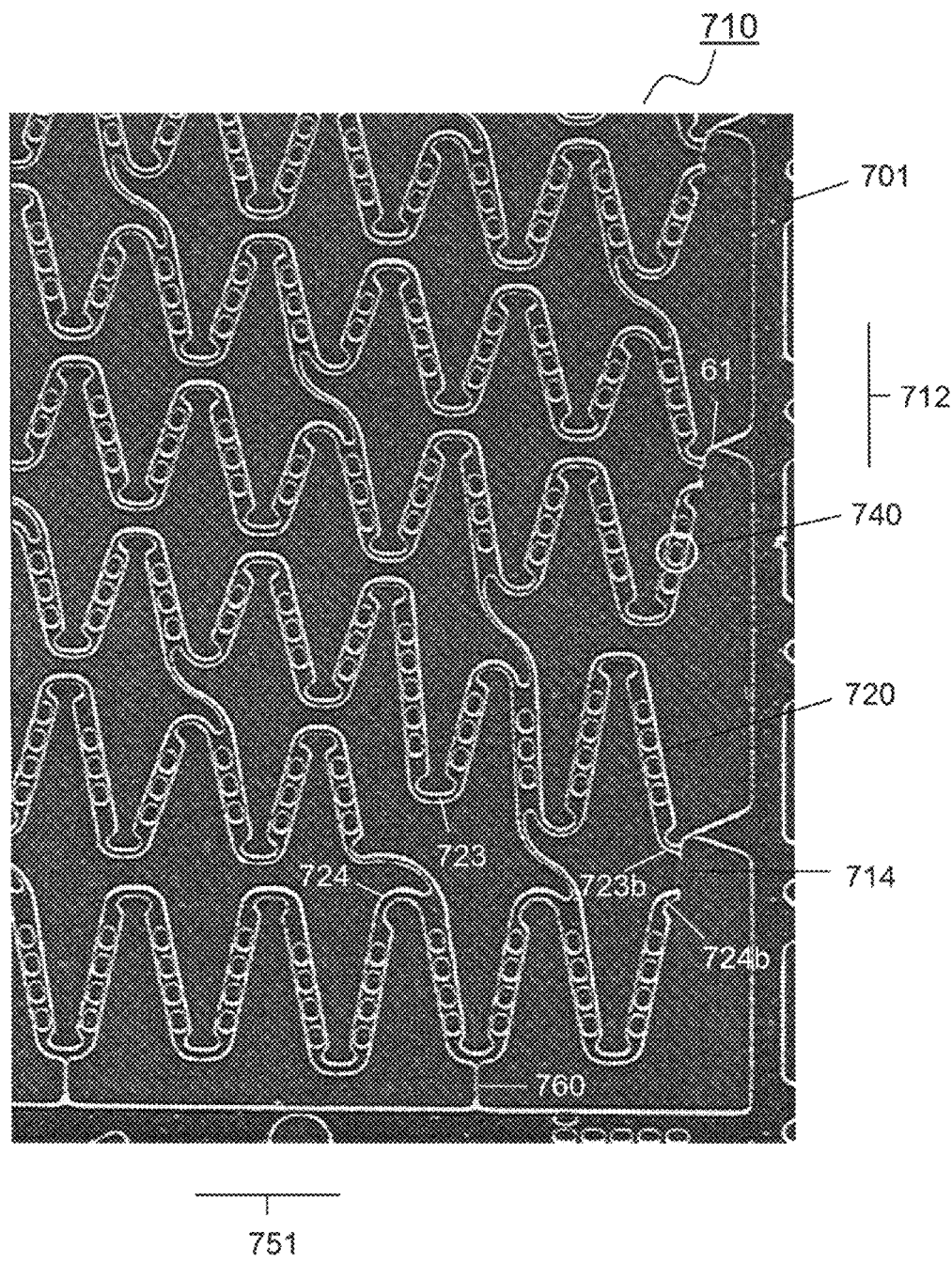
FIG. 49 is a photograph showing an enlarged view of a corner of a first end of a stent pattern fabricated by the tool of FIG. 46, illustrating a portion of a second long side of the stent pattern and the engagement points on flexor loops on the second long side.

The stent pattern cut into a metal sheet is polished to round any sharp edges and remove any excess material from the cutting process. Electro-polishing also renders the surface of the stent smoother and more bio-compatible. Since electro-polishing cannot be performed in the presence of organic materials without degrading the organic materials, electro-polishing is performed before the filling step 4016. FIG. 49 illustrates a portion of a flat stent pattern that has been electropolished.

In step 4016 of FIG. 1D, a composition is deposited into the reservoirs, using the flat reservoir map for the exposed first major surface of the flat sheet. The composition may include a therapeutic agent, a polymer, or a combination of therapeutic agent(s) and a biocompatible matrix or polymer(s). By "therapeutic agent" is meant any drug, agent or compound, including biologics, having an intended activity, e.g., a pharmacologic activity. The term "polymer" is meant to include materials that may facilitate, delay or modify release of the therapeutic agent from the reservoir, or facilitate depositing the therapeutic agent or composition into the reservoir and/or containing it in the reservoir until released. In one embodiment, more than one composition may be deposited into the reservoirs. In another embodiment, different compositions are deposited into different reservoirs. In yet another embodiment, the flat sheet may be flipped over and a second composition (or a second application of a first composition) may be deposited into the reservoirs using the flat reservoir map for the second major surface.

In step 4020, the filled stent pattern is deformed into a tubular shape, as described above. FIG. 47 illustrates the deformation process generally, for stents made from a flat sheet.

In step 4022 of FIG. 1D, the first and second long sides of the filled stent pattern are joined together at the plurality of corresponding engagement points to form the tubular stent. Engagement points may be joined by any suitable process, for example by welding, adhesive, or other means known in the art that will provide the right strength, durability and biocompatibility.

Further details of the steps of the flat-fill method of the invention, and examples of stent pattern features useful in the method, are discussed below with reference to exemplary but non-limiting stent patterns illustrated in FIGS. 46-57.

FIG. 46 illustrates one example of a flat stent pattern tool 705 prepared as in step 4010 of FIG. 1D. The tool 705 is used for cutting or etching a stent pattern into a flat sheet. The tool 705 of FIG. 46 illustrates one type of pattern that was used to cut the stent pattern depicted in FIG. 49, which in turn may be used to generate the filled stent pattern depicted in FIG. 55. In the tool 705 illustrated in FIG. 46, the reservoirs 740 are located on struts 720. In some embodiments, not all struts have reservoirs. In alternative embodiments, the reservoirs may be located on structures other than struts.

A flat reservoir map may be generated based on the tool 705, as in step 4012, or after step 4014, based on a scan of the cut or etched stent pattern. In either embodiment, the flat reservoir map contains information regarding the location of the reservoirs in the flat sheet. This information may be used in a software program for the filling apparatus, to instruct the apparatus where to deposit the composition (i.e., in the reservoirs) in the flat stent pattern, as discussed below with reference to FIG. 53.

The cutting operation may be implemented in any of a number of ways, such as by etching, or by cutting with a find cutting tool, or by cutting with a fine laser, as described above. If etching is implemented in the cutting process of step 4014, then the process is designed to cut through the sheet metal, as described above for step 1014 of FIG. 1A. In embodiments where it is desired that the reservoirs be recesses rather than fenestrations, the reservoirs may be separately cut into the flat sheet before or after the rest of the stent pattern has been cut, or two tools may be used in the etching process (one with and one without the reservoirs), so that the reservoirs are present only on the printed film adjacent one side of the flat sheet.

Figure 48A:
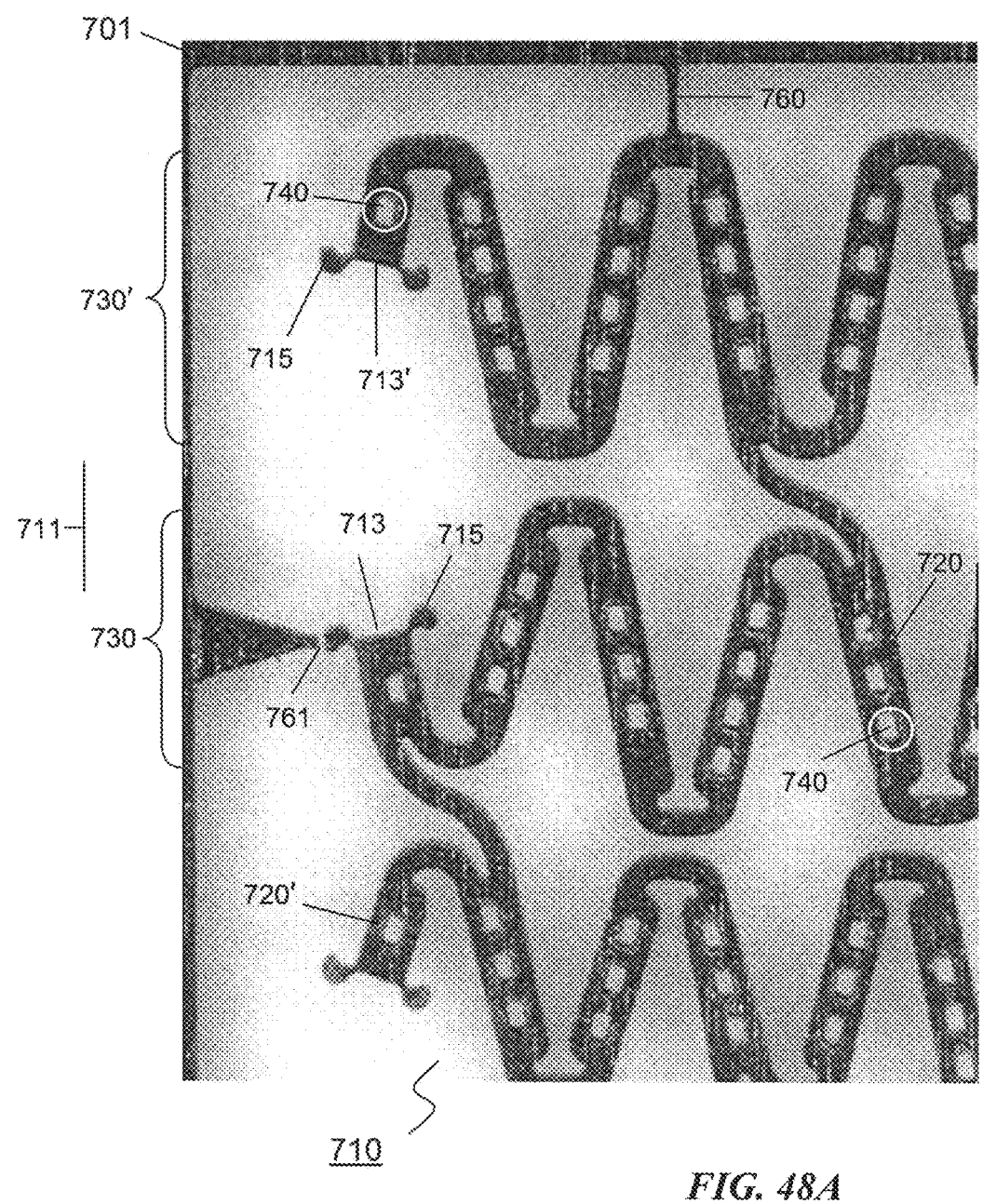
FIG. 48A is an enlarged view of a corner of a second end of the stent pattern of FIG. 3, illustrating a portion of a first long side of the stent pattern and the engagement points on struts on the first long side.

Using the tool prepared in step 4010, a stent pattern is cut into a flat sheet. FIG. 47 depicts a flat metal sheet 701 into which another example of a flat stent pattern 710 having reservoirs 740 has been cut, and illustrates details of a flat stent pattern 710 useful in the method. In particular, the flat stent pattern 710 shown in FIG. 47 has a first long side 711, a second long side 712, a first end 751, a second end 752, and a plurality of struts 720, each strut 720 containing one or more reservoirs 740. Some of the details of the stent pattern of FIG. 47 are shown in FIG. 48A (delineated in FIG. 47 as box "F48A") and in FIG. 48B (delineated in FIG. 47 as box "F48B"). FIG. 49 is a photograph of a portion of a stent pattern 170 fabricated using the tool 705 illustrated in FIG. 46 (delineated in FIG. 46 as box "F49"), and illustrates similar details for this other stent pattern.

Reservoirs may be positioned at various points on the stent structure. Preferably, reservoirs 740 are located on non-flexing portions of the stent, for example on struts 720 as illustrated in FIGS. 46 and 47, but they need not be located on struts. Where reservoirs are located on struts, not every strut must include reservoirs. Preferably, the structures containing reservoirs 740 are wide enough to accommodate the reservoirs without compromising structural integrity and strength. Reservoirs 740 may have any suitable shape or size. Preferably, the reservoirs 740 have enough volume to include the desired dosage of therapeutic agent to achieve the goals of the drug-eluting stent. In the embodiment depicted in FIG. 47, the reservoirs 740 are fenestrations of equal size and relatively uniform distribution. In other embodiments, for certain applications or to achieve particular desired effects, as will be understood in the art, the stent pattern may include reservoirs of non-uniform size and/or distribution, and/or the reservoirs may be recesses. Where differential drug release is desired, either fenestrations or recesses may be employed. Recesses are particularly practical for embodiments where the therapeutic agent is to be released only from one side of the stent.

FIG. 50 shows an alternative embodiment of the invention in which a plurality of stent patterns 710 having reservoirs have been etched or cut into a flat piece of metal 701. Similar to the embodiment depicted in FIG. 6, the flat metal sheet 701 is provided with a plurality of alignment apertures or index holes 716 adapted to receive index pins (not shown) for precisely moving and maintaining the precise alignment of the flat metal sheet 701 and the patterns 710 during the various stages of manufacturing. For example, the plurality of index holes 716 may be sized and disposed to engage the index pins on the base of an apparatus comprising a mandrel for folding the stent pattern into a tubular shape, an example of which is shown in FIGS. 22-24. Similar to the stent patterns described above, each stent pattern 710 has a first long side 711 and a second long side 712, a first end 751, a second end 752.

After a stent pattern, or multiple stent patterns, including a plurality of reservoirs are cut into the flat sheet, the plurality of reservoirs are filled with a composition as described in step 4016 of FIG. 1D. The invention provides a method of depositing the one or more compositions into the reservoirs in a more efficient manner than available with current methods. Preferably, a composition containing a therapeutic agent is used. Any number of useful therapeutic agents may be used with the present invention, for example therapeutic agents useful for treating vascular diseases. Suitable therapeutic agents are known in the art, and include therapeutic agents used for stents filled or coated in the tubular shape. Examples of such therapeutic agents include those described above for flat coating, and at col. 16, line 39-col. 19, line 31 of U.S. Pat. No. 7,179,289 to Shanley et al.; and at col. 7, line 10-col. 9, line 65 of U.S. Pat. No. 7,008,645 to Golomb et al., which are incorporated herein by reference. Particular examples of appropriate drugs include, but are not limited to, rapamycin (sirolimus) or analogs thereof such as everolimus, and paclitaxel. Other suitable composition materials may include biocompatible polymers or non-polymers known in the art and/or materials described for compositions used to fill tubular stents, see e.g., U.S. Pat. No. 6,506,437 to Harish et al. and U.S. Pat. No. 7,179,289 to Shanley et al., which are incorporated herein by reference.

An example of a system for filling the reservoirs of the stent pattern with the composition is shown schematically in FIG. 51A. FIG. 51A shows a cross-section through a stent pattern 710 having reservoirs 740 and a schematic illustration of a system for flat-filling reservoirs with a composition. In this embodiment, the reservoirs 740 are fenestrations, and therefore the stent pattern 710 is seen placed on a base 747 to prevent leakage during the filling process. A composition 741 may be expelled or released from a nozzle 745, by methods known in the art, e.g., by ink-jet, into the reservoirs 740 to form deposits 742 in the flat stent pattern 710. The nozzle 745 may be moved in the X-Y direction over the reservoirs 740 according to the flat reservoir map generated from a tool or a scan of the stent pattern-cut flat sheet (see step 4012 of FIG. 1D). For example, information regarding the precise location of the reservoirs in the stent pattern may be inputted into a software program that controls the position of the nozzle and the depositing function. In this way, both the location and amount of composition may be fined tuned based on the particular stent pattern, reservoir size, and type of composition(s) being deposited. In embodiments where multiple stent patterns are filled simultaneously, as for example may be applied to an embodiment such as that illustrated in FIG. 50, the filling apparatus may include multiple nozzles, each for a different stent pattern in the flat sheet. To accurately deposit composition into the reservoirs of the flat stent pattern, any of the techniques that have been developed in the micro-electronics industry for flat application of a material onto accurate positions may be applied in the present invention.

Figure 52:
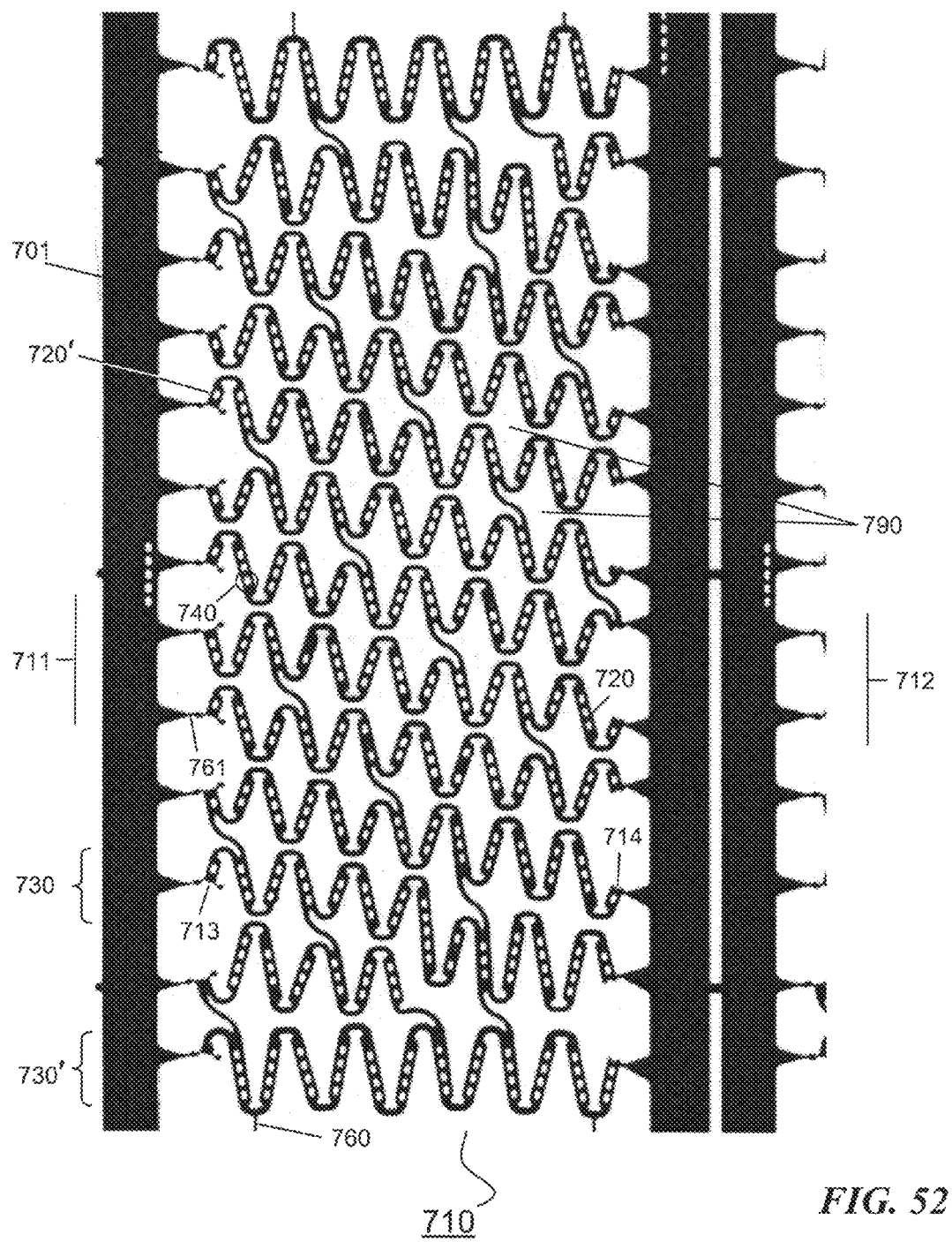
FIG. 52 illustrates under back-lighting the location of reservoirs in an example of a single stent pattern cut into a flat metal sheet.
Figure 53:
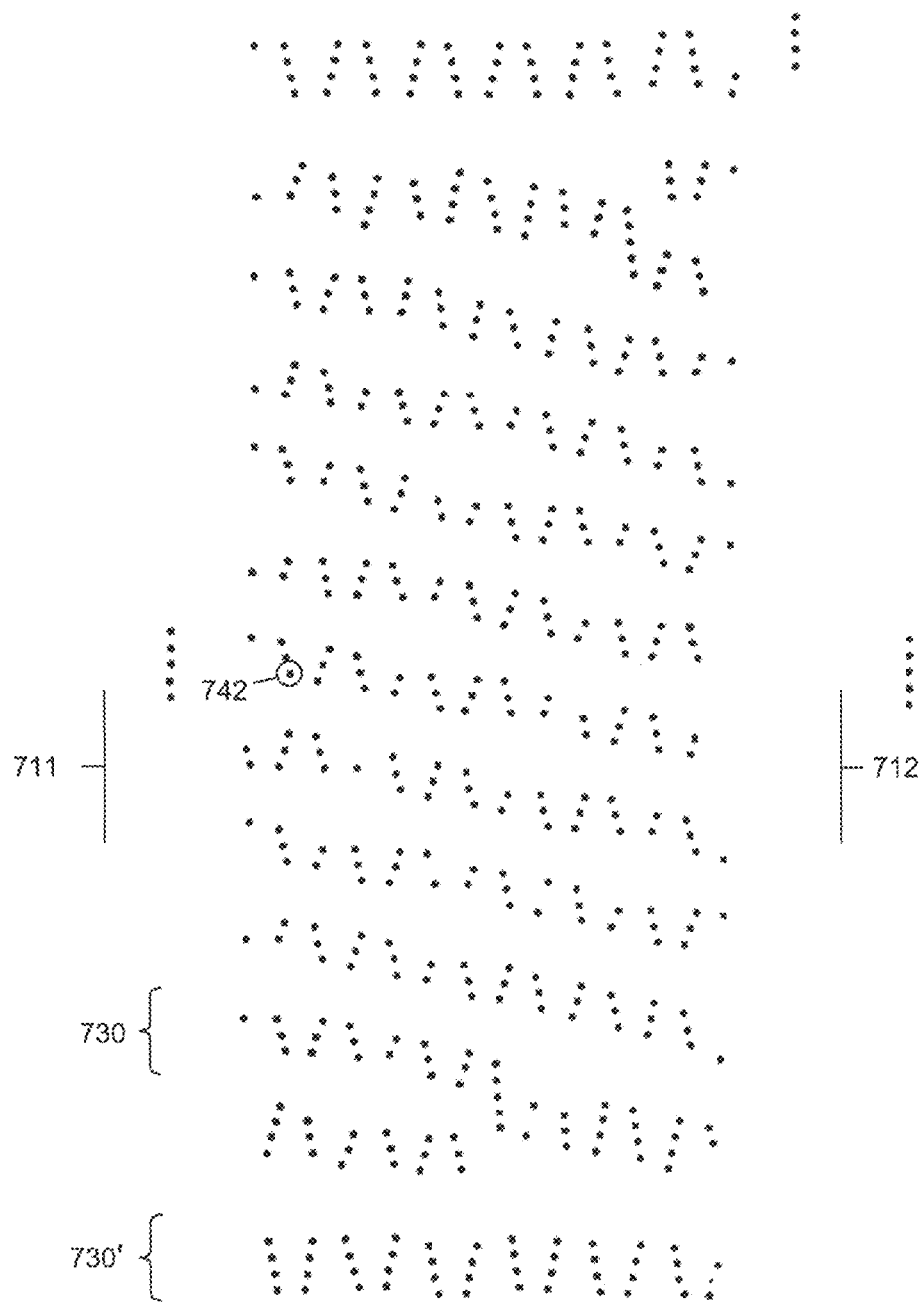
FIG. 53 illustrates under back-lighting the flat pattern of deposits on glass, based on the stent pattern illustrated in FIG. 52.
Figure 54:
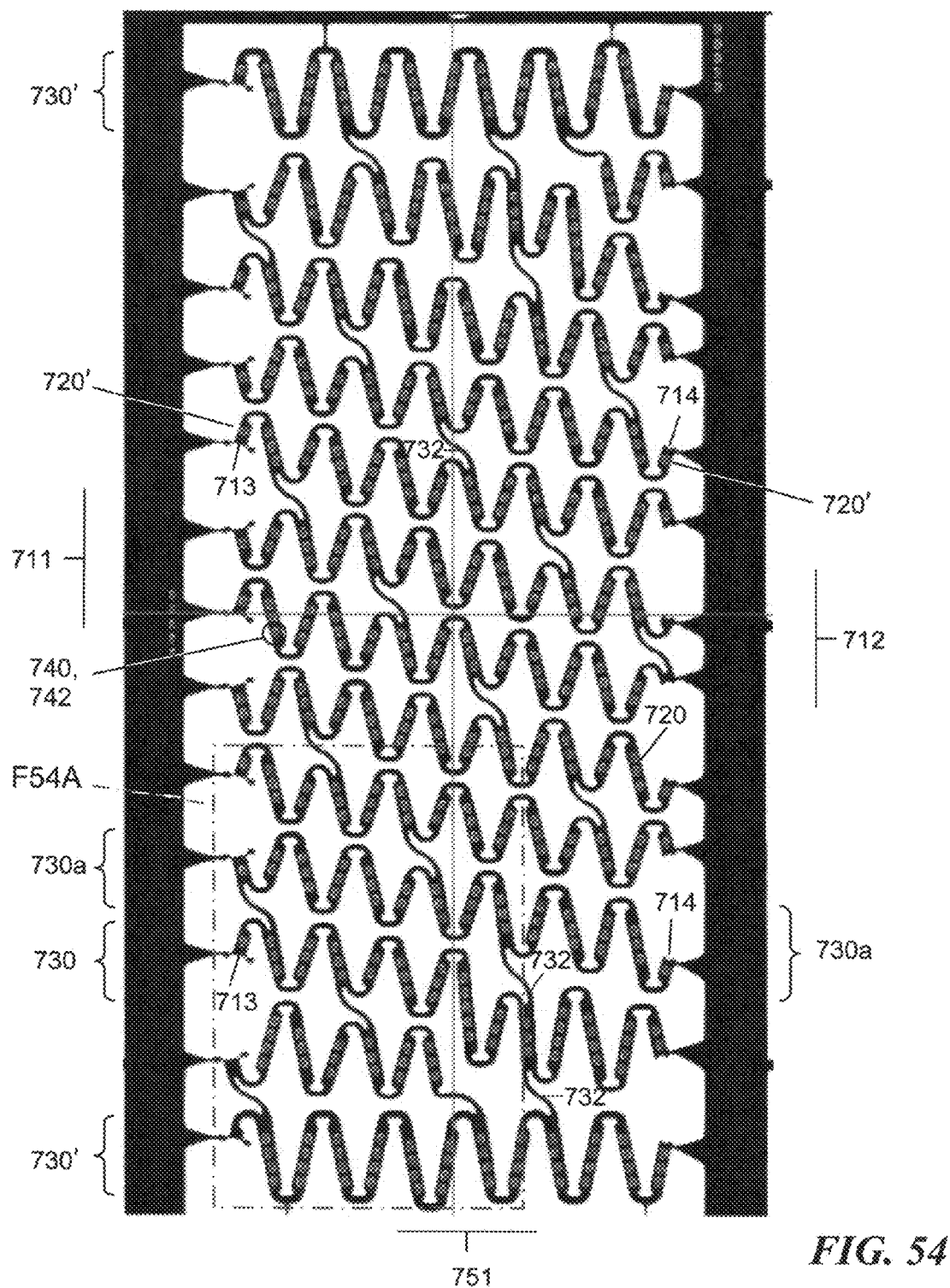
FIG. 54 shows a filled stent pattern, illustrating the overlap of the reservoirs in the stent pattern of FIG. 52 and the flat pattern of deposits of FIG. 53.
Figure 54A:
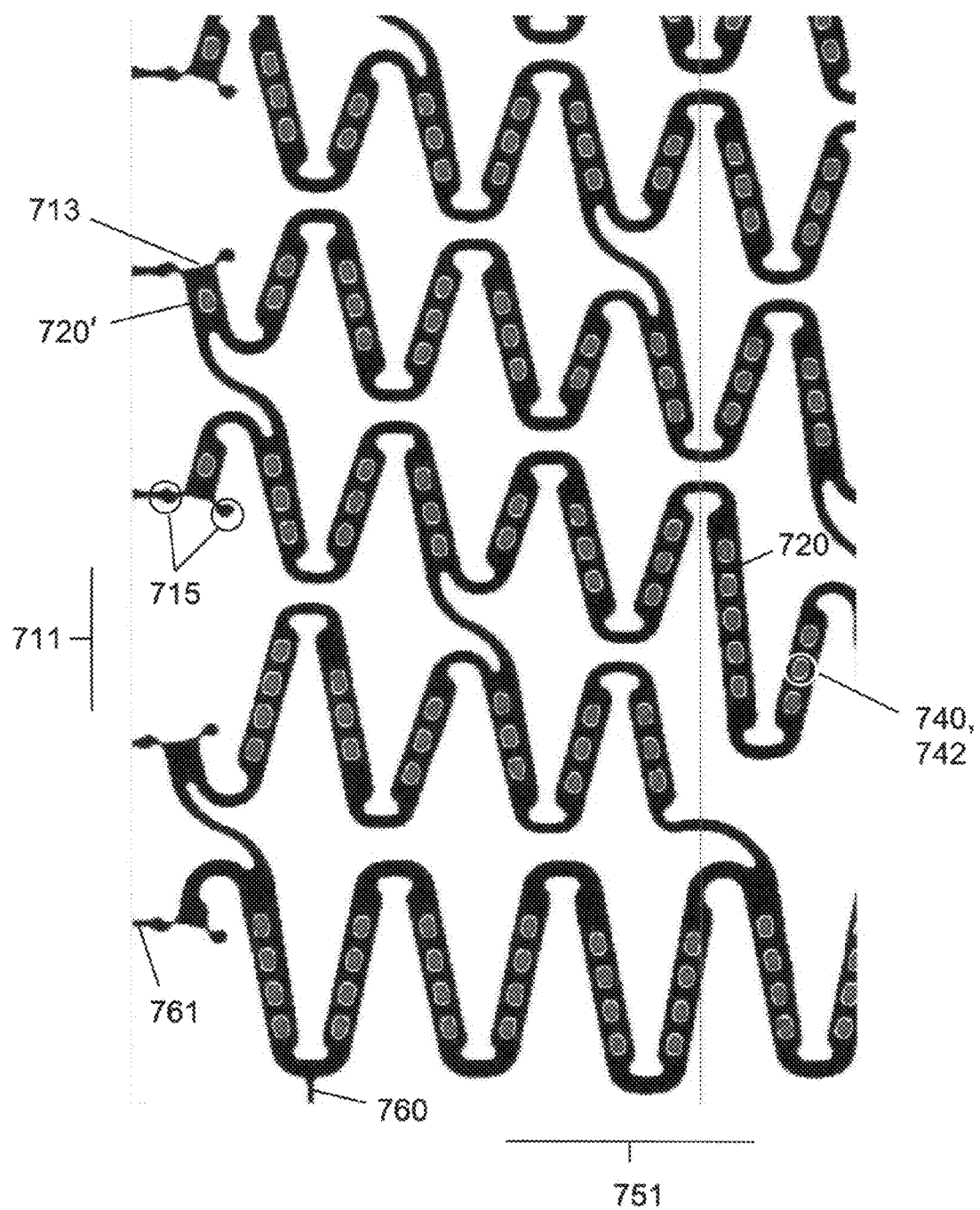
FIG. 54A is an enlarged view of a portion of the filled stent pattern of FIG. 54.

FIGS. 52-54 illustrate an advantage of the methods of the invention over prior art procedures of depositing compositions into stents containing reservoirs—flat filling. The flat filling method of the invention facilitates automated loading of composition into the reservoirs 740 of the stent pattern 710, so that the reservoirs 740 may be filled efficiently, accurately and with high quality control. FIG. 52 shows the stent pattern 710 of FIG. 47, back-lit to better illustrate the location of the reservoirs 740. FIG. 53 illustrates deposits 742 generated on glass based on the flat reservoir map, in the absence of the flat metal stent pattern of FIG. 52. Specifically, composition may be accurately deposited into all of the reservoirs of the stent pattern at the same time, in a controlled manner. FIG. 54 illustrates how the deposits 742 of FIG. 53 overlap the location of reservoirs 740 in the flat stent pattern 710 of FIG. 52. FIG. 54A (delineated in FIG. 54 as box "F54A") shows more clearly the accurately placed deposits 742 in reservoirs 740 located on struts 720.

Figure 55:
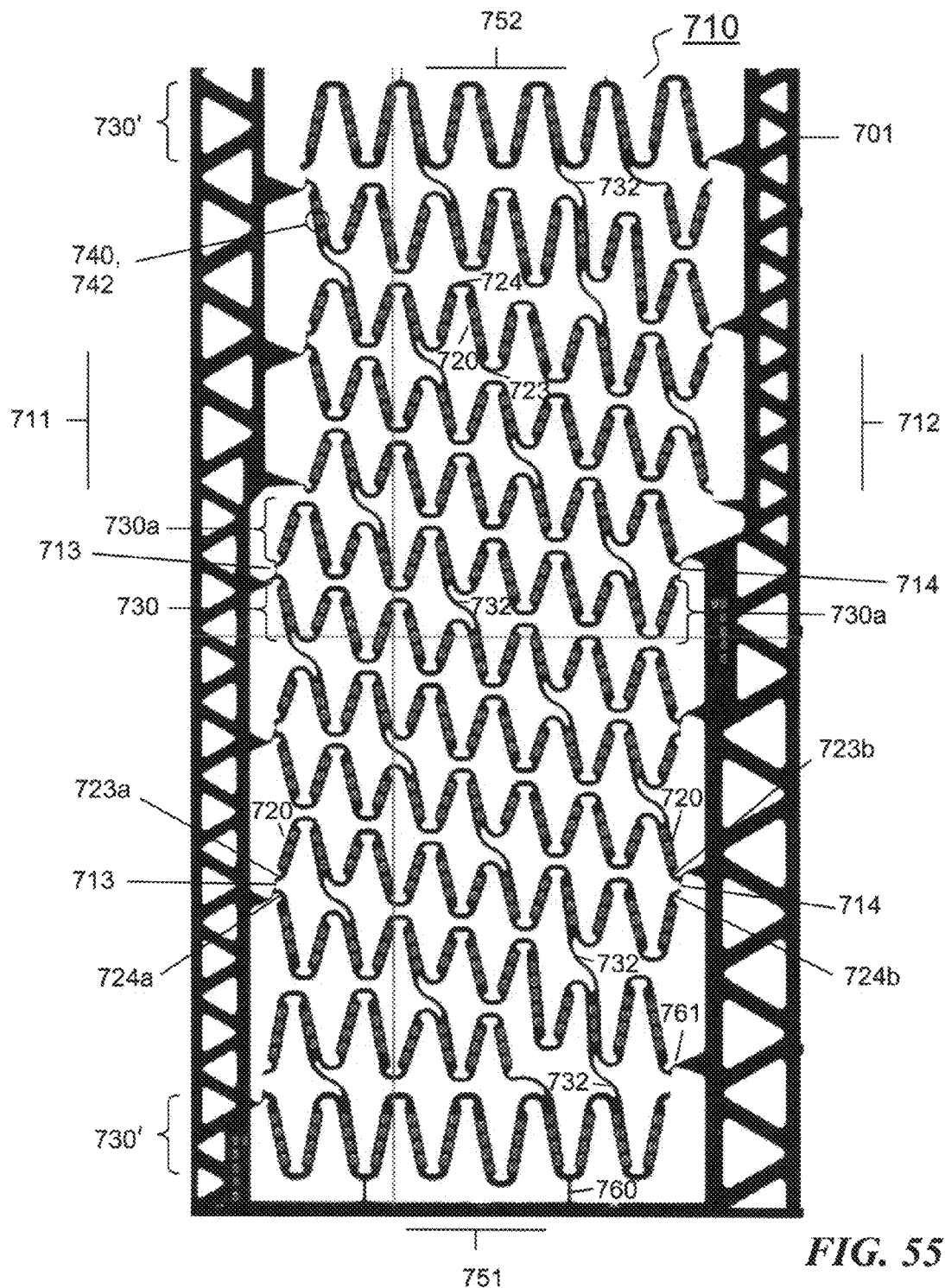
FIG. 55 shows a reservoir-filled stent pattern similar to FIG. 54, but fabricated using the tool illustrated in FIG. 46, illustrating the overlap of the reservoirs in the stent pattern and flat pattern of deposits.

FIG. 55 illustrates, in a manner similar to FIG. 54—by overlay of the deposits and the stent pattern, an embodiment of a filled stent pattern 170 prepared from the tool 705 illustrated in FIG. 46, as in FIG. 49. Reservoirs 40 are shown filled with deposits 742. As in FIG. 54, the accurate deposition of composition according to the method of the invention is illustrated.

The major factors that make the inventive flat filling process better than filling a tubular stent with identical reservoirs are numerous. An advantage of filling reservoirs of the stents when they are in a flat panel includes better cost efficiency. For example, the process of flat filling is much faster. The drug delivery stent further permits faster filling of reservoirs, by filling from both sides of the stent. In current methods the composition contains solvent that must evaporate and therefore has a volume that may be 2-5 times greater than the composition after drying. This conventional process requires repeated cycles of filling and drying. By depositing the composition into the reservoir from both sides of the flat sheet, the time for the filling step may be shortened by at least half, by allowing two sides to dry simultaneously. Further, when using a panel of multiple-up-etched stent patterns as shown in FIG. 50, multiple nozzles may be employed to fill multiple stents simultaneously and speed up the process. There is an economical advantage to fill reservoirs of a single flat stent using the method of the invention, but the applicability for filling multiple stents provides a greater economic impact. In addition, the quality gain of filling reservoirs of many stents in one process and the uniformity of the fill process and quality control check across a lot is of great importance.

The process of flat filling also is more accurate, providing improved quality control. The fact that the stents patterns are not transformed into a tubular shape between the time of cutting and the time of filling insures an accurate filling map, unlike the filling process of tubular stents that are cut from a tube and then crimped on a pin with a plastic sleeve to seal the bottom of the reservoirs as to prevent leaks. The crimping process deforms the stent and, therefore, the map of the reservoirs used for cutting is no longer spatially accurate for filling. In embodiments where a plurality of identical stent patterns have been cut into a flat metal sheet, as illustrated in FIG. 50, the drug filling process may use the same flat reservoir map for each of the stent patterns, thereby improving accuracy and quality control within a batch of stents. Quality and accuracy may also be maintained across batches of stents using the methods of the invention.

The invention further provides the advantage of differentially depositing a composition in the vessel wall side (outside the cylinder) and the luminal side (inside the cylinder) of the reservoir of the stent pattern prior to forming the tubular stent. The complete control of filling the reservoirs on each side of a flat panel separately allows a high degree of accuracy of drug filling, whether similar or different treatments are desired on both sides.

Flat filling also eliminates dripping and other three-dimensional effects that are of concern when filling a tubular stent. For example, the need to rotate the stent during filling results in holes facing downward before the polymer and drug have a chance to dry.

Once the reservoirs have been filled, the stent pattern is folded to form the stent, as shown in step 4020 of FIG. 1D. The deformation of a stent pattern is illustrated generally in FIG. 3. The deformation process is a folding process, as shown, so that the stent pattern is folded to bring the first long side 28, in this case having protrusions 38, toward the second long side 28'. The flat stent pattern is designed to be transformed into a tubular structure so that the first long side comes into contact with the second long side at engagement points and detached from the flat sheet into which it was cut. A mandrel of any desired cross section may be used to transform the stent pattern into a tubular stent, as described above. With reference to FIGS. 46 and 47, the first long side 711 includes a plurality of first engagement points 713 and the second long side 712 includes a plurality of corresponding second engagement points 714. First and second engagement points 713, 714 are points of contact between the first and second sides 711, 712 of the stent pattern 710 when the filled stent pattern is folded to form the tubular filled stent. Specifically, the engagement points 714 on the second long side 712 are disposed and adapted to receive and engage the engagement points 713 on the first long side 711.

Figure 48B:
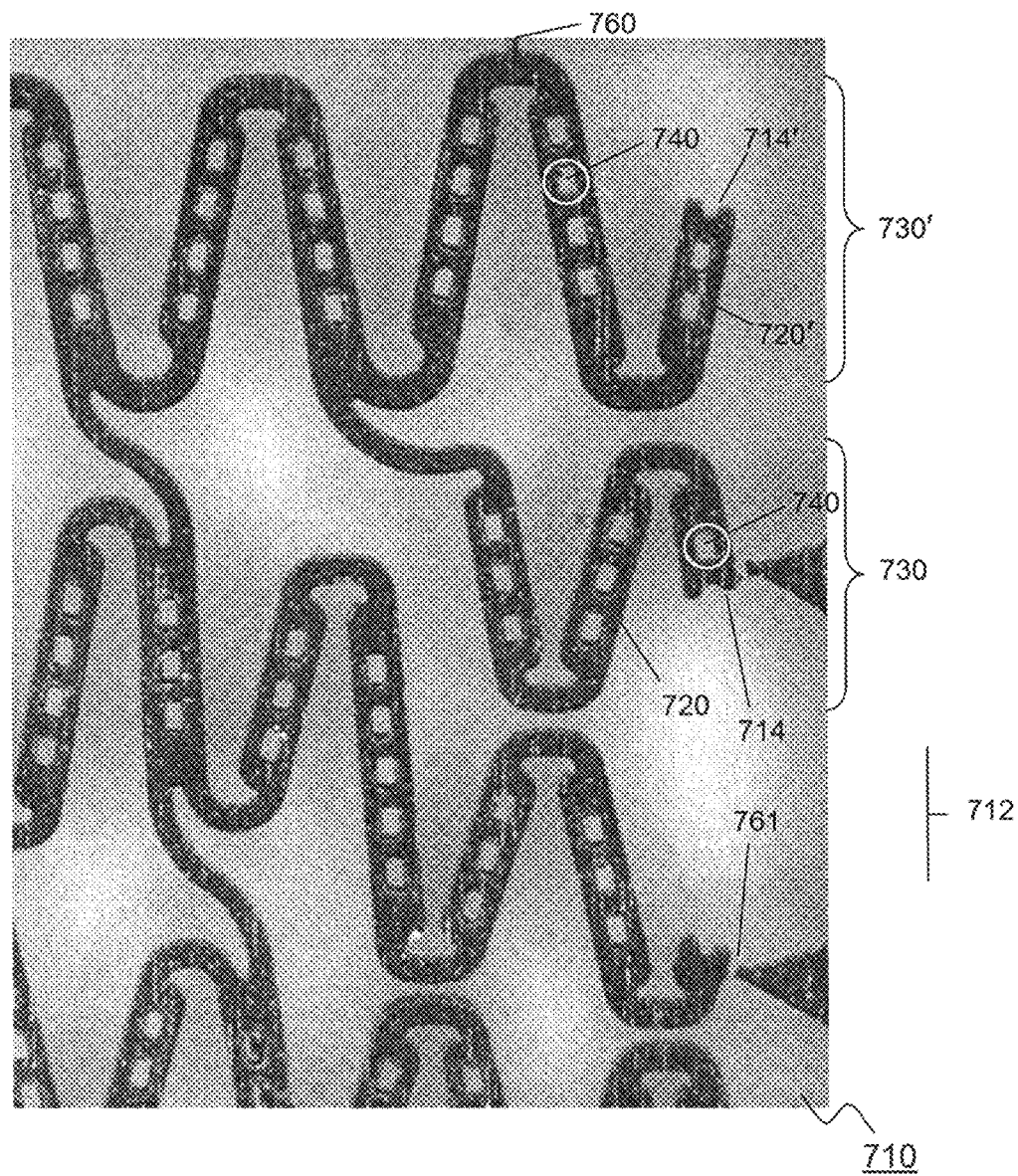
FIG. 48B is an enlarged view of a corner of a second end of the stent pattern of FIG. 47, illustrating a portion of a second long side of the stent pattern and the engagement points on struts on the second long side.

FIGS. 48A and 48B illustrate one form of engagement points 713, 714 that are located on partial struts 720' with reservoirs. FIG. 48A is an enlarged view of a corner of the second end of the stent pattern 710 of FIG. 47, including the first long side 711 and first engagement point 713, 713' located at the end of a partial strut 720' containing one or more reservoirs 740. A plurality of protrusions 715 are shown on the first engagement points 713, 713'. FIG. 48B is an enlarged view of the opposite corner of the second end of the stent pattern 710 shown in FIG. 47, depicting the second long side 712 and second engagement point 714, 714' located at the end of a partial strut 720' containing one or more reservoirs 740. Similarly, in the filled stent pattern illustrated in FIG. 54A, the location of first engagement points 713 on partial struts 720' is shown, as are protrusions 715 and stent attachment points 760, 761.

In other embodiments, however, the engagement points may be located on struts without reservoirs, at the end of a whole strut, or on structures other than struts. For example, engagement points may be located on flexible round loops that connect each strut with its neighboring strut. Thus, as illustrated for example in FIGS. 46, 49 and 55, engagement points 713, 714 are located on midpoints of flexor loops. In this embodiment, flexor loops 723, 724 are structures that connect first ends and second ends of laterally adjacent struts 720. The flexor loops 723, 724 have a narrower width than the struts 720 containing reservoirs 740, which makes them more flexible than the struts 720, to facilitate crimping of the stent for delivery and expanding the stent during stent deployment. Referring to FIGS. 46 and 55, the first and second engagement points 713, 714 in this embodiment are engagement point pairs, located at midpoints of adjacent flexor loops. Specifically, the pair in engagement point 713 comprises the end of a first half flexor loop 723a and the end of adjacent first half flexor loop 724a with bridge material between, and the pair in engagement point 714 comprises the end of a second half flexor loop 723b and the end of adjacent second half flexor loop 724b with bridge material between. The bridge material may help with stability of the stent pattern and is useful in the joining step where the joining method is welding. FIG. 49 depicts an enlarged view of a corner of the first end 751 of the stent pattern 710, including the second long side 712 and second engagement point 714 located on the end of half flexor loops 723b, 724b. Also depicted are the sheet attachment points 760, 761, where the stent pattern 710 is attached to the metal sheet 701 into which the pattern was cut or etched.

The stent pattern 710 in FIGS. 48A and 48B is shown attached to the flat metal sheet 701, as illustrated by the sheet attachment points 760, 761. Attachment points 760, 761 have a very narrow width to facilitate removing the stent pattern 710 from the flat metal sheet 701, for example by laser cutting. In particular, the first and second long side sheet attachment points 761 are so thin that the physical connection is barely visible in FIGS. 48A and 48B. The locations of the sheet attachment points 760, 761 where the stent pattern 710 is attached to the flat metal sheet 701 are best seen in FIGS. 52 and 54A, where the backlighting enhances the image, and also in FIGS. 49 and 55. The stent pattern 710 is detached at side attachment points 761 before folding, but may be detached from end attachment points 760 before or after folding the stent pattern into a tubular shape.

The long sides of the stent pattern are joined via the engagement points, as shown in step 4022. Engagement points 713, 714 may be joined by any number of means known in the art, as described above. In one embodiment, the engagement points are welded together. This may be accomplished in a variety of methods well known to those skilled in the art, however, in a particular embodiment a plurality of welds are utilized. The weld may comprise a plurality of weld runs, for example, two weld runs. The weld run may be offset from the point where the engagement points contact each other, for example the offset may be about 0.01 mm. The stent may be provided with a weld that is equal to or about 20% wider and/or thicker than the other equivalent portions of the stent. In one embodiment, the weld has a width and thickness of about 125% the width and thickness of equivalent struts.

As noted above, in the embodiments illustrated in FIGS. 47, 48A and 48B, the first engagement points 713 include protrusions 715, or extra material. The protrusions 715 are of particular use when welding the first and second long sides 711, 712 together to form the tubular stent. The heat produced by the welding melts the protrusion 715 material. The material is then drawn towards the engagement points 713, 714 to which it is attached and into the welded area, where it becomes part of and imparts additional strength to the weld. If the first engagement points 713 include protrusions 715, a protrusion 715 is joined to the corresponding second engagement point 714 on the opposite side. As shown in FIGS. 47 and 48A, the protrusions 715 extend beyond the first engagement points 13. The protrusions may overlap the engagement points of the second long side after deformation of the stent pattern, as illustrated in FIG. 5B, where one embodiment of protrusions 38 located on the first long side 28 is shown overlapping the second long side 28'. As illustrated in FIGS. 3 and 4, the protrusions 38 are used to form weld points to connect the first and second long sides along a weld line 170. The resulting weld point does not alter the general pattern of the stent, but provides a strong enough weld to avoid a "weak point" in the stent. FIGS. 4 and 5B illustrate generally the connection of a protrusion of the first long side to the second long side in an example of a stent, and preservation of the stent pattern.

In some embodiments, instead of having engagement points with protrusions, each engagement point 713, 714 may be designed as a pair of points with a bridge of material disposed between, and connecting, the pair, as illustrated for example in FIGS. 49 and 55. In embodiments such as those illustrated in FIGS. 49 and 55, the bridge material is useful in welding the two halves of each flexor loop 723, 724. The bridge imparts additional strength to the welds of the finished stent. The bridge also may impart additional stability to the stent pattern and facilitate alignment during manufacturing. An alignment means may be utilized to maintain the alignment and the bridge may be cut at a point that leaves two substantially equal parts attached to half of the engagement point pair. The bridge may be cut in a variety of ways well known to those skilled in the art, however, in a preferred embodiment, a laser is utilized. As the engagement point pairs are welded together, the heat produced by the welding melts the bridge material and the material is drawn towards the first engagement points to which the material is attached. Thus, for the stent pattern embodiment illustrated in FIGS. 55 and 57, the welding step draws the bridge material into the flexor loops 723, 724, which strengthens the weld points 771. Like the protrusions, the resulting weld points 771 do not alter the general pattern of the stent, but provide a strong enough weld to avoid a "weak point" in the stent. This can be appreciated in FIG. 57. In an alternative embodiment, only pairs of first engagement points may be provided with a bridge disposed between each first engagement point comprising the pair, the bridge having a width that is less than the width of the other portions of the stent, similar to the embodiment depicted in FIGS. 25 and 26.

As the person having ordinary skill in the art will appreciate from this description, first and second engagement points may be located on other stent structures depending on the particular stent pattern being used, and protrusions or bridges used as applicable to the particular stent pattern. The engagement points are designed so that when they are attached, the stent pattern is preserved across the line of attachment, as discussed in more detail below.

The orientation and width of the engagement points of the stent pattern are typically designed so that, in accordance with the method of the invention, when the engagement points are joined, the pattern is approximately preserved across the line of attachment. Thus, for example, since a protrusion or bridge is typically designed to extend the width of one strut or whatever structure it is attached to, the stent pattern may be approximately preserved across the weld line, as shown for example in FIGS. 4, 5B and 57.

Figure 56:
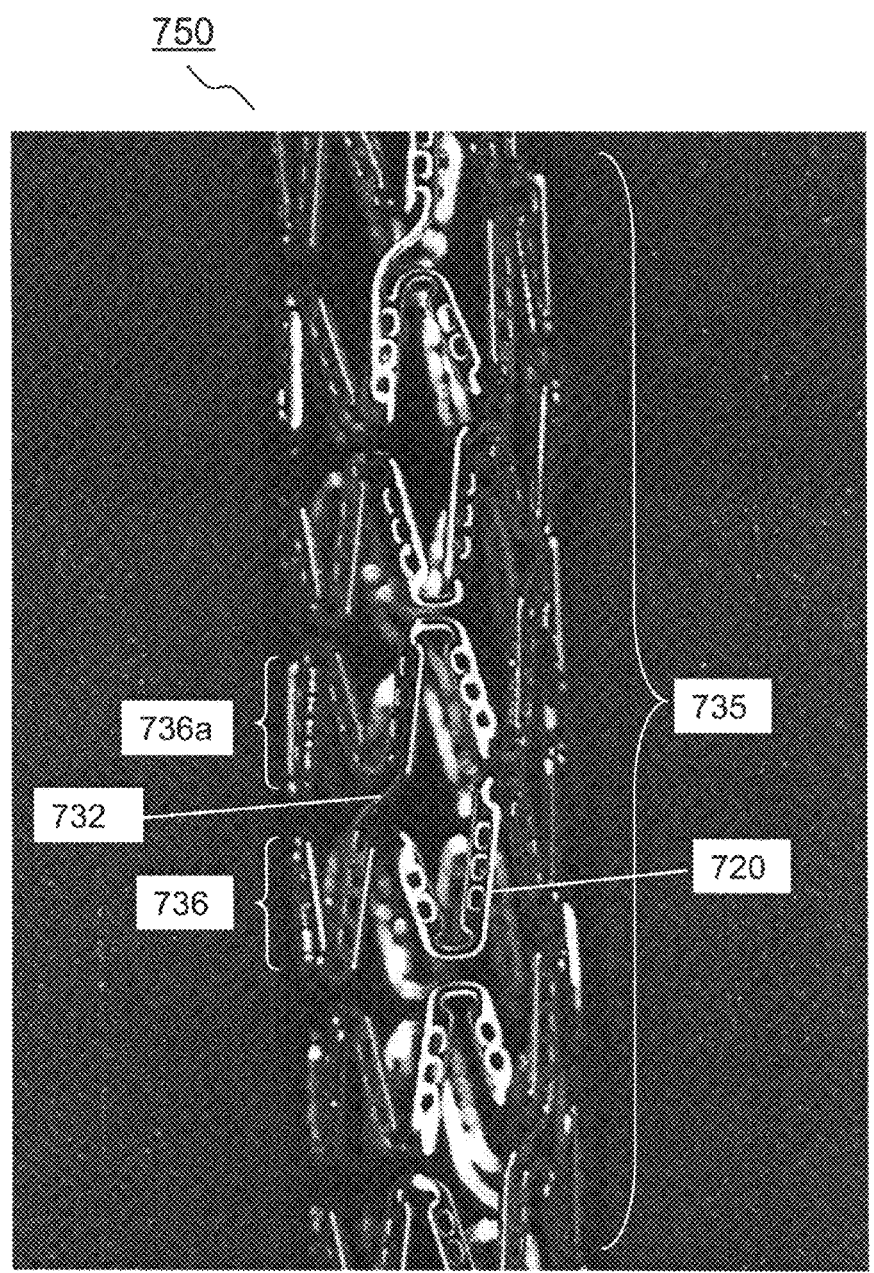
FIG. 56 is a photograph of a stent, as manufactured, after forming the filled stent pattern into a tubular shape and attaching the engagement points.
Figure 57:
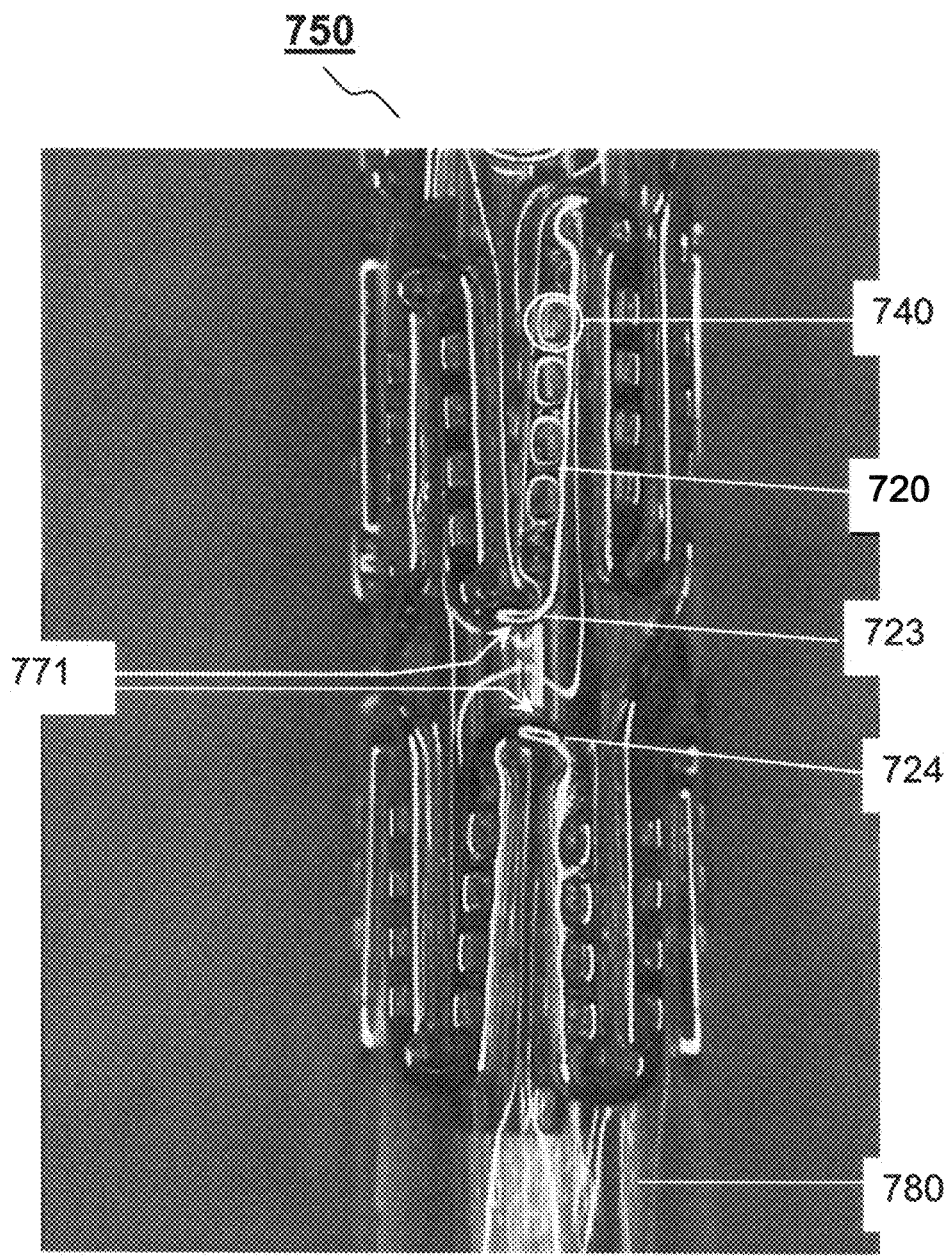
FIG. 57 is a photograph of the weld points of a finished filled stent crimped on a balloon catheter.

For purposes of illustrating how the pattern may be maintained across a weld line, reference is made to details of the particular examples of stent patterns 710 depicted in FIGS. 54 and 55, which are formed into spiral stents, as shown in FIGS. 56 and 57, respectively. When the engagement points on first and second sides 711, 712 of the stent pattern depicted in FIG. 54 are joined, the strut portions 720' are connected to form full struts to maintain the stent pattern across the connection line (e.g., weld line), such that connection points (or weld points) are located in the middle of a strut 720. Similarly, in the embodiment depicted in FIG. 55, the first engagement points 713 comprising the ends of half flexor loops 723a, 724a and the second engagement points 714 comprising ends of the complementary half flexor loops 723b, 724b (see also FIG. 49) match to form whole flexor loops 723, 724, when joined.

Thus, when this stent pattern 710 is folded into a tubular shape and the engagement points 713, 714 are welded, the weld points 771 will be located on midpoints of flexor loops 723, 724, as illustrated in FIG. 57.

Further, in the embodiments shown in FIGS. 54 and 55, central serpentine segments 730 are arranged slightly offset from orthogonal to the long sides 711, 712 of the stent pattern, such that the structure(s) that make up the first engagement point 713 located on a first end of one serpentine segment 730 and match(es) up with the structure(s) that make up the second engagement point 714 located on a second end of a longitudinally adjacent serpentine segment 730a. Therefore, when the stent pattern is transformed into a tubular structure and the complementary first and second engagement points 713, 714 are joined, the central serpentine segments 730 form a continuous central spiral portion of the stent with a continuous serpentine pattern along the spiral. Similarly, each end serpentine segment 730' forms a right cylinder around the circumference at the ends of the stent.

Thus, FIG. 56 shows the central portion of a stent 750 embodiment formed from a stent pattern like that illustrated in FIGS. 47 and 54, as manufactured. Longitudinally adjacent windings 736, 736a of the continuous serpentine spiral 735 are shown, connected by a flexible connector 732. Similarly, FIG. 57 shows an end of a stent 750 embodiment formed from a stent pattern like that illustrated in FIG. 55 and crimped onto a balloon catheter 780. The weld points 771 connecting the halves of the flexor loops 723, 724 blend into the stent structure, thereby preserving the stent pattern across the weld line. The zig-zag pattern of the serpentine spiral (and of the end ring, not shown) of this embodiment is continuous across the newly formed flexor loops 723, 724 at the weld line, as illustrated in FIG. 57.

As will be appreciated by one skilled in the art based on the description herein, many other stent patterns having reservoirs may be similarly designed and fabricated using the method of the invention to produce a drug delivery stent having a smooth and continuous the pattern across the line where the first and second long sides are connected.

Details regarding exemplary apparatuses that may be used to form the drug-filled stent from the flat sheet and to align and weld the stent in tubular form are described above. For example, the first and second long sides of the rolled, filled stent pattern may be joined using an apparatus as shown in FIGS. 22-24, or with another suitable apparatus, and the engagement points may be welded together using an apparatus as shown in FIGS. 38-42.

In one embodiment, the drug-filled stent may be additionally coated with another drug composition, as described above.

It will be appreciated by persons having ordinary skill in the art that many variations, additions, modifications, and other applications may be made to what has been particularly shown and described herein by way of embodiments, without departing from the spirit or scope of the invention. Therefore, it is intended that scope of the invention, as defined by the claims below, includes all foreseeable variations, additions, modifications or applications.

What is claimed is:
1. A method of fabricating a filled stent comprising the steps of:
cutting a plurality of stent patterns into a flat sheet of metal, each of said stent patterns comprising stent members and reservoirs, and first and second long sides, each of said reservoirs located on at least one of a first and second major surface and exposed exclusively thereto;

filling said reservoirs of said flat stent pattern with a composition;
folding said filled stent pattern into a tubular shape so that said first and second long sides meet; and
attaching said first and second long sides to form a filled stent;
wherein said filled stent reservoirs and at least one of the first and second major surface are exposed to at least one of a vessel lumen or a vessel wall when the stent is implanted in a vessel.

2. The method of claim 1, wherein said filling step includes filling reservoirs of multiple stent patterns simultaneously.

3. The method of claim 1, wherein said attaching step comprises welding.

4. The method of claim 1, further comprising, prior to said cutting step, the step of preparing a flat stent pattern tool, wherein said cutting step includes employing said tool to generate said stent patterns.

5. The method of claim 1 or 4, further comprising, prior to said filling step, the step of generating a flat map containing information regarding the location of said reservoirs based on one of the group consisting of: said cut flat stent pattern and a tool used for cutting said flat stent pattern; wherein said filling step includes using said flat map to fill said reservoirs.

6. The method of claim 5, wherein said generating a flat map step is performed before said cutting step.

7. The method of claim 5, wherein said generating a flat map step is performed after said cutting step.

8. The method of claim 1, wherein said stent members are struts.

9. The method of claim 1, wherein said first long side includes first engagement points and said second long side includes second engagement points and said attaching step includes attaching said first and second long sides at said first and second engagement points, wherein said engagement points are located on said struts.

10. The method of claim 1, wherein said first long side is provided with a plurality of pairs of engagement points, said second long side is provided with a plurality of pairs of engagement points, said plurality of pairs of engagement points disposed substantially opposite each other, said engagement points sized and disposed to communicate when said stent pattern is deformed and rolled into a tubular shape, each pair of said first long side engagement points provided with a bridge disposed between each first long side engagement point comprising said pair, said bridge having a width that is less than the width of other portions of said stent pattern;
wherein said folding step includes disposing a mandrel having a substantially cylindrical external surface and a longitudinal axis between said first long side and said second long side of said sheet, said longitudinal axis substantially parallel to said first and second long sides, and deforming said filled stent pattern around said mandrel into a tubular shape so that said first long side pairs of engagement points contact said second long side pairs of engagement points;
wherein said attaching step includes attaching each of the engagement points to the engagement point with which it is in contact;
said method further comprising, after said folding step: cutting said bridge.

11. The method of claim 1, wherein said deforming includes allowing a portion of said tubular shaped stent pattern to remain attached to said sheet of metal;
said method further comprising, after said attaching step: disconnecting said filled stent from said sheet.

12. The method of claim 1, further comprising: electropolishing said flat stent pattern before said filling step.

13. A stent fabricated by the method of claim 1.

14. A method of filling reservoirs of a drug eluting stent comprising:
providing a flat stent pattern, wherein said stent pattern includes a plurality of reservoirs, wherein said reservoirs are located on a major surface;
generating a flat map containing information regarding the location of said plurality of reservoirs on said flat stent pattern, said flat map based on one of the group consisting of: said cut flat stent pattern and a tool used for cutting said flat stent pattern;
depositing a composition into said reservoirs using said flat map, while said stent pattern is in a flat configuration.

15. The method of claim 14, wherein said providing step includes providing a plurality of stent patterns, each having reservoirs, said depositing step comprising filling reservoirs of multiple stent patterns simultaneously.

16. A method of fabricating a coated stent comprising the steps of:
cutting a plurality of stent patterns into a flat sheet of metal, each of said stent patterns comprising a plurality of discrete portions, a luminal surface, a vessel wall surface, a first long side, and a second long side;
coating said discrete portions on a surface of each stent pattern with a composition to form a coated stent pattern;
folding said coated stent pattern into a tubular shape so that said first and second long sides meet; and
attaching said first and second long sides to form a coated stent,
wherein said coated surface is exposed to at least one of said vessel lumen or said vessel wall when said stent is implanted in a vessel.

17. The method of claim 16, wherein said discrete portions are non-bending portions.

18. The method of claim 17, wherein said non-bending portions are struts.

19. The method of claim 16, wherein said discrete portions are spots.

20. The method of claim 19, wherein said spots are located on stent struts.

21. The method of claim 16, further comprising, prior to said cutting step, the step of preparing a flat stent pattern tool, wherein said cutting step includes employing said tool to generate said stent patterns.

22. The method of claim 16 or 21, further comprising, prior to said coating step, the step of generating a flat map defining said discrete portions; said coating step including using said flat map to coat said discrete portions.

23. The method of claim 22, wherein said generating a flat map step is performed before said cutting step.

24. The method of claim 22, wherein said generating a flat map step is performed after said cutting step.

25. The method of claim 16, wherein said coating composition includes a therapeutic agent.

26. The method of claim 16, wherein said coating step includes coating said discrete portions of said luminal surface with a coating composition comprising a first therapeutic agent and coating said discrete portions of said vessel wall surface with a coating composition comprising a second therapeutic agent.

27. The method of claim 16, wherein said coating step includes coating said discrete portions of said vessel wall surface but not said luminal surface.

28. The method of claim 16, wherein said coating step includes coating said discrete portions of said luminal surface but not said vessel wall surface.

29. The method of claim 16, wherein said coating step includes coating discrete portions of multiple stent patterns simultaneously.

30. The method of claim 16, wherein said coating substance is applied by ion beam spraying.

31. The method of claim 16, wherein said coating substance is applied by inkjet.

32. The method of claim 16, wherein said attaching step comprises welding.

33. The method of claim 16, wherein said first long side comprises a plurality of first engagement points and said second long side comprises a plurality of corresponding second engagement points, said first engagement points having a protrusion; wherein said attaching step comprises attaching each of said plurality of first engagement points to a corresponding second engagement point.

34. A stent fabricated by the method of claim 16.

* * * * *